United States Patent [19]

Bird et al.

[11] Patent Number: 5,482,966
[45] Date of Patent: Jan. 9, 1996

[54] OXIME DERIVATIVES

[75] Inventors: Thomas G. C. Bird, Witry-Les-Reims; Patrick Ple, Reims, both of France

[73] Assignees: Zeneca Limited, London, England; Zeneca Pharma S.A., Cergy Cedex, France

[21] Appl. No.: 240,464

[22] Filed: Jun. 13, 1994

Related U.S. Application Data

[62] Division of Ser. No. 14,564, Feb. 8, 1993, Pat. No. 5,332,757.

[30] Foreign Application Priority Data

Feb. 7, 1992 [EP] European Pat. Off. .............. 92400318
Oct. 9, 1992 [EP] European Pat. Off. .............. 92402764

[51] Int. Cl.$^6$ .................. A61K 31/35; A61K 31/34; C07D 309/10; C07D 307/20
[52] U.S. Cl. .................. 514/456; 514/471; 514/470; 514/459; 514/447; 514/444; 514/432; 514/380; 514/376; 514/372; 514/369; 514/336; 514/269; 544/298; 546/283; 546/268; 548/127; 548/129; 548/132; 548/135; 548/142; 548/144; 548/189; 548/213; 548/225; 548/243; 549/476; 549/475; 549/472; 549/419; 549/417; 549/416; 549/414; 549/467; 549/404; 549/60; 549/59; 549/57; 549/23
[58] Field of Search .................. 549/23, 57, 59, 549/60, 404, 414, 416, 417, 419, 467, 472, 475, 476; 514/456, 459, 470, 471, 432, 444, 447, 380, 376, 372, 369, 269, 336; 548/127, 129, 132, 135, 142, 144, 189, 213, 225, 243; 546/208, 283; 544/298

[56] References Cited

U.S. PATENT DOCUMENTS

| | | | |
|---|---|---|---|
| 4,567,184 | 1/1986 | Musser et al. | 514/277 |
| 4,625,034 | 11/1986 | Neiss et al. | 546/152 |
| 4,631,287 | 12/1986 | Chakraborty et al. | 514/307 |
| 4,661,596 | 4/1987 | Kreft, III et al. | 546/152 |
| 4,681,940 | 7/1987 | Musser et al. | 546/174 |
| 4,725,619 | 2/1988 | Chakraborty et al. | 514/442 |
| 4,728,668 | 3/1988 | Chakraborty et al. | 514/464 |
| 4,794,188 | 12/1988 | Musser et al. | 546/152 |
| 4,839,369 | 6/1989 | Youssefyeh et al. | 514/314 |
| 4,868,193 | 9/1989 | Lee | 514/314 |
| 4,874,769 | 10/1989 | Youssefyeh et al. | 514/314 |
| 4,876,346 | 10/1989 | Musser et al. | 546/172 |
| 5,006,534 | 4/1991 | Mohrs et al. | 514/311 |
| 5,098,930 | 3/1992 | Edwards et al. | 514/459 |
| 5,098,932 | 3/1992 | Hamon | 514/462 |
| 5,105,020 | 4/1992 | Girodeau | 568/633 |
| 5,134,148 | 7/1992 | Crawley et al. | 514/312 |
| 5,137,913 | 11/1992 | Bird et al. | 514/467 |
| 5,179,115 | 11/1993 | Bruneau et al. | 514/387 |
| 5,208,259 | 5/1993 | Bird et al. | 514/460 |

FOREIGN PATENT DOCUMENTS

| | | |
|---|---|---|
| 0110405 | 6/1984 | European Pat. Off. . |
| 0181568 | 5/1986 | European Pat. Off. . |
| 0190722 | 8/1986 | European Pat. Off. . |
| 0200101 | 12/1986 | European Pat. Off. . |

*Primary Examiner*—Nicky Chan
*Attorney, Agent, or Firm*—Cushman Darby & Cushman

[57] ABSTRACT

The invention concerns oxime derivatives of the formula I $$R^5O-N=C(R^4)-Ar^1-A^1-X^1-Ar^2-\underset{R^3}{\overset{OR^1}{\underset{|}{\overset{|}{C}}}}-R^2 \qquad I$$

wherein $R^4$ includes hydrogen, carboxy, carbamoyl, amino, cyano, trifluoromethyl, (1–4C)alkylamino, di-(1–4C)alkylamino and (1–4C)alkyl;

$R^5$ includes hydrogen, (1–4C)alkyl, (3–4C)alkenyl, (3–4C)alkynyl, (2–5C)alkanoyl, halogeno-(2–4C)alkyl and hydroxy-(2–4C)alkyl;

$Ar^1$ is phenylene or a heteroaryl diradical;

$A^1$ is a direct link to $X^1$, or $A^1$ is (1–4C)alkylene;

$X^1$ is oxy, thio, sulphinyl or sulphonyl;

$Ar^2$ is phenylene or a heteroaryl diradical;

$R^1$ is (1–4C)alkyl, (3–4C)alkenyl or (3–4C)alkynyl; and $R^2$ and $R^3$ together form a group of the formula —$A^2$—$X^2$—$A^3$— which together with the carbon atom to which $A^2$ and $A^3$ are attached define a ring having 5 or 6 ring atoms, wherein each of $A^2$ and $A^3$ is (1–3C)alkylene and $X^2$ is oxy, thio, sulphinyl, sulphonyl or imino;

or a pharmaceutically-acceptable salt thereof; processes for their manufacture; pharmaceutical compositions containing them and their use as 5-lipoxygenase inhibitors.

16 Claims, No Drawings

OXIME DERIVATIVES

This is a division of application Ser. No. 08/014,564, filed Feb. 8, 1993, U.S. Pat. No. 5,332,757.

This invention concerns oxime derivatives and more particularly oxime derivatives which are inhibitors of the enzyme 5-lipoxygenase (hereinafter referred to as 5-LO). The invention also concerns processes for the manufacture of said oxime derivatives and novel pharmaceutical compositions containing them. Also included in the invention is the use of said oxime derivatives in the treatment of various inflammatory and/or allergic diseases in which the direct or indirect products of 5-LO catalyzed oxidation of arachidonic acid are involved, and the production of new medicaments for such use.

As stated above the oxime derivatives described hereinafter are inhibitors of 5-LO, which enzyme is known to be involved in catalyzing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarized by G. W. Taylor and S. R. Clarke in *Trends in Pharmacological Sciences*, 1986, 7, 100–103. The leukotrienes and their metabolites have been implicated in the production and development of various inflammatory and allergic diseases such as inflammation of the joints (especially rheumatoid arthritis, osteoarthritis and gout), inflammation of the gastrointestinal tract (especially inflammatory bowel disease, ulcerative colitis and gastritis), skin disease (especially psoriasis, eczema and dermatitis) and respiratory disease (especially asthma, bronchitis and allergic rhinitis), and in the production and development of various cardiovascular and cerebrovascular disorders such as myocardial infarction, angina and peripheral vascular disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

It is disclosed in European Patent Application Nos. 0375404 A2 and 0385662 A2 that certain heterocyclic derivatives possess inhibitory properties against 5-LO. Furthermore European Patent Applications Nos. 0409413 and 0420511 are also concerned with heterocyclic derivatives which possess inhibitory properties against 5-LO. We have now discovered that certain oxime derivatives which possess some structural features which are similar to those of the compounds disclosed in the above-mentioned applications but which possess other structural features, in particular oxime groups, which were not envisaged in those earlier applications are effective inhibitors of the enzyme 5-LO and thus of leukotriene biosynthesis. Thus such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided an oxime derivative of the formula I

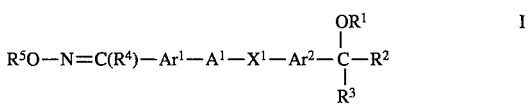

wherein $R^4$ is hydrogen, carboxy, carbamoyl, amino, cyano, trifluoromethyl, (1–4C)alkylamino, di-(1–4C)alkylamino, (1–4C)alkyl, (2–5C)alkanoyl, (1–4C)alkoxycarbonyl, N-(1–4C)alkylcarbamoyl, N,N-di-(1–4C)alkylcarbamoyl, (1–4C)alkylthio, (1–4C)alkylsulphinyl, (1–4C)alkylsulphonyl, phenyl, phenyl-(1–4C)alkyl or heteroaryl and wherein each phenyl or heteroaryl group may optionally bear one or two substituents selected from hydroxy, amino, halogeno, cyano, trifluoromethyl, (1–4C)alkyl, (1–4C)alkoxy, (1–4C)alkylamino, di-(1–4C)alkylamino, (1–4C)alkylthio, (1–4C)alkylsulphinyl and (1–4C)alkylsulphonyl;

$R^5$ is hydrogen, (1–4C)alkyl, (3–4C)alkenyl, (3–4C)alkynyl, (2–5C)alkanoyl, halogeno-(2–4C)alkyl, hydroxy-(2–4C)alkyl, (1–4C)alkoxy-(2–4C)alkyl, carbamoyl, N-(1–4C)alkylcarbamoyl, N,N-di-(1–4C)alkylcarbamoyl, amino-(2–4C)alkyl, (1–4C)alkylamino-(2–4C)alkyl, di-(1–4C)alkylamino-(2–4C)alkyl, (1–4C)alkylthio-(2–4C)alkyl, (1–4C)alkylsulphinyl-(2–4C)alkyl, (1–4C)alkylsulphonyl-(2–4C)alkyl, cyano-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-(1–4C)alkylcarbamoyl-(1–4C)alkyl, (2–5C)alkanoylamino-(2–4C)alkyl, phenyl-(1–4C)alkyl, heteroaryl-(1–4C)alkyl or heteroarylthio-(2–4C)alkyl and wherein each phenyl or heteroaryl group may optionally bear one or two substituents selected from halogeno, cyano, trifluoromethyl, carboxy, (1–4C)alkyl, (1–4C)alkoxy, (1–4C)alkoxycarbonyl, carboxy-(1–4C)alkyl and (1–4C)alkoxycarbonyl-(1–4C)alkyl;

$Ar^1$ is phenylene or a heteroaryl diradical which may optionally bear one or two substituents selected from halogeno, cyano, trifluoromethyl, hydroxy, amino, (1–4C)alkyl, (1–4C)alkoxy, phenyl-(1–4C)alkoxy, (1–4C)alkylamino and di-(1–4C)alkylamino;

or $R^4$ is linked to $Ar^1$ ortho to the $-N=C(R^4)-$ group and defines an ethylene, propylene, 1-methylpropylene or vinylene group, a group of the formula

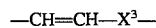

wherein $X^3$ is oxy or thio, or a group of the formula

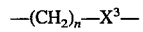

wherein n is 1 or 2, $X^3$ is oxy or thio, and one of the $-CH_2-$ groups may optionally be replaced by a $-CH(Me)-$ or $-C(Me)_2-$ group;

$A^1$ is a direct link to $X^1$, or $A^1$ is (1–4C)alkylene;

$X^1$ is oxy, thio, sulphinyl or sulphonyl;

$Ar^2$ is phenylene, pyridinediyl, pyrimidinediyl, thiophenediyl, furandiyl, thiazolediyl, oxazolediyl, thiadiazolediyl or oxadiazolediyl which may optionally bear one or two substituents selected from halogeno, cyano, trifluoromethyl, hydroxy, amino, (1–4C)alkyl, (1–4C)alkoxy, (1–4C)alkylamino and di-(1–4C)alkylamino;

$R^1$ is (1–4C)alkyl, (3–4C)alkenyl or (3–4C)alkynyl; and $R^2$ and $R^3$ together form a group of the formula —$A^2$—$X^2$—$A^3$— which together with the carbon atom to which $A^2$ and $A^3$ are attached define a ring having 5 or 6 ring atoms, wherein each of $A^2$ and $A^3$ is independently (1–3C)alkylene and $X^2$ is oxy, thio, sulphinyl, sulphonyl or imino, and which ring may optionally bear one or two substituents selected from hydroxy, (1–4C)alkyl and (1–4C)alkoxy;

or wherein $R^1$ and $R^2$ together form a group of the formula —$A^2$—$X^2$—$A^3$— which together with the oxygen atom to which $A^2$ is attached and with the carbon atom to which $A^3$ is attached define a ring having 5 or 6 ring atoms, wherein $A^2$ and $A^3$ which may be the same or different each is (1–3C)alkylene and $X^2$ is oxy, thio, sulphinyl or sulphonyl and which ring may bear one, two or three (1–4C)alkyl or (3–6C)cycloalkyl substituents, and wherein $R^3$ is (1–4C)alkyl, (2–4C)alkenyl or (2–4C)alkynyl;

or a pharmaceutically-acceptable salt thereof.

According to a further aspect of the invention there is provided an oxime derivative of the formula I as defined hereinbefore wherein $R^4$ and $R^5$ may in addition have one of the following meanings:

$R^4$ may in addition be hydroxy-(1–4C)alkyl, (1–4C)alkoxy-(1–4C)alkyl or (1–4C)alkylthio-(1–4C)alkyl, $R^5$ may in addition be (2–5C)alkanoyl-(1–4C)alkyl, and $R^4$ may in addition be linked to $Ar^1$ ortho to the —N=C($R^4$)— group to define a group of the formula —(CH$_2$)$_n$—$X^3$— wherein n is 1 or 2, $X^3$ is sulphinyl, sulphonyl, imino or (1–4C)alkylimino, and one of the —CH$_2$— groups may optionally be replaced by a —CH(Me)— or —C(Me)$_2$— group;

or a pharmaceutically-acceptable salt thereof.

In a further aspect of the invention there is provided an oxime derivative of the formula I wherein $R^4$ is hydrogen, carboxy, carbamoyl, (1–4C)alkyl, (2–5C)alkanoyl, (1–4C)alkoxycarbonyl, N-(1–4C)alkylcarbamoyl, N,N-di-(1–4C)alkylcarbamoyl, phenyl, phenyl-(1–4C)alkyl or heteroaryl and wherein each phenyl or heteroaryl group may optionally bear one or two substituents selected from hydroxy, amino, halogeno, cyano, trifluoromethyl, (1–4C)alkyl, (1–4C)alkoxy, (1–4C)alkylamino, di-(1–4C)alkylamino, (1–4C)alkylthio, (1–4C)alkylsulphinyl and (1–4C)alkylsulphonyl;

$R^5$ is hydrogen, (1–4C)alkyl, (2–5C)alkanoyl, halogeno-(2–4C)alkyl, hydroxy-(2–4C)alkyl, amino-(2–4C)alkyl, (1–4C)alkylamino-(2–4C)alkyl, di-(1–4C)alkylamino-(2–4C)alkyl, (1–4C)alkylthio-(2–4C)alkyl, (1–4C)alkylsulphinyl-(2–4C)alkyl, (1–4C)alkylsulphonyl-(2–4C)alkyl, cyano-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-(1–4C)alkylcarbamoyl-(1–4C)alkyl, phenyl-(1–4C)alkyl, heteroaryl-(1–4C)alkyl or heteroarylthio-(2–4C)alkyl and wherein each phenyl or heteroaryl group may optionally bear one or two substituents selected from halogeno, cyano, trifluoromethyl, carboxy, (1–4C)alkyl, (1–4C)alkoxy, (1–4C)alkoxycarbonyl, carboxy-(1–4C)alkyl and (1–4C)alkoxycarbonyl-(1–4C)alkyl;

$Ar^1$ is phenylene or a heteroaryl diradical which may optionally bear one or two substituents selected from halogeno, cyano, trifluoromethyl, hydroxy, amino, (1–4C)alkyl, (1–4C)alkoxy, (1–4C)alkylamino and di-(1–4C)alkylamino;

or $R^4$ is an ethylene, propylene, 1-methylpropylene or vinylene group linked to $Ar^1$ ortho to the —N=C($R^4$)— group;

$A^1$ is a direct link to $X^1$, or $A^1$ is (1–4C)alkylene;

$X^1$ is oxy, thio, sulphinyl or sulphonyl;

$Ar^2$ is phenylene, pyridinediyl, pyrimidinediyl, thiophenediyl or furandiyl which may optionally bear one or two substituents selected from halogeno, cyano, trifluoromethyl, hydroxy, amino, (1–4C)alkyl, (1–4C)alkoxy, (1–4C)alkylamino and di-(1–4C)alkylamino;

$R^1$ is (1–4C)alkyl, (3–4C)alkenyl or (3–4C)alkynyl; and $R^2$ and $R^3$ together form a group of the formula —$A^2$—$X^2$—$A^3$— which together with the carbon atom to which $A^2$ and $A^3$ are attached define a ring having 5 or 6 ring atoms, wherein each of $A^2$ and $A^3$ is independently (1–3C)alkylene and $X^2$ is oxy, thio, sulphinyl, sulphonyl or imino, and which ring may optionally bear one or two substituents selected from hydroxy, (1–4C)alkyl and (1–4C)alkoxy;

or a pharmaceutically-acceptable salt thereof.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of the formula I defined above may exhibit the phenomenon of tautomerism and any formula drawing presented herein may represent only one of the possible tautomeric forms, the invention includes in its definition any tautomeric form of a compound of the formula I which possesses the property of inhibiting 5-LO and is not to be limited merely to any one tautomeric form utilized within the formulae drawings.

It is further to be understood that, insofar as it is well known that oxime derivatives may exist in different geometric isomeric forms, commonly designated as (E)- or (Z)-isomers, the invention includes in its definition any such geometric isomeric form which possesses the property of inhibiting 5-LO. The separation of such geometric isomeric forms may be possible by the standard laboratory techniques of organic chemistry such as by chromatographic separation of a mixture of said isomeric forms or by crystallization of one such isomeric form from a mixture thereof. Examples of such techniques are set out in the accompanying Examples which are set out hereinafter.

It is further to be understood that, insofar as certain of the compounds of formula I defined above may exist in optically active or racemic forms by virtue of one or more asymmetric carbon atoms, the invention includes in its definition any such optically active or racemic form which possesses the property of inhibiting 5-LO. The synthesis of optically active forms may be carried out by standard techniques of organic chemistry well known in the art, for example by synthesis from optically active starting materials or by resolution of a racemic form.

Suitable values for the generic terms referred to above include those set out below.

A suitable value for $R^4$ or $R^5$ when it is (1–4C)alkyl, or for the (1–4C)alkyl group when $X^3$ is (1–4C)alkylimino, is, for example, methyl, ethyl, propyl, isopropyl or butyl; when $R^4$ or $R^5$ is (2–5C)alkanoyl is, for example, acetyl, propionyl, butyryl or pivaloyl; and when $R^4$ or $R^5$ is phenyl-(1–4C)alkyl is, for example, benzyl, phenethyl or 3-phenylpropyl.

A suitable value for $R^4$ when it is (1–4C)alkoxycarbonyl is, for example, methoxycarbonyl, ethoxycarbonyl, propoxycarbonyl or tert-butoxycarbonyl; when it is N-(1–4C)alkylcarbamoyl is, for example, N-methylcarbamoyl, N-ethylcarbamoyl or N-propylcarbamoyl; and when it is N,N-di-(1–4C)alkylcarbamoyl is, for example, N,N-dimethylcarbamoyl, N-ethyl-N-methylcarbamoyl or N,N-dipropylcarbamoyl.

A suitable value for $R^4$ when it is (1–4C)alkylamino is, for example, methylamino, ethylamino, propylamino or isopropylamino; when it is di-(1–4C)alkylamino is, for example, dimethylamino, diethylamino or N-ethyl-N-methylamino; when it is (1–4C)alkylthio is, for example, methylthio, ethylthio or propylthio; when it is (1–4C)alkylsulphinyl is, for example, methylsulphinyl, ethylsulphinyl or propylsulphinyl; when it is (1–4C)alkylsulphonyl is, for example, methylsulphonyl, ethylsulphonyl or propylsulphonyl; when it is hydroxy-(1–4C)alkyl is, for example, hydroxymethyl, 1-hydroxyethyl, 2-hydroxyethyl or 3-hydroxypropyl; when it is (1–4C)alkoxy-(1–4C)alkyl is, for example, methoxymethyl, ethoxymethyl, 1-methoxyethyl, 1-ethoxyethyl, 2-methoxyethyl or 2-ethoxyethyl; and when it is (1–4C)alkylthio-(1–4C)alkyl is, for example, methylthiomethyl, ethylthiomethyl, 1-methylthioethyl or 2-methylthioethyl.

A suitable value for $R^4$ when it is heteroaryl, or for the heteroaryl group in $R^5$ when $R^5$ is heteroaryl-(1–4C)alkyl or heteroarylthio-(2–4C)alkyl, is for example, a 5-membered or 6-membered heterocyclic moiety containing up to four nitrogen heteroatoms and optionally containing a further heteroatom selected from oxygen and sulphur such as pyrrolyl, pyrazolyl, imidazolyl, oxazolyl, isoxazolyl, thiazolyl, isothiazolyl, 1,2,3-triazolyl, 1,2,4-triazolyl, oxadiazolyl, thiadiazolyl, tetrazolyl, pyridyl, pyrazinyl, pyrimidinyl and pyridazinyl which may be attached through any available position including through any available nitrogen atom.

A suitable value for the (1–4C)alkyl group when $R^5$ is heteroaryl-(1–4C)alkyl is, for example, methyl, ethyl, propyl, isopropyl or butyl. A suitable value for the (2–4C)alkyl group when $R^5$ is heteroarylthio-(2–4C)alkyl is, for example, ethyl, propyl, isopropyl or butyl.

A convenient value for $R^4$ when it is heteroaryl is, for example, a 5-membered heterocyclic moiety containing 1 or 2 nitrogen heteroatoms and optionally containing a further heteroatom selected from oxygen and sulphur such as pyrazolyl, imidazolyl, oxazolyl, thiazolyl, oxadiazolyl or thiadiazolyl.

A convenient value for the heteroaryl group in $R^5$ when $R^5$ is heteroaryl-(1–4C)alkyl or heteroarylthio-(2–4C)alkyl is, for example, a 5-membered heterocyclic moiety containing up to four nitrogen heteroatoms and optionally containing a further heteroatom selected from oxygen and sulphur such as imidazolyl, oxazolyl, thiazolyl, isoxazolyl, isothiazolyl, 1,2,4-triazolyl, oxadiazolyl, thiadiazolyl or tetrazolyl.

A further convenient value for the heteroaryl group in $R^5$ when $R^5$ is heteroaryl-(1–4C)alkyl is, for example, a 6-membered heterocyclic moiety containing 1 or 2 nitrogen heteroatoms such as pyridyl, pyrazinyl, pyrimidinyl and pyridazinyl.

Suitable values for substituents which may be present when $R^4$ or $R^5$ is phenyl, phenyl-(1–4C)alkyl, heteroaryl, heteroaryl-(1–4C)alkyl or heteroarylthio-(2–4C)alkyl, or for substituents on $Ar^1$ or $Ar^2$, include, for example:

for halogeno: fluoro, chloro and bromo;

for (1–4C)alkyl: methyl, ethyl, propyl and isopropyl;

for (1–4C)alkoxy: methoxy, ethoxy, propoxy and isopropoxy;

for (1–4C)alkoxycarbonyl: methoxycarbonyl, ethoxycarbonyl, propoxycarbonyl and tert-butoxycarbonyl;

for carboxy-(1–4C)alkyl: carboxymethyl, 1-carboxyethyl, 2-carboxyethyl, 2-carboxyprop-2-yl and 3-carboxypropyl;

for (1–4C)alkoxycarbonyl-(1–4C)alkyl: methoxycarbonylmethyl, ethoxycarbonylmethyl, 1-methoxycarbonylethyl, 1-ethoxycarbonylethyl, 2-methoxycarbonylethyl, 2-ethoxycarbonylethyl, 2-methoxycarbonylprop-2-yl, 3-ethoxycarbonylprop-2-yl, 3-methoxycarbonylpropyl and 3-ethoxycarbonylpropyl;

for (1–4C)alkylamino: methylamino, ethylamino and propylamino;

for di-(1–4C)alkylamino: dimethylamino, diethylamino and N-ethyl-N-methylamino;

for (1–4C)alkylthio: methylthio, ethylthio and propylthio;

for (1–4C)alkylsulphinyl: methylsulphinyl, ethylsulphinyl and propylsulphinyl;

for (1–4C)alkylsulphonyl: methylsulphonyl, ethylsulphonyl and propylsulphonyl;

for phenyl-(1–4C)alkoxy: benzyloxy and 2-phenylethoxy.

A suitable value for $R^5$ when it is (3–4C)alkenyl is, for example, allyl, 2-butenyl or 3-butenyl; when it is (3–4C)alkynyl is, for example, 2-propynyl or 2-butynyl; when it is halogeno-(2–4C)alkyl is, for example, 2-fluoroethyl, 2-chloroethyl, 2-bromoethyl, 3-fluoropropyl or 3-chloropropyl; when it is hydroxy-(2–4C)alkyl is, for example, 2-hydroxyethyl or 3-hydroxypropyl; when it is (1–4C)alkoxy-(2–4C)alkyl is, for example, 2-methoxyethyl, 2-ethoxyethyl or 3-methoxypropyl; when it is N-(1–4C)alkylcarbamoyl is, for example, N-methylcarbamoyl or N-ethylcarbamoyl; when it is N,N-di-(1–4C)alkylcarbamoyl is, for example, N,N-dimethylcarbamoyl or N,N-diethylcarbamoyl; when it is amino-(2–4C)alkyl is, for example, 2-aminoethyl or 3-aminopropyl; when it is (1–4C)alkylamino-(2–4C)alkyl is, for example, 2-methylaminoethyl, 2-ethylaminoethyl, 2-propylaminoethyl, 3-methylaminopropyl or 3-ethylaminopropyl; when it is di-(1–4C)alkylamino-(2–4C)alkyl is, for example, 2-dimethylaminoethyl, 2-diethylaminoethyl, 3-dimethylaminopropyl or 3-diethylaminopropyl; when it is (1–4C)alkylthio-(2–4C)alkyl is, for example, 2-methylthioethyl, 2-ethylthioethyl, 3-methylthiopropyl or 3-ethylthiopropyl; when it is (1–4C)alkylsulphinyl-(2–4C)alkyl is, for example, 2-methylsulphinylethyl, 2-ethylsulphinylethyl, 3-methylsulphinylpropyl or 3-ethylsulphinylpropyl; when it is (1–4C)alkylsulphonyl-(2–4C)alkyl is, for example, 2-methylsulphonylethyl, 2-ethylsulphonylethyl, 3-methysulphonylpropyl or 3-ethylsulphonylpropyl; when it is cyano-(1–4C)alkyl is, for example, cyanomethyl, 1-cyanoethyl, 2-cyanoethyl, 2-cyanoprop-2-yl or 3-cyanopropyl; when it carboxy-(1–4C)alkyl is, for example, carboxymethyl, 1-carboxyethyl, 2-carboxyethyl, 2-carboxyprop-2-yl or 3-carboxypropyl; when it is (1–4C)alkoxycarbonyl-(1–4C)alkyl is, for example, methoxycarbonylmethyl, ethoxycarbonylmethyl, propoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 2-methoxycarbonylprop-2-yl, 2-ethoxycarbonylprop-2-yl, 3-methoxycarbonylpropyl or 3-ethoxycarbonylpropyl; when it is carbamoyl-(1–4C)alkyl is, for example, carbamoylmethyl, 1-carbamoylethyl, 2-carbamoylethyl, 2-carbamoylprop-2-yl or 3-carbamoylpropyl; when it is N-(1–4C)alkylcarbamoyl-(1–4C)alkyl is, for example, N-methylcarbamoylmethyl, N-ethylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl, 2-(N-methylcarbamoyl)prop-2-yl, 2-(N-ethylcarbamoyl)prop-2-yl, 3-(N-methylcarbamoyl)propyl or 3-(N-ethylcarbamoyl)propyl; when it is N,N-di-(1–4C)alkylcarbamoyl-(1–4C)alkyl is, for example, N,N-dimethylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl, 2-(N,N-dimethylcarbamoyl)prop-2-yl, 2-(N,N-diethylcarbamoyl)prop-2-yl, 3-(N,N-dimethylcarbamoyl)propyl or 3-(N,N-diethylcarbamoyl)propyl; when it is (2–5C)alkanoylamino-(2–4C)alkyl is, for example, 2-acetamidoethyl, 2-propionamidoethyl, 2-butyramidoethyl or 3-acetamidopropyl; and when it is (2–5C)alkanoyl-(1–4C)alkyl is, for example, acetonyl, propionylmethyl, 1-acetylethyl, 2-acetylethyl or 2-propionylethyl.

A suitable value for $Ar^1$ or $Ar^2$ when it is phenylene is, for example, 1,3- or 1,4-phenylene.

A suitable value for $Ar^1$ when it is a heteroaryl diradical is, for example, a 5-membered or 6-membered heteroaryl diradical containing one or two nitrogen heteroatoms and optionally containing a further heteroatom selected from oxygen and sulphur such as 2,4-, 2,5- or 3,5-pyridinediyl, 2,5- or 4,6-pyrimidinediyl, 2,5- or 2,6-pyrazinediyl, 3,5- or 3,6-pyridazinediyl, 2,4- or 2,5-imidazolediyl, 2,4- or 2,5-oxazolediyl, 2,4- or 2,5-thiazolediyl, 1,2,4-triazole-3,5-diyl, 2,5-oxadiazolediyl or 2,5-thiadiazolediyl.

A suitable value for $A^1$ when it is (1–4C)alkylene is, for example, methylene, ethylene or trimethylene.

A suitable value for $Ar^2$ when it is pyridinediyl, pyrimidinediyl, thiophenediyl, furandiyl, thiazolediyl, oxazolediyl, thiadiazolediyl or oxadiazolediyl is, for example, 2,4-, 2,5- or 3,5-pyridinediyl, 4,6-pyrimidinediyl, 2,4- or 2,5-thiophenediyl, 2,4- or 2,5-furandiyl, 2,4- or 2,5-thiazolediyl, 2,4- or 2,5-oxazolediyl, 2,5-thiadiazolediyl or 2,5-oxadiazolediyl.

A suitable value for $R^1$ when it is (1–4C)alkyl is, for example, methyl, ethyl, propyl or butyl; when it (3–4C)alkenyl is, for example allyl, 2-butenyl or 3-butenyl; and when it is (3–4C)alkynyl is, for example, 2-propynyl or 2-butynyl.

When $R^2$ and $R^3$ together form a group of the formula —$A^2$—$X^2$—$A^3$— which together with the carbon atom to which $A^2$ and $A^3$ are attached define a ring having 5 or 6 ring atoms then a suitable value for $A^2$ or $A^3$, which may be the same or different when each is (1–3C)alkylene is, for example, methylene, ethylene or trimethylene. Suitable values for the substituents which may be present on said 5- or 6-membered ring include, for example:

for (1–4C)alkyl: methyl, ethyl, propyl, isopropyl, butyl and isobutyl;

for (1–4C)alkoxy: methoxy, ethoxy, propoxy, isopropoxy and butoxy.

Said substituents may be located on any available position including, when the substituent is (1–4C)alkyl, on the nitrogen atom when $X^2$ is imino.

When $R^1$ and $R^2$ together form a group of the formula —$A^2$—$X^2$—$A^3$— which together with the oxygen atom to which $A^2$ is attached and with the carbon atom to which $A^3$ is attached define a ring having 5 or 6 ring atoms then a suitable value for $A^2$ and $A^3$, which may be the same or different, when each is (1–3C)alkylene is, for example, methylene, ethylene or trimethylene. Suitable values for the (1–4C)alkyl substituents which may be present on said 5- or 6-membered ring include, for example, methyl, ethyl, propyl, isopropyl and butyl; and suitable values for the (3–6C)cycloalkyl substituents which may be present include, for example, cyclopropyl, cyclobutyl, cyclopentyl and cyclohexyl.

A suitable value for $R^3$ when it is (1–4C)alkyl is, for example, methyl, ethyl, propyl or butyl; when it is (2–4C)alkenyl is, for example, vinyl, allyl, 2-butenyl or 3-butenyl; and when it is (2–4C)alkynyl is, for example, ethynyl, 2-propynyl or 2-butynyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular compounds of the invention include, for example, oxime derivatives of the formula I, or pharmaceutically-acceptable salts thereof, wherein:

(a) $R^4$ is hydrogen, (1–4C)alkyl, (1–4C)alkoxycarbonyl or phenyl and wherein said phenyl group may optionally bear one or two substituents selected from hydroxy, amino, halogeno, (1–4C)alkyl, (1–4C)alkoxy, (1–4C)alkylamino and di-(1–4C)alkylamino; and $R^5$, $Ar^1$, $A^1$, $X^1$, $Ar^2$, $R^1$, $R^2$ and $R^3$ have any of the meanings defined hereinbefore or in this section defining particular compounds;

(b) $R^4$ is hydrogen, cyano, trifluoromethyl, di-(1–4C)alkylamino, (1–4C)alkyl, (2–5C)alkanoyl, (1–4C)alkoxycarbonyl, (1–4C)alkylthio or phenyl; and $R^5$, $Ar^1$, $A^1$, $X^1$, $Ar^2$, $R^1$, $R^2$ and $R^3$ have any of the meanings defined hereinbefore or in this section defining particular compounds;

(c) $R^4$ is hydrogen, cyano, trifluoromethyl, di-(1–4C)alkylamino, (1–4C)alkyl, (2–5C)alkanoyl, (1–4C)alkoxycarbonyl, (1–4C)alkylthio, phenyl, hydroxy-(1–4C)alkyl, (1–4C)alkoxy-(1–4C)alkyl or (1–4C)alkylthio-(1–4C)alkyl; and $R^5$, $Ar^1$, $A^1$, $X^1$, $Ar^2$, $R^1$, $R^2$ and $R^3$ have any of the meanings defined hereinbefore or in this section defining particular compounds;

(d) $R^4$ is heteroaryl (especially thiazolyl); and $R^5$, $Ar^1$, $A^1$, $X^1$, $Ar^2$, $R^1$, $R^2$ and $R^3$ have any of the meanings defined hereinbefore or in this section defining particular compounds;

(e) $R^5$ is hydrogen, (1–4C)alkyl, (2–5C)alkanoyl, halogeno-(2–4C)alkyl, cyano-(1–4C)alkyl, (1–4C)alkoxycarbonyl-(1–4C)alkyl or phenyl-(1–4C)alkyl and wherein said phenyl-(1–4C)alkyl group may optionally bear one or two substituents selected from halogeno, (1–4C)alkyl and (1–4C)alkoxy; and $R^4$, $Ar^1$, $A^1$, $X^1$, $Ar^2$, $R^1$, $R^2$ and $R^3$ have any of the meanings defined hereinbefore or in this section defining particular compounds;

(f) $R^5$ is hydrogen, (1–4C)alkyl, (3–4C)alkenyl, (3–4C)alkynyl, (2–5C)alkanoyl, halogeno-(2–4C)alkyl, hydroxy-(2–4C)alkyl, (1–4C)alkylthio-(2–4C)alkyl, cyano-(1–4C)alkyl, carboxy-(1–4C)alkyl or (1–4C)alkoxycarbonyl-(1–4C)alkyl; and $R^4$, $Ar^1$, $A^1$, $X^1$, $Ar^2$, $R^1$, $R^2$ and $R^3$ have any of the meanings defined hereinbefore or in this section defining particular compounds;

(g) $R^5$ is hydrogen, (1–4C)alkyl, (3–4C)alkenyl, (3–4C)alkynyl, (2–5C)alkanoyl, halogeno-(2–4C)alkyl, hydroxy-(2–4C)alkyl, (1–4C)alkoxy-(2–4C)alkyl, (1–4C)alkylthio-(2–4C)alkyl, cyano-(1–4C)alkyl, carboxy-(1–4C)alkyl, (1–4C)alkoxycarbonyl-(1–4C)alkyl, phenyl-(1–4C)alkyl or (2–5C)alkanoyl-(1–4C)alkyl; and $R^4$, $Ar^1$, $A^1$, $X^1$, $Ar^2$, $R^1$, $R^2$ and $R^3$ have any of the meanings defined hereinbefore or in this section defining particular compounds;

(h) $R^5$ is heteroaryl-(1–4C)alkyl (especially imidazolyl- or thiazolyl-(1–4C)alkyl) or heteroarylthio-(2–4C)alkyl (especially thiadiazolythio- or tetrazolylthio-(2–4C)alkyl) and wherein each heteroaryl group may optionally bear one or two substituents selected from halogeno, (1–4C)alkyl, (1–4C)alkoxycarbonyl and (1–4C)alkoxycarbonyl-(1–4C)alkyl; and $R^4$, $Ar^1$, $A^1$, $X^1$, $Ar^2$, $R^1$, $R^2$ and $R^3$ have any of the meanings defined hereinbefore or in this section defining particular compounds;

(i) $R^5$ is heteroaryl-(1–4C)alkyl (especially pyridyl-(1–4C)alkyl); and $R^4$, $Ar^1$, $A^1$, $X^1$, $Ar^2$, $R^1$, $R^2$ and $R^3$ have any of the meanings defined hereinbefore or in this section defining particular compounds;

(j) $Ar^1$ is phenylene which may optionally bear one or two substituents selected from halogeno, (1–4C)alkyl and (1–4C)alkoxy; and $R^4$, $R^5$, $A^1$, $X^1$, $Ar^2$, $R^1$, $R^2$ and $R^3$ have any of the meanings defined hereinbefore or in this section defining particular compounds;

(k) $Ar^1$ is 1,3- or 1,4-phenylene which may optionally bear a substituent selected from halogeno, hydroxy, (1–4C)alkyl, (1–4C)alkoxy and phenyl-(1–4C)alkoxy; and $R^4$, $R^5$, $A^1$, $X^1$, $Ar^2$, $R^1$, $R^2$ and $R^3$ have any of the meanings defined hereinbefore or in this section defining particular compounds;

(l) $Ar^1$ is a heteroaryl diradical (especially 2,4-, 2,5- or 3,5-pyridinediyl or 2,4- or 2,5 thiazolediyl); and $R^4$, $R^5$, $A^1$, $X^1$, $Ar^2$, $R^1$, $R^2$ and $R^3$ have any of the meanings defined hereinbefore or in this section defining particular compounds;

(m) $Ar^1$ is 2,5-pyridinediyl, 2,5-pyrazinediyl or 3,6-pyridazinediyl; and $R^4$, $R^5$, $A^1$, $X^1$, $Ar^2$, $R^1$, $R^2$ and $R^3$ have any of the meanings defined hereinbefore or in this section defining particular compounds;

(n) $Ar^1$ is phenylene and $R^4$ is an ethylene group linked to $Ar^1$ at the position ortho to the —N=C($R^4$)— group; and $R^5$, $A^1$, $X^1$, $Ar^2$, $R^1$, $R^2$ and $R^3$ have any of the meanings defined hereinbefore or in this section defining particular compounds;

(o) $Ar^1$ is 1,4-phenylene and $R^4$ is linked to $Ar^1$ ortho to the —N=C($R^4$)— group and defines an ethylene or vinylene group, or a group of the formula —(CH$_2$)$_n$—X$^3$— wherein n is 2 and $X^3$ is oxy; and $R^5$, $A^1$, $X^1$, $Ar^2$, $R^1$, $R^2$ and $R^3$ have any of the meanings defined hereinbefore or in this section defining particular compounds;

(p) $A^1$ is a direct link to $X^1$; $R^4$, $R^5$, $Ar^1$, $X^1$, $Ar^2$, $R^1$, $R^2$ and $R^3$ have any of the meanings defined hereinbefore or in this section defining particular compounds;

(q) $A^1$ is (1–4C)alkylene and $X^1$ is oxy; and $R^4$, $R^5$, $Ar^1$, $Ar^2$, $R^1$, $R^2$ and $R^3$ have any of the meanings defined hereinbefore or in this section defining particular compounds;

(r) $A^1$ is a direct link to $X^1$ and $X^1$ is thio; and $R^4$, $R^5$, $Ar^1$, $Ar^2$, $R^1$, $R^2$ and $R^3$ have any of the meanings defined hereinbefore or in this section defining particular compounds;

(s) $Ar^2$ is phenylene which may optionally bear one or two substituents selected from halogeno, trifluoromethyl, amino, (1–4C)alkyl and (1–4C)alkoxy, or $Ar^2$ is pyridinediyl or thiophenediyl; and $R^4$, $R^5$, $Ar^1$, $A^1$, $X^1$, $R^1$, $R^2$ and $R^3$ have any of the meanings defined hereinbefore or in this section defining particular compounds;

(t) $Ar^2$ is 1,3-phenylene which may optionally bear one or two halogeno substituents; and $R^4$, $R^5$, $Ar^1$, $A^1$, $X^1$, $R^1$, $R^2$ and $R^3$ have any of the meanings defined hereinbefore or in this section defining particular compounds;

(u) $Ar^2$ is pyrimidinediyl which may optionally bear one amino substituent or $Ar^2$ is thiophenediyl or thiazolediyl; and $R^4$, $R^5$, $Ar^1$, $A^1$, $X^1$, $R^1$, $R^2$ and $R^3$ have any of the meanings defined hereinbefore or in this section defining particular compounds;

(v) $R^1$ is (1–4C)alkyl; and $R^4$, $R^5$, $Ar^1$, $A^1$, $X^1$, $Ar^2$, $R^2$ and $R^3$ have any of the meanings defined hereinbefore or in this section defining particular compounds;

(w) $R^2$ and $R^3$ together form a group of the formula —$A^2$—$X^2$—$A^3$— which together with the carbon atom to which $A^2$ and $A^3$ are attached define a ring having 5 or 6 ring atoms, wherein each of $A^2$ and $A^3$ is independently (1–3C)alkylene and $X^2$ is oxy, and which ring may optionally bear one or two (1–4C)alkyl substituents; and $R^4$, $R^5$, $Ar^1$, $A^1$, $X^1$, $Ar^2$ and $R^1$ have any of the meanings defined hereinbefore or in this section defining particular compounds; or (x) $R^1$ and $R^2$ together form a group of the formula —$A^2$—$X^2$—$A^3$— which together with the oxygen atom to which $A^2$ is attached and with the carbon atom to which $A^3$ is attached define a ring having 5 ring atoms, wherein each of $A^2$ and $A^3$ is methylene and $X^2$ is oxy, and which ring may optionally bear one or two substituents selected from methyl, ethyl and cyclopropyl, and $R^3$ is methyl or ethyl; and $R^4$, $R^5$, $Ar^1$, $A^1$, $X^1$ and $Ar^2$ have any of the meanings defined hereinbefore or in this section defining particular compounds;

A preferred compound of the invention comprises an oxime derivative of the formula I wherein $R^4$ is hydrogen, methyl, ethyl, propyl, methoxycarbonyl, ethoxycarbonyl, propoxycarbonyl or phenyl and wherein said phenyl group may optionally bear one substituent selected from fluoro, chloro, methyl and methoxy;

$R^5$ is hydrogen, methyl, ethyl, propyl, 2-fluoroethyl, 2-chloroethyl, cyanomethyl, methoxycarbonylmethyl or ethoxycarbonylmethyl;

$Ar^1$ is 1,4-phenylene which may optionally bear one substituent selected from fluoro, chloro, methyl and methoxy;

$A^1$ is a direct link to $X^1$ and $X^1$ is thio, or $A^1$ is methylene and $X^1$ is oxy;

$Ar^2$ is 1,3- or 1,4-phenylene which may optionally bear one or two substituents selected from fluoro, chloro, trifluoromethyl, amino, methyl and methoxy, or $Ar^2$ is 3,5-pyridinediyl, 2,4-thiophenediyl or 2,5-thiophenediyl;

$R^1$ is methyl, ethyl or allyl; and $R^2$ and $R^3$ together form a group of the formula $—A^2—X^2—A^3—$ which together with the carbon atom to which $A^2$ and $A^3$ are attached define a ring having 6 ring atoms, wherein each of $A^2$ and $A^3$ is ethylene and $X^2$ is oxy, and which ring may optionally bear one or two substituents selected from methyl and ethyl;

or a pharmaceutically-acceptable salt thereof.

A further preferred compound of the invention comprises an oxime derivative of the formula I wherein $R^4$ is hydrogen, cyano, trifluoromethyl, dimethylamino, methyl, ethyl, propyl, isopropyl, acetyl, methoxycarbonyl, ethoxycarbonyl, methylthio, phenyl, hydroxymethyl, methoxymethyl or methylthiomethyl;

$R^5$ is hydrogen, methyl, ethyl, propyl, isopropyl, allyl, prop-2-ynyl, acetyl, propionyl, butyryl, pivaloyl, 2-fluoroethyl, 2-hydroxyethyl, 2-methoxyethyl, 2-methylthioethyl, cyanomethyl, carboxymethyl, methoxycarbonylmethyl, ethoxycarbonylmethyl, benzyl, acetonyl or 2-, 3- or 4-pyridylmethyl;

$Ar^1$ is 1,4-phenylene which may optionally bear one substituent selected from fluoro, chloro, hydroxy, methyl, methoxy and benzyloxy, or $Ar^1$ is 2,5-pyridinediyl, or $Ar^1$ is 1,4-phenylene and $R^4$ is linked to $Ar^1$ ortho to the $—N{=}C(R^4)—$ group and defines an ethylene or vinylene group, or a group of the formula $—CH_2CH_2O—$;

$A^1$ is a direct link to $X^1$ and $X^1$ is thio or sulphonyl, or $A^1$ is methylene and $X^1$ is oxy;

$Ar^2$ is 1,3-phenylene which may optionally bear one or two fluoro substituents or $Ar^2$ is 3,5-pyridinediyl, 2-amino-4,6-pyrimidinediyl, 2,4- or 2,5-thiophenediyl or 2,4- or 2,5-thiazolediyl;

$R^1$ is methyl, ethyl or allyl;

and $R^2$ and $R^3$ together form a group of the formula $—A^2—X^2—A^3—$ which together with the carbon atom to which $A^2$ and $A^3$ are attached define a ring having 5 or 6 ring atoms, wherein $A^2$ is methylene or ethylene, $A^3$ is ethylene and $X^2$ is oxy, and which ring may optionally bear one or two substituents selected from methyl and ethyl;

or $R^1$ and $R^2$ together form a group of the formula $—A^2—X^2—A^3—$ which together with the oxygen atom to which $A^2$ is attached and the carbon atom to which $A^3$ is attached define a ring having 5 ring atoms wherein each of $A^2$ and $A^3$ is methylene and $X^2$ is oxy, and which ring may optionally bear one or two substituents selected from methyl and ethyl, and $R^3$ is methyl or ethyl;

or a pharmaceutically-acceptable salt thereof.

A further preferred compound of the invention comprises an oxime derivative of the formula I wherein $R^4$ is hydrogen, cyano, trifluoromethyl, dimethylamino, methyl, ethyl, propyl, isopropyl, acetyl, methoxycarbonyl, ethoxycarbonyl, methylthio or phenyl;

$R^5$ is hydrogen, methyl, ethyl, propyl, isopropyl, allyl, prop-2-ynyl, acetyl, propionyl, butyryl, pivaloyl, 2-fluoroethyl, 2-hydroxyethyl, 2-methoxyethyl, 2-methylthioethyl, cyanomethyl, carboxymethyl, methoxycarbonylmethyl, ethoxycarbonylmethyl or 2-, 3- or 4-pyridylmethyl;

$Ar^1$ is 1,4-phenylene which may optionally bear one substituent selected from fluoro, chloro, hydroxy, methyl, methoxy and benzyloxy;

or $Ar^1$ is 1,4-phenylene and $R^4$ is linked to $Ar^1$ ortho to the $—N{=}C(R^4)—$ group and defines an ethylene vinylene group, or a group of the formula $—CH_2CH_2O—$;

$A^1$ is a direct link to $X^1$ and $X^1$ is thio or sulphonyl, or $A^1$ is methylene and $X^1$ is oxy;

$Ar^2$ is 1,3-phenylene which may optionally bear one or two fluoro substituents, or $Ar^2$ is 3,5-pyridinediyl, 2-amino-4,6-pyrimidinediyl, 2,4- or 2,5-thiophenediyl or 2,4- or 2,5-thiazolediyl;

$R^1$ is methyl, ethyl or allyl;

and $R^2$ and $R^3$ together form a group of the formula $—A^2—X^2—A^3—$ which together with the carbon atom to which $A^2$ and $A^3$ are attached define a ring having 5 or 6 ring atoms, wherein $A^2$ is methylene or ethylene, $A^3$ is ethylene and $X^2$ is oxy, and which ring may optionally bear one or two substituents selected from methyl and ethyl;

or $R^1$ and $R^2$ together form a group of the formula $—A^2—X^2—A^3—$ which together with the oxygen atom to which $A^2$ is attached and the carbon atom to which $A^3$ is attached define a ring having 5 ring atoms wherein each of $A^2$ and $A^3$ is methylene and $X^2$ is oxy, and which ring may optionally bear one or two substituents selected from methyl and ethyl, and $R^3$ is methyl or ethyl;

or a pharmaceutically-acceptable salt thereof.

A further preferred compound of the invention comprises an oxime derivative of the formula I wherein $R^4$ is hydrogen, methyl, ethyl, methoxycarbonyl, ethoxycarbonyl or phenyl;

$R^5$ is hydrogen, methyl, ethyl, 2-fluoroethyl, cyanomethyl, methoxycarbonylmethyl or ethoxycarbonylmethyl;

$Ar^1$ is 1,4-phenylene;

$A^1$ is a direct link to $X^1$;

$X^1$ is thio;

$Ar^2$ is 1,3-phenylene which may optionally bear one or two substituents selected from fluoro and chloro, or $Ar^2$ is 2,4- or 2,5-thiophenediyl;

$R^1$ is methyl, ethyl or allyl; and $R^2$ and $R^3$ together form a group of the formula $—A^2—X^2—A^3—$ which together with the carbon atom to which $A^2$ and $A^3$ are attached define a ring having 6 ring atoms, wherein each of $A^2$ and $A^3$ is ethylene and $X^2$ is oxy, and which ring may optionally bear one or two methyl substituents;

or a pharmaceutically-acceptable salt thereof.

A further preferred compound of the invention comprises an oxime derivative of the formula I wherein $R^4$ is hydrogen, methyl or phenyl;

$R^5$ is hydrogen, methyl, 2-fluoroethyl or cyanomethyl;

$Ar^1$ is 1,4-phenylene;

$A^1$ is a direct link to $X^1$;

$X^1$ is thio;

$Ar^2$ is 1,3-phenylene, 5-fluoro-1,3-phenylene or 2,4-thiophenediyl (with the $X^1$ group in the 2-position);

$R^1$ is methyl; and $R^2$ and $R^3$ together form a group of the formula $—A^2—X^2—A^3—$ which together with the carbon atom to which $A^2$ and $A^3$ are attached define a ring having 6 ring atoms, wherein each of $A^2$ and $A^3$ is ethylene and $X^2$ is oxy, and which ring may optionally bear a methyl substituent alpha to $X^2$;

or a pharmaceutically-acceptable salt thereof.

A further preferred compound of the invention comprises an oxime derivative of the formula I wherein $R^4$ is methyl, ethyl or isopropyl;

$R^5$ is hydrogen, methyl, allyl, prop-2-ynyl, acetyl, pivaloyl, cyanomethyl, 3-pyridylmethyl or 4-pyridylmethyl;

$Ar^1$ is 1,4-phenylene;

$A^1$ is a direct link to $X^1$ and $X^1$ is thio or sulphonyl;

$Ar^2$ is 1,3-phenylene, 5-fluoro-1,3-phenylene, 2,4-thiophenediyl (with the $X^1$ group in the 2-position) or 2,5-thiazolediyl (with the $X^1$ group in the 2-position);

$R^1$ is methyl; and $R^2$ and $R^3$ together form a group of the formula —$A^2$—$X^2$—$A^3$— which together with the carbon atom to which $A^2$ and $A^3$ are attached define a ring having 5 or 6 ring atoms, wherein $A^2$ is methylene or ethylene, $A^3$ is ethylene and $X^2$ is oxy, and which ring may optionally bear a methyl substituent alpha to $X^2$;

or $R^1$ and $R^2$ together form a group of the formula —$A^2$—$X^2$—$A^3$— which together with the oxygen atom to which $A^2$ is attached and with the carbon atom to which $A^3$ is attached define a ring having 5 ring atoms, wherein $A^2$ is —$C(Me)_2$—, $A^3$ is methylene and $X^2$ is oxy, and $R^3$ is methyl;

or a pharmaceutically-acceptable salt thereof.

A further preferred compound of the invention comprises an oxime derivative of the formula I wherein $R^4$ is methyl, ethyl, isopropyl, hydroxymethyl or methoxymethyl;

$R^5$ is hydrogen, methyl, allyl, prop-2-ynyl, acetyl, pivaloyl, 2-hydroxyethyl, cyanomethyl, acetonyl, 3-pyridylmethyl or 4-pyridylmethyl;

$Ar^1$ is 1,4-phenylene or 2,5-pyridinediyl (with the $X^1$ group in the 2-position);

$A^1$ is a direct link to $X^1$ and $X^1$ is thio or sulphonyl;

$Ar^2$ is 1,3-phenylene, 5-fluoro-1,3-phenylene, 2,4-thiophenediyl (with the $X^1$ group in the 2-position), 2,4-thiazolediyl (with the $X^1$ group in the 2-position) or 2,5-thiazolediyl (with the $X^1$ group in the 2-position);

$R^1$ is methyl; and $R^2$ and $R^3$ together form a group of the formula —$A^2$—$X^2$13 $A^3$— which together with the carbon atom to which $A^2$ and $A^3$ are attached define a ring having 5 or 6 ring atoms, wherein $A^2$ is methylene or ethylene, $A^3$ is ethylene and $X^2$ is oxy, and which ring may optionally bear a methyl substituent alpha to $X^2$;

or $R^1$ and $R^2$ together form a group of the formula —$A^2$—$X^2$—$A^3$— which together with the oxygen atom to which $A^2$ is attached and with the carbon atom to which $A^3$ is attached define a ring having 5 ring atoms, wherein $A^2$ is —$C(Me)_2$—, $A^3$ is methylene and $X^2$ is oxy and $R^3$ is methyl;

or a pharmaceutically-acceptable salt thereof.

A further preferred compound of the invention comprises an oxime derivative of the formula I wherein $R^5$ is hydrogen, methyl, acetyl, cyanomethyl, 3-pyridylmethyl or 4-pyridylmethyl;

$Ar^1$ is 1,4-phenylene and $R^4$ is linked to $Ar^1$ ortho to the —N=C($R^4$)— group and defines an ethylene group, or a group of the formula

—$CH_2CH_2O$—;

$A^1$ is a direct link to $X^1$ and $X^1$ is thio, or $A^1$ is methylene and $X^1$ is oxy;

$Ar^2$ is 1,3-phenylene, 5-fluoro-1,3-phenylene, 2-amino-4,6-pyrimidinediyl or 2,4-thiophenediyl (with the $X^1$ group in the 2-position);

$R^1$ is methyl; and $R^2$ and $R^3$ together form a group of the formula —$A^2$—$X^2$—$A^3$— which together with the carbon atom to which $A^2$ and $A^3$ are attached define a ring having 5 or 6 ring atoms, wherein $A^2$ is methylene or ethylene, $A^3$ is ethylene and $X^2$ is oxy, and which ring may optionally bear a methyl substituent alpha to $X^2$;

or a pharmaceutically-acceptable salt thereof.

A further preferred compound of the invention comprises an oxime derivative of the formula I wherein $R^5$ is hydrogen, methyl, acetyl, pivaloyl, cyanomethyl, 3-pyridylmethyl or 4-pyridylmethyl;

$Ar^1$ is 1,4-phenylene and $R^4$ is linked to $Ar^1$ ortho to the —N=C($R^4$)— group and defines an ethylene group, or a group of the formula

—$CH_2CH_2O$—;

$A^1$ is a direct link to $X^1$ and $X^1$ is thio, or $A^1$ is methylene and $X^1$ is oxy;

$Ar^2$ is 1,3-phenylene, 5-fluoro-1,3-phenylene, 2-amino-4,6-pyrimidinediyl, 2,4-thiophenediyl (with the $X^1$ group in the 2-position) or 2,5-thiazolediyl (with the $X^1$ group in the 2-position);

$R^1$ is methyl; and $R^2$ and $R^3$ together form a group of the formula —$A^2$—$X^2$—$A^3$— which together with the carbon atom to which $A^2$ and $A^3$ are attached define a ring having 5 or 6 atoms, wherein $A^2$ is methylene or ethylene, $A^3$ is ethylene and $X^2$ is oxy, and which ring may optionally bear a methyl substituent alpha to $X^2$;

or a pharmaceutically-acceptable salt thereof.

A specific especially preferred compound of the invention is, for example, the following oxime derivative of the formula I, or a pharmaceutically-acceptable salt thereof:

(E)-4'-[5-fluoro-3-(4-methoxytetrahydropyran-4-yl)phenylthio]acetophenone oxime, (E)-4'-[5-fluoro-3-(4-methoxytetrahydropyran-4-yl)phenylthio]acetophenone oxime O-methyl ether, (E)-4'-[5-fluoro-3-(4-methoxytetrahydropyran-4-yl)phenylthio]acetophenone oxime O-(2-fluoroethyl)ether, (E)-4'-[5-fluoro-3-(4-methoxytetrahydropyran-4-yl)phenylthio]acetophenone oxime O-cyanomethyl ether, (E)-4'-[4-(4-methoxytetrahydropyran-4-yl)thien-2-ylthio] acetophenone oxime, (Z)-4'-[4-(4-methoxytetrahydropyran-4-yl)thien-2-ylthio] acetophenone oxime or (E)-4'-[4-(4-methoxytetrahydropyran-4-yl)thien-2-ylthio] acetophenone oxime O-cyanomethyl ether.

A further specific especially preferred compound of the invention is, for example, the following oxime derivative of the formula I, or a pharmaceutically-acceptable salt thereof:

O-acetyl-(E)-4'-[5-fluoro-3-(4-methoxytetrahydropyran-4-yl)phenylthio]acetophenone oxime, (E)-4'-[5-fluoro-3-(4-methoxytetrahydropyran-4-yl)phenylthio]acetophenone oxime O-(4-pyridyl)methyl ether, (E)-4'-{5-fluoro-3-[(2S,4R)-4-methoxy-2-methyltetrahydropyran-4-yl]phenylthio}acetophenone oxime, (E)-5-[5-fluoro-3-(4-methoxytetrahydropyran-4-yl)phenylthio]indan-1-one oxime O-cyanomethyl ether, 7-[5-fluoro-3-(4-methoxytetrahydropyran-4-yl)phenylthio]
chroman-4-one oxime, 7-[5-fluoro-3-(4-methoxytetrahydropyran-4-yl)phenylthio]
chroman-4-one oxime O-methyl ether, (E)-5-[5-fluoro-3-(4-methoxytetrahydropyran-4-yl)phe-
nylthio]indan-1-one O-(4-pyridyl)methyl ether, (E)-4'-{5-fluoro-3-[(2RS,3SR)-3-methoxy-2-methyltetrahy-
drofuran-3-yl]phenylthio}acetophenone oxime or (E)-4'-[4-(2,2,4-trimethyl-1,3-dioxolan-4-yl)thien-2-ylthio]
acetophenone oxime.

A further specific especially preferred compound of the invention is, for example, the following oxime derivative of the formula I, or a pharmaceutically-acceptable salt thereof:

(E)-4'-{5-fluoro-3-[(2S,4R)-4-methoxy-2-methyltetrahy-
dropyran-4-yl]phenylsulphonyl}acetophenone oxime, (E)-4'-{5-fluoro-3-[(2S,4R)-4-methoxy-2-methyltetrahy-
dropyran-4-yl]phenylthio}acetophenone oxime O-cya-
nomethyl ether, (E)-4'-{5-fluoro-3-[(2S,4R)-4-methoxy-2-methyltetrahy-
dropyran-4-yl]phenylsulphonyl}acetophenone oxime
O-cyanomethyl ether, (E)-4'-{5-[(2S,4R)-4-methoxy-2-methyltetrahydropyran-4-
yl]thiazol-2-ylthio}acetophenone oxime O-cyanomethyl
ether, (E)-4'-{5-[(2S,4R)-4-methoxy-2-methyltetrahydropyran-4-
yl]thiazol-2-ylthio}acetophenone oxime, (E)-5-{4-[(2S,4R)-4-methoxy-2-methyltetrahydropyran-4-
yl]thien-2-ylthio}indan-1-one oxime, (E)-5-{4-[(2S,4R)-4-methoxy-2-methyltetrahydropyran-4-
yl]thien-2-ylthio}indan-1-one oxime O-cyanomethyl
ether, (E)-4'-{4-[(2S,4R)-4-methoxy-2-methyltetrahydropyran-4-
yl]thien-2-ylthio}acetophenone oxime, (E)-4'-{4-[(2S,4R)-4-methoxy-2-methyltetrahydropyran-4-
yl]thien-2-ylthio}acetophenone oxime O-cyanomethyl
ether, (E)-4'-[3-(4-methoxytetrahydropyran-4-yl)phenylsulpho-
nyl]acetophenone oxime O-cyanomethyl ether, (E)-4'-[5-(4-methoxytetrahydropyran-4-yl)thiazol-2-ylthio]
acetophenone oxime O-cyanomethyl ether, (E)-7-[4-(4-methoxytetrahydropyran-4-yl)thien-2-ylthio]
chroman-4-one oxime O-cyanomethyl ether, O-acetyl-(E)-4'-[4-(4-methoxytetrahydropyran-4-yl)thien-
2-ylthio]acetophenone oxime, (E)-4'-{4-[(2RS,3SR)-3-methoxy-2-methyltetrahydrofuran-
3-yl]thien-2-ylthio}acetophenone oxime O-cyanomethyl
ether, (E)-4'-{4-[(2R,3S)-3-methoxy-2-methyltetrahydrofuran-3-
yl]thien-2-ylthio}acetophenone oxime O-cyanomethyl
ether, (E)-4'-{4-[(2R,3S)-3-methoxy-2-methyltetrahydrofuran-3-
yl]thien-2-ylsulphonyl}acetophenone oxime O-cyanom-
ethyl ether, (E)-4'-{5-[(2RS,3SR)-3-methoxy-2-methyltetrahydrofuran-
3-yl]thiazol-2-ylthio}acetophenone oxime, (E)-4'-[4-(2,2,4-trimethyl-1,3-dioxolan-4-yl)thien-2-ylthio]
acetophenone oxime O-cyanomethyl ether, (E)-4'-[4-(2,2,4-trimethyl-1,3-dioxolan-4-yl)thien-2-ylsul-
phonyl]acetophenone oxime O-cyanomethyl ether, (E)-7-[4-(2,2,4-trimethyl-1,3-dioxolan-4-yl)thien-2-ylthio]
chroman-4-one oxime -cyanomethyl ether or (E)-4'-{4-[(4S)-2,2,4-trimethyl-1,3-dioxolan-4-yl]thien-2-
ylthio}acetophenone oxime O-cyanomethyl ether.

A compound of the invention comprising an oxime derivative of the formula I, or a pharmaceutically-acceptable salt thereof, may be prepared by any process known to be applicable to the preparation of structurally-related compounds. Such procedures are provided as a further feature of the invention and are illustrated by the following represen-
tative examples in which, unless otherwise stated, $R^4$, $R^5$, $Ar^1$, $A^1$, $X^1$, $Ar^2$, $R^1$, $R^2$ and $R^3$ have any of the meanings defined hereinbefore, provided that when there is an amino, imino, alkylamino, carboxy or hydroxy group in $R^4$, $R^5$, $Ar^1$, $Ar^2$, $R^2$ or $R^3$ then any such group may optionally be protected by a conventional protecting group which may be removed when so desired by conventional means.

(a) The reaction, conveniently in the presence of a suitable base, of a compound of the formula II

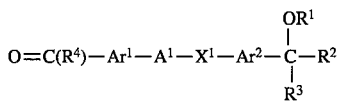

with a hydroxylamine of the formula $R^5O$—$NH_2$.

A suitable base for the reaction is, for example, an alkali or alkaline earth metal carbonate, (1–4C)alkoxide, (1–4C)alkanoate, hydroxide or hydride, for example sodium carbonate, potassium carbonate, barium carbonate, sodium ethoxide, potassium butoxide, sodium acetate, sodium hydroxide, potassium hydroxide, sodium hydride or potassium hydride. Alternatively a suitable base for the reaction is, for example, an organic amine base such as pyridine, 2,6-lutidine, collidine, 4-dimethylaminopyridine, triethylamine, N-methylmorpholine or diazabicyclo[5.4.0]undec-7-ene.

The reaction is conveniently performed in a suitable inert solvent or diluent, for example, one or more of water, a (1–4C)alcohol such as methanol, ethanol and propanol, pyridine, 1,2-dimethoxyethane, tetrahydrofuran, 1,4-dioxan or a dipolar aprotic solvent such as N,N-dimethylformamide and dimethylsulphoxide. The reaction is conveniently performed at a temperature in the range, for example, 10° to 150° C., conveniently at or near 70° C.

The starting materials of the formula II may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist. The disclosures of European Patent Applications Nos. 0375405, 0385662, 0409413 and 0420511 are particularly relevant to the preparation of suitable starting materials.

(b) For the production of those compounds of the formula I wherein $R^5$ is (1–4C)alkyl or substituted-alkyl, the alkylation, conveniently in the presence of a suitable base as defined hereinbefore, of an oxime of the formula III

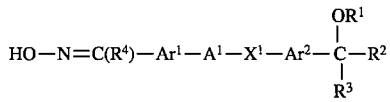

with an alkylating agent of the formula $R^5$—Z, wherein Z is a displaceable group.

A suitable displaceable group Z is, for example, a halogeno or sulphonyloxy group, for example a chloro, bromo, iodo, methanesulphonyloxy or toluene-4-sulphonyloxy group.

The reaction is conveniently performed in a suitable inert solvent or diluent, for example N,N-dimethylformamide, N,N-dimethylacetamide, dimethylsulphoxide, acetone, 1,2-dimethoxyethane, tetrahydrofuran, 1,4-dioxan or methylene chloride, and at a temperature in the range, for example, −10° to 150° C., conveniently at or near ambient temperature.

The starting materials of the formula III may be obtained by the process of paragraph (a) hereinbefore utilizing a hydroxylamine of the formula $R^5O—NH_2$ wherein $R^5$ is hydrogen. The preparation of such starting materials is described within the accompanying non-limiting Examples.

(c) For the production of those compounds of the formula I wherein $R^5$ is (2–5C)alkanoyl, carbamoyl, N-(1–4C)alkylcarbamoyl or N,N-di-(1–4C)alkylcarbamoyl, the acylation, conveniently in the presence of a suitable base as defined hereinbefore, of an oxime of the formula III

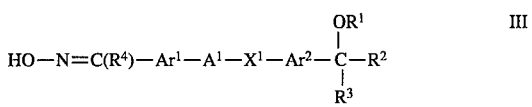

with an acylating agent of the formula $R^5$—Z, wherein Z is a displaceable group as defined hereinbefore.

The reaction is conveniently performed in a suitable inert solvent or diluent as defined in paragraph (b) hereinbefore, and at a temperature in the range, for example, −10° to 150° C., conveniently at or near ambient temperature.

(d) For the production of those compounds of the formula I wherein $R^4$ is cyano or (2–5C)alkanoyl, the reaction, conveniently in the presence of a suitable base as defined hereinbefore, of a compound of the formula IV

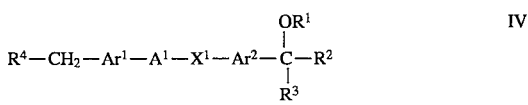

with an alkylnitrite.

A suitable alkylnitrite is, for example, isopentylnitrite as illustrated in the accompanying non-limiting Examples. The reaction is conveniently performed in a suitable inert solvent or diluent as defined in paragraph (b) hereinbefore, and at a temperature in the range, for example, 10° to 100° C., conveniently at or near 50° C.

The starting materials of the formula IV may be obtained by standard procedures of organic chemistry. The preparation of such starting materials is described within the accompanying Examples.

(e) For the production of those compounds of the formula I wherein $R^4$ is amino, (1–4C)alkylamino, di-(1–4C)alkylamino or (1–4C)alkylthio, the alkylation of ammonia, a (1–4C)alkylamine, a di-(1–4C)alkylamine or a (1–4C)alkanethiol with an alkylating agent of the formula V

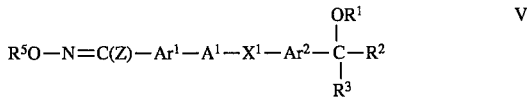

wherein Z is a displaceable group as defined hereinbefore.

The reaction is conveniently performed in a suitable inert solvent or diluent as defined in paragraph (b) hereinbefore, and at a temperature in the range, for example, 10° to 100° C., conveniently at or near ambient temperature.

The starting material of the formula V may be obtained by standard procedures of organic chemistry. The preparation of such a starting material wherein Z is a halogeno group is described within the accompanying Examples.

(f) For the production of those compounds of the formula I wherein $R^1$ and $R^2$ are linked, the cyclization, conveniently in the presence of a suitable acid, of a compound of the formula VI

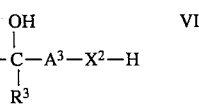

with an appropriate aldehyde or ketone, or with the corresponding hemiacetal or acetal derivative thereof.

A suitable acid for the cyclization reaction is, for example, an inorganic acid such as hydrochloric, sulphuric or phosphoric acid, or, for example, an organic acid such as 4-toluenesulphonic acid or trifluoroacetic acid. The cyclisation reaction is conveniently performed in a suitable inert solvent or diluent, for example 1,2-dimethoxyethane or tetrahydrofuran. Preferably the reaction is performed using the appropriate aldehyde or ketone as both a reactant and diluent. The cyclization is effected at a temperature in the range, for example, 20° to 150° C., conveniently at or near the boiling point of the diluent or solvent.

The tertiary alcohol starting material of the formula VI may be obtained by standard procedures of organic chemistry. The preparation of examples of such starting materials is described within the accompanying non-limiting Examples which are provided for the purpose of illustration only.

(g) The coupling of a compound of the formula VII

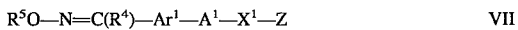

wherein Z is a displaceable group as defined hereinbefore, or alternatively, when $X^1$ is a thio group, Z may be a group of the formula

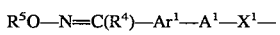

with an organometallic reagent of the formula VIII

wherein M is an alkali metal or alkaline earth metal such as lithium or calcium or M represents the magnesium halide portion of a conventional Grignard reagent.

The coupling reaction is conveniently performed in a suitable inert solvent or diluent as defined hereinbefore and at a temperature in the range, for example, −80° to +50° C., conveniently in the range −80° C. to ambient temperature.

The preparation of the starting materials of the formulae VII and VII is described within the accompanying non-limiting Examples which are provided for the purpose of illustration only. Alternatively such starting materials may be obtained by standard procedures of organic chemistry.

(h) For the production of those compounds of the formula I wherein $X^1$ is a sulphinyl or sulphonyl group, wherein $R^2$ and $R^3$ together form a group of the formula $—A^2—X^2—A^3—$ and $X^2$ is a sulphinyl or sulphonyl group or wherein $R^1$ and $R^2$ together form a group of the formula $—A^2—X^2—A^3—$ and $X^2$ is a sulphinyl or sulphonyl group, the oxidation of a compound of the formula I wherein $X^1$ is a thio group, wherein $R^2$ and $R^3$ together form a group of the formula $—A^2—X^2—A^3—$ and $X^2$ is a thio group or wherein $R^1$ and $R^2$ together form a group of the formula $—A^2—X^2—A^3—$ and $X^2$ is a thio group.

A suitable oxidizing agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidizing agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidizing agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(i) For the production of those compounds of the formula I wherein $R^5$ is a carboxy-(1–4C)alkyl group, the hydrolysis of a compound of the formula I wherein $R^5$ is a (1–4C)alkoxycarbonyl-(1–4C)alkyl group.

The hydrolysis is conveniently performed in the presence of a suitable base as defined hereinbefore. Alternatively when the (1–4C)alkoxycarbonyl group is, for example, a tert-butoxycarbonyl group, the hydrolysis may be performed in the presence of a suitable acid as defined hereinbefore. The reaction is conveniently performed in a suitable solvent or diluent as defined hereinbefore and at a temperature in the range, for example, 10° to 150° C., conveniently at or near 50° C.

Conventional protecting groups for an amino, imino, alkylamino, carboxy or hydroxy group which may be present in $R^4$, $R^5$, $Ar^1$, $Ar^2$ or the ring defined by $R^2$ and $R^3$ are set out hereinafter.

A suitable protecting group for an amino, imino or alkylamino group is, for example, an acyl group for example a (2–4C)alkanoyl group (especially acetyl), a (1–4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a carboxy group is, for example, an esterifying group, for example a (1–4C)alkyl group (especially methyl or ethyl) which may be removed, for example, by hydrolysis with a suitable base such as an alkali metal hydroxide, for example lithium or sodium hydroxide; or, for example, a tert-butyl group which may be removed, for example, by treatment with a suitable acid such as hydrochloric, sulphuric or phosphoric acid or trifluoroacetic acid.

A suitable protecting group for a hydroxy group is, for example, an acyl group, for example a (2–4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

When a pharmaceutically-acceptable salt of a compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

As stated previously, the compounds of the formula I are inhibitors of the enzyme 5-LO. The effects of this inhibition may be demonstrated using one or more of the standard procedures set out below:

a) An in vitro assay system involving incubating a test compound with heparinised human blood, prior to challenge with the calcium ionophore A23187 and then indirectly measuring the inhibitory effects on 5-LO by assaying the amount of $LTB_4$ using specific radioimmunoassays described by Carey and Forder (*Prostaglandins, Leukotrienes Med.*, 1986, 22, 57; *Prostaglandins*, 1984, 28, 666; *Brit. J. Pharmacol.*, 1985, 84, 34P) which involves the use of a protein-$LTB_4$ conjugate produced using the procedure of Young et alia (*Prostaglandins*, 1983, 26(4), 605–613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2$($TxB_2$) described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

b) An ex vivo assay system, which is a variation of test a) above, involving administration to a group of rats of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

c) An in vivo system involving measuring the effects of a test compound administered orally against the liberation of $LTB_4$ induced by zymosan within an air pouch generated within the subcutaneous tissue of the back of male rats. The rats are anesthetized and air pouches are formed by the injection of sterile air (20 ml). A further injection of air (10 ml) is similarly given after 3 days. At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in one or more of the above tests a)–c):

Test a): $IC_{50}$ ($LTB_4$) in the range, for example, 0.01–40 μM $IC_{50}$ ($T \times B_2$) in the range, for example, 40–200 μM;

Test b): oral $ED_{50}$($LTB_4$) in the range, for example, 0.1–100 μmg/kg;

Test c): oral $ED_{50}$($LTB_4$) in the range, for example, 0.1–50 mg/kg.

No overt toxicity or other untoward effects are present in tests b) and/or c) when compounds of the formula I are administered at several multiples of their minimum inhibitory dose or concentration Thus, by way of example, the compound (E)-4'-[5-fluoro-3-(4-methoxytetrahydropyran-4-yl)phenylthio]acetophenone oxime O-methyl ether has an $IC_{50}$ of 0.11 μM against $LTB_4$ in test a) and an oral $ED_{50}$ of approximately 0.5 mg/kg versus $LTB_4$ in test c); the compound (E)-4'-[5-fluoro-3-(4-methoxytetrahydropyran-4-yl)phenylthio]acetophenone oxime O-cyanomethyl ether has an $IC_{50}$ of 0.03 μM against $LTB_4$ in test a) and an oral $ED_{50}$ of approximately 0.5 mg/kg versus $LTB_4$ in test c); and the compound (E)-4'-{5-fluoro-3-[(2S,4R)-4-methoxy-2 -methyltetrahydropyran-4-yl]phenylthio}acetophenone oxime has an $IC_{50}$ of 0.04 μM against $LTB_4$ in test a) and an oral $ED_{50}$ of approximately 0.05 mg/kg versus $LTB_4$ in test c). In general those compounds of the formula I which are particularly preferred have an $IC_{50}$ of <1 μM against $LTB_4$ in test a) and an oral $ED_{50}$ of <10 mg/kg against $LTB_4$ in tests b) and/or c).

These compounds are examples of compounds of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises an oxime derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is an oxime derivative of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided an oxime derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a compound of the formula I will naturally vary according to the nature and severity of the conditions, the age and sex of the animal or patient and the route of administration, according to well known principles of medicine. As mentioned above, compounds of the formula I are useful in treating those allergic and inflammatory conditions which are due alone or in part to the effects of the metabolites of arachidonic acid arising by the linear (5-LO catalyzed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises an oxime derivative of the formula I, or a pharmaceutically-acceptable salt thereof as defined hereinbefore, in conjunction or admixture with a cyclooxygenase inhibitory non-steroidal anti-inflammatory agent (such as those mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at ambient temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, W. Germany;

(iv) yields are given for illustration only and are not necessarily the maximum attainable;

(v) the structures of the end-products of the formula I were confirmed by NMR and mass spectral techniques; unless otherwise stated, $CDCl_3$ solutions of the end-products of the formula I were used for the determination of the NMR spectral data, chemical shift values were measured on the delta scale and the following abbreviations are used: s, singlet; d, doublet; t, triplet; q, quartet; m, multiplet;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after recrystallization from a conventional organic solvent such as ethanol, methanol, acetone, ether or hexane, alone or in admixture;

(viii) many of the oxime derivatives disclosed in the accompanying Examples have not been positively identified as the (E)-geometric isomer, although it is believed, based on those Examples wherein mixtures of (E)- and (Z)-isomers were obtained and their separation was achieved, that the major product in each case has the (E)-configuration, the configuration of those oximes which have been positively identified as (E)-isomers or as mixtures of (E)- and (Z)-isomers was assigned according to conventional procedures utilizing $^{13}C$ NMR;

(ix) the following abbreviations have been used:
THF tetrahydrofuran;
DMF N,N-dimethylformamide;
DMSO dimethylsulphoxide;
NMP N-methylpyrrolidin-2-one;
DMA N,N-dimethylacetamide.

(x) the following shorthand descriptions have been used:
sodium hydride (60%) Sodium hydride (a 60% weight/weight dispersion in mineral oil;
petroleum ether petroleum ether (b.p. 40°–60° C.).

EXAMPLE 1

A mixture of 4'-[5-fluoro-3-(4-methoxytetrahydropyran-4-yl)phenylthio]acetophenone (2.6 g), hydroxylamine hydrochloride (0.6 g), barium carbonate (1.7 g), water (15 ml) and ethanol (75 ml) was stirred and heated to reflux for 5 hours. The bulk of the ethanol was evaporated and the residue was partitioned between diethyl ether and water. The organic phase was washed with brine, dried ($MgSO_4$) and evaporated. The residue was purified by column chromatography using a 10:1 v/v mixture of methylene chloride and diethyl ether as eluent. There was thus obtained (E)-4'-[5-fluoro-3-(4-methoxytetrahydropyran-4-yl)phenylthio]acetophenone oxime (2.3 g, 85%), m.p. 155°–156° C.;

NMR Spectrum: 1.8–2.1 (m, 4H), 2.27 (s, 3H), 2.98 (s, 3H), 3.7–3.9 (m, 4H), 6.8–7.7 (m, 7H);

Elemental Analysis: Found C, 64.2; H, 5.9; N, 3.7; $C_{20}H_{22}FNO_3S$ requires C, 64.0; H, 5.9; N, 3.7%.

The 4'-[5-fluoro-3-(4-methoxytetrahydropyran-4-yl)phenylthio]acetophenone used as a starting material was obtained as follows:

A mixture of 4'-iodoacetophenone (2.46 g), 4-(5-fluoro-3-mercaptophenyl)-4-methoxytetrahydropyran (European Patent Application No. 0420511, Example 4 thereof; 1.61 g), potassium carbonate (2.76 g), cuprous chloride (0.4 g) and DMF (10 ml) was stirred and heated to 140° C. for 2 hours. The mixture was cooled to ambient temperature and partitioned between diethyl ether and water. The organic phase was washed with brine, dried ($MgSO_4$) and evaporated. The product was purified by column chromatography using initially methylene chloride and then increasingly polar mixtures of methylene chloride and diethyl ether as eluent. There was thus obtained the required starting material (1.62 g, 45%) m.p. 86°–87° C.

EXAMPLE 2

Sodium hydride (60% w/w dispersion in mineral oil, 0.024 g) was added to a stirred solution of (E)-4'-[5-fluoro-3-(4-methoxytetrahydropyran-4-yl)phenylthio] acetophenone oxime (0.14 g) in THF (5 ml) and the mixture was stirred at ambient temperature for 10 minutes. Methyl iodide (0.212 g) was added and the mixture was stirred at ambient temperature for 16 hours. The mixture was partitioned between diethyl ether and water. The organic phase was washed with brine, dried ($MgS_4$) and evaporated. The product was purified by column chromatography using increasingly polar mixtures of methylene chloride and diethyl ether as eluent. There was thus obtained (E)-4'-[5-fluoro-3-(4-methoxytetrahydropyran-4-yl)phenylthio]acetophenone oxime O-methyl ether (0.075 g, 52%), m.p. 41°–42° C.;

NMR Spectrum: 1.8–2.0 (m, 4H), 2.20 (s, 3H), 2.97 (s, 3H), 3.7–3.9 (m, 4H), 3.98 (s, 3H), 6.75–7.70 (m, 7H);

Elemental Analysis: Found C, 64.5; H, 6.1; N, 3.6; $C_{21}H_{24}FNO_3S$ requires C, 64.8; H, 6.2: N, 3.6%.

EXAMPLE 3

Sodium hydride (60% w/w dispersion in mineral oil, 0.03 g) was added to a stirred mixture of (E)-4'-[5-fluoro-3-(4-methoxytetrahydropyran-4-yl)phenylthio]acetophenone oxime (0.16 g), 1,4,7,10,13-pentaoxacyclopentadecane (2 drops; hereinafter 15-crown-5) and THF (3 ml) and the mixture was stirred at ambient temperature for 10 minutes. 1-Bromo-2-fluoroethane (0.077 g) was added and the mixture was stirred at ambient temperature for 2 hours. The mixture was partitioned between diethyl ether and water. The organic phase was washed with brine, dried ($MgSO_4$) and evaporated. The residue was purified by column chromatography using a 20:3 v/v mixture of petroleum ether (b.p. 40°–60° C.) and ethyl acetate as eluent. There was thus obtained (E)-4'-[5-fluoro-3-(4-methoxytetrahydropyran-4-yl)phenylthio]acetophenone oxime O-(2-fluoroethyl) ether as an oil (0.143 g, 80%);

NMR Spectrum: 1.75–2.2 (m, 4H), 2.27 (s, 3H), 2.99 (s, 3H), 3.7–3.95 (m, 4H), 4.2–4.5 (m, 2H), 4.55–5.05 (m, 2H), 6.8–7.75 (m, 7H);

Elemental Analysis: Found C, 62.9; H, 6.0; N, 3.1; $C_{22}H_{25}F_2NO_3S$ requires C, 62.7; H, 6.0; N, 3.3%.

EXAMPLE 4

The procedure described in Example 3 was repeated except that ethyl bromoacetate was used in place of 1-bromo-2-fluoroethane. There was thus obtained (E)-4'-[5-fluoro-3-(4-methoxytetrahydropyran-4-yl)phenylthio]acetophenone oxime O-ethoxycarbonylmethyl ether as an oil in 64% yield;

NMR Spectrum: 1.29 (t, 3H), 1.75–2.05 (m, 4H), 2.31 (s, 3H), 3.0 (s, 3H), 3.7–3.95 (m, 4H), 4.24 (q, 2H), 4.73 (s, 2H), 6.75–7.7 (m, 7H);

Elemental Analysis: Found C, 62.2; H, 6.2; N, 2.8; $C_{24}H_{28}FNO_5S$ requires C, 62.5; H, 6.1; N, 3.0%.

EXAMPLE 5

The procedure described in Example 3 was repeated except that bromoacetonitrile was used in place of 1-bromo-2-fluoroethane. There was thus obtained (E)-4'-[5-fluoro-3-(4-methoxytetrahydropyran-4-yl)phenylthio]acetophenone oxime O-cyanomethyl ether as an oil in 89% yield;

NMR Spectrum: 1.6–2.1 (m, 4H), 2.18 (s, 3H), 2.98 (s, 3H), 3.6–3.9 (m, 4H), 4.74 (s, 2H), 6.7–7.6 (m, 11H);

Elemental Analysis: Found C, 63.5; H, 5.7; N, 6.5; $C_{22}H_{23}FN_2O_3S$ requires C, 63.7; H, 5.6; N, 6.8%.

EXAMPLE 6

The procedure described in Example 3 was repeated except that ethyl 2-bromomethylthiazole-4-carboxylate was used in place of 1-bromo-2-fluoroethane. There was thus obtained (E)-4'-[5-fluoro-3-(4-methoxytetrahydropyran-4-yl)phenylthio]acetophenone oxime O-(4-ethoxycarbonylthiazol-2-yl)methyl ether as an oil in 73% yield;

NMR Spectrum: 1.41 (t, 3H), 1.8–2.1 (m, 4H), 2.30 (s, 3H), 2.99 (s, 3H), 3.7–3.95 (m, 4H), 4.43 (q, 2H), 5.53 (s, 2H), 6.8–7.8 (m, 7H), 8.15 (s, 1H);

Elemental Analysis: Found C, 59.2; H, 5.6; N, 5.0; $C_{27}H_{29}FN_2O_5S_2$. 0.3EtOAc requires C, 59.3; H, 5.5; N, 4.9%.

EXAMPLE 7

A mixture of 4'-[4-(4-methoxytetrahydropyran-4-yl)thien-2-ylthio]acetophenone (0.62 g), hydroxylamine hydrochloride (0.136 g) and pyridine (6 ml) was stirred and heated to 35° C. for 1 hour. The mixture was partitioned between ethyl acetate and water. The organic phase was washed with water, dried ($MgSO_4$) and evaporated. The residue was purified by column chromatography using a 7:3 v/v mixture of petroleum ether (b.p. 40°–60° C.) and ethyl acetate as eluent. There were thus obtained in turn:

(E)-4'-[4-(4-methoxytetrahydropyran-4-yl)thien-2-ylthio]
acetophenone oxime (0.52 g, 80%), m.p. 120°–122° C.;

NMR Spectrum ($CD_3COCD_3$): 1.85–2.1 (m, 4H), 2.19 (s, 3H), 3.03 (s, 3H), 3.6–3.8 (m, 4H), 7.15–7.75 (m, 6H);

Elemental Analysis: Found C, 59.5; H, 5.9; N, 3.8; $C_{18}H_{21}NO_3S_2$ requires C, 59.5; H, 5.8; N, 3.85%; and the corresponding (Z)-isomer (0.045 g, 7%), m.p. 140°–142° C.;

NMR Spectrum ($CD_3COCD_3$): 1.85–2.0 (m, 4H), 2.11 (s, 3H), 3.03 (s, 3H), 3.5–3.8 (m, 4H), 7.1–7.75 (m, 6H);

Elemental Analysis: Found C, 59.6; H, 6.0; N, 3.8; $C_{18}H_{21}NO_3S_2$ requires C, 59.5; H, 5.8; N, 3.85%.

The 4'-[4-(4-methoxytetrahydropyran-4-yl)thien-2-ylthio]acetophenone used as a starting material was obtained as follows:

A mixture of sodium hydrosulfide hydrate (NaSH, 33.6 g) and N-methylmorpholine (220 ml) was stirred and heated to 160° C. The mixture was partially evaporated under vacuum to remove the water. A solution of 4'-bromoacetophenone (40 g) in N-methylpyrrolidin-2-one (30 ml) was added dropwise to the residue and the mixture was stirred and heated to 160° C. for 90 minutes. The mixture was evaporated and the residue was poured into a mixture of ethyl acetate, water and ice. The aqueous phase was acidified to pH2 by the addition of dilute aqueous hydrochloric acid and extracted with ethyl acetate. The organic extract was washed with brine, dried ($MgSO_4$) and evaporated. There was thus obtained 4'-mercaptoacetophenone as an oil (25 g) which was used without further purification.

A solution of the oil so obtained in DMSO (100 ml) was stirred at ambient temperature for 16 hours. The mixture was poured onto a mixture of ice and water and extracted with ethyl acetate. The organic extract was washed with brine, dried ($MgSO_4$) and evaporated. The residue was purified by column chromatography using a 7:3 v/v mixture of petroleum ether (b.p. 40°–60° C.) and ethyl acetate as eluent. There was thus obtained di-(4-acetylphenyl) disulphide (16.3 g, m.p. 94°–95° C.

A mixture of di-(4-acetylphenyl) disulphide (1.9 g), ethylene glycol (2.45 ml), triethyl orthoformate (5 ml), 4-toluenesulphonic acid (0.041 g) and toluene (22 ml) was stirred and heated to 45° C. for 2 hours. The mixture was cooled to ambient temperature, washed with a saturated aqueous sodium bicarbonate solution, dried ($MgSO_4$) and evaporated. The residue was purified by column chromatography using a 3:7 v/v mixture of petroleum ether (b.p. 40°–60° C.) and ethyl acetate as eluent. There was thus obtained di-[4-(2-methyl-1,3-dioxolan-2-yl)phenyl]disulphide (2.12 g, 99%), m.p. 135°–137° C.

n-Butyl-lithium (1.5M in hexane, 2.74 ml) was added dropwise to a stirred solution of di-isopropylamine (0.59 ml) in THF (10 ml) which had been cooled to –78° C. and the mixture was stirred at –60° C. for 15 minutes. The mixture was recooled to –78° C. and a solution of 4-methoxy-4-(3-thienyl)tetrahydropyran (European Patent Application No.

91305531.5, Example 6 thereof; 0.8 g) in THF (1 ml) was added dropwise. The resultant mixture was allowed to warm to −30° C. over approximately 2 hours. The mixture was recooled to −78° C. and a solution of di-[4-(2-methyl-1,3-dioxolan-2-yl)phenyl]disulphide (1.56 g) in THF (20 ml) was added dropwise. The mixture was allowed to warm to ambient temperature and was stirred for 16 hours. The mixture was poured into a cold aqueous ammonium chloride solution and extracted with ethyl acetate. The organic phase was washed with water, dried ($MgSO_4$) and evaporated. The residue was purified by column chromatography using a 4:1 v/v mixture of petroleum ether (b.p. 40°–60° C.) and ethyl acetate as eluent. There was thus obtained 4'-[4-(4-methoxytetrahydropyran-4-yl)thien-2-ylthio]acetophenone ethylene acetal (0.63 g, 40%), the structure of which was confirmed by proton magnetic resonance spectroscopy.

To a solution of the material so obtained in acetone (5 ml), there was added a solution of 2N aqueous hydrochloric acid (2 drops) in acetone (12 ml) and the resultant mixture was stirred at ambient temperature for 2 hours. The mixture was neutralized by the addition of sodium bicarbonate. The mixture was evaporated and the residue was partitioned between ethyl acetate and water. The organic phase was washed with water, dried ($MgSO_4$) and evaporated. The residue was purified by column chromatography using a 4:1 v/v mixture of petroleum ether (b.p. 40°–60° C.) and ethyl acetate as eluent. There was thus obtained the required starting material (0.54 g, 80%), m.p. 70°–72° C.

EXAMPLE 8

Using an analogous procedure to that described in Example 2, (E)-4'-[4-methoxytetrahydropyran-4-yl)thien-2-ylthio]acetophenone oxime was reacted with methyl iodide to give (E)-4'-[4-(4-methoxytetrahydropyran-4-yl)thien-2-ylthio]acetophenone oxime O-methyl ether as an oil in 58% yield;

NMR Spectrum: 1.9–2.07 (m, 4H), 2.17 (s, 3H), 3.03 (s, 3H), 3.6–3.9 (m, 4H), 3.96 (s, 3H), 7.1–7.6 (m, 6H);

Elemental Analysis: Found C, 60.4; H, 6.2; N, 3.8; $C_{19}H_{23}NO_3S_2$ requires C, 60.4; H, 6.1; N, 3.7%.

EXAMPLE 9

Using an analogous procedure to that described in Example 2, (E)-4'-[4-(4-methoxytetrahydropyran-4-yl)thien-2-ylthio]acetophenone oxime was reacted with bromoacetonitrile to give (E)-4'-[4-(4-methoxytetrahydropyran-4-yl)thien-2-ylthio]acetophenone oxime O-cyanomethyl ether in 88% yield, m.p. 88°–90° C.;

NMR Spectrum: 1.9–2.1 (m, 4H), 2.22 (s, 3H), 3.04 (s, 3H), 3.7–3.9 (m, 4H), 4.79 (s, 2H), 7.1–7.7 (m, 6H);

Elemental Analysis: Found C, 59.7; H, 5.6; N, 6.9; $C_{20}H_{22}N_2O_3S_2$ requires C, 59.7; H, 5.5; N, 7.0%.

EXAMPLE 10

A mixture of 4-[5-fluoro-3-(4-methoxytetrahydropyran-4-yl)phenylthio]benzaldehyde (2 g), hydroxylamine hydrochloride (0.6 g), ethanol (10 ml) and pyridine (10 ml) was stirred and heated to 70° C. for 4 hours. The mixture was cooled to ambient temperature and partitioned between diethyl ether and water. The organic phase was washed with brine, dried ($MgSO_4$) and evaporated. The residue was purified by column chromatography using increasingly polar mixtures of petroleum ether (b.p. 40°–60° C.) and ethyl acetate as eluent. There was thus obtained 4-[5-fluoro-3-(4-methoxytetrahydropyran-4-yl)phenylthio]benzaldehyde oxime (1.83 g, 88%), m.p. 121°–122° C.;

NMR Spectrum: 1.8–2.1 (m, 4H), 2.99 (s, 3H), 3.7–3.9 (m, 4H), 6.8–7.6 (m, 8H), 8.14 (s, 1H);

Elemental Analysis: Found C, 63.0; H, 5.6; N, 3.7; $C_{19}H_{20}FNO_3S$ requires C, 63.1; H, 5.6; N, 3.9%.

The 4-[5-fluoro-3-(4-methoxytetrahydropyran-4-yl)phenylthio]benzaldehyde used as a starting material was obtained as follows:

A mixture of 4-(5-fluoro-3-mercaptophenyl)-4-methoxytetrahydropyran (2.42 g), potassium hydroxide (0.56 g) and DMF (25 ml) was stirred and heated to 140° C. until a clear solution was obtained. 4-Bromobenzaldehyde (2.78 g) and cuprous oxide (0.715 g) were added and the mixture was stirred and heated to 140° C. for 90 minutes. The mixture was cooled to ambient temperature and partitioned between diethyl ether and water. The organic phase was washed with brine, dried ($MgSO_4$) and evaporated. The residue was purified by column chromatography using a 4:1 v/v mixture of petroleum ether (b.p. 40°–60° C.) and ethyl acetate as eluent. There was thus obtained the required starting material (2.38 g, 68%), m.p. 93° C.

EXAMPLE 11

Using an analogous procedure to that described in Example 3, except that the reaction mixture was stirred at ambient temperature for 16 hours, 4-[5-fluoro-3-(4-methoxytetrahydropyran-4-yl)phenylthio]benzaldehyde oxime was reacted with methyl iodide to give 4-[5-fluoro-3-(4-methoxytetrahydropyran-4-yl)phenylthio]benzaldehyde oxime O-methyl ether in 41% yield, m.p. 58°–59° C.;

NMR Spectrum: 1.8–2.05 (m, 4H), 2.97 (s, 3H), 3.7–3.9 (m, 4H), 3.97 (s, 3H), 6.8–7.65 (m, 7H), 8.03 (s, 1H);

Elemental Analysis: Found C, 63.6; H, 5.9; N, 3.7; $C_{20}H_{22}FNO_3S$ requires C, 64.0; H, 5.9; N, 3.7%.

EXAMPLE 12

A mixture of 4-[5-fluoro-3-(4-methoxytetrahydropyran-4-yl)phenylthio]benzophenone (0.22 g), hydroxylamine hydrochloride (0.042 g) and pyridine (4 ml) was stirred and heated to reflux for 3 hours. The mixture was cooled to ambient temperature and partitioned between diethyl ether and water. The organic phase was washed with brine, dried ($MgSO_4$) and evaporated. There was thus obtained, as a mixture of (E)- and (Z)-isomers, 4-[5-fluoro-3-(4-methoxytetrahydropran-4-yl)phenylthio]benzophenone oxime as a foam (0.12 g, 53%);

NMR Spectrum: 1.7–2.2 (m, 4H), 2.91 and 2.99 (2 s—s, 3H), 3.7–4.0 (m, 4H), 6.8–7.8 (m, 13H);

Elemental Analysis: Found C, 68.4; H, 5.7; N, 3.3; $C_{25}H_{24}FNO_3S$ requires C, 68.6; H, 5.5; N, 3.2%.

The 4-[5-fluoro-3-(4-methoxytetrahydropyran-4-yl)phenylthio]benzophenone used as a starting material was obtained as follows:

A mixture of 4-(5-fluoro-3-mercaptophenyl)-4-methoxytetrahydropyran (1.07 g), potassium carbonate (1.28 g) and DMF (5 ml) was stirred and heated to 140° C. for 10 minutes. 4-Iodobenzophenone (*J. Chem. Soc. Perkin 1*, 1973, 2940; 1.52 g) and cuprous chloride (0.2 g) were added in turn and the mixture was stirred and heated to 140° C. for 1 hour. The mixture was cooled to ambient temperature and partitioned between diethyl ether and water. The organic phase was washed with brine, dried ($MgSO_4$) and evaporated. The residue was purified by column chromatography using a 19:1 v/v mixture of methylene chloride and diethyl ether as eluent. There was thus obtained the required starting material (1.72 g, 92%) as an oil.

EXAMPLE 13

Using an analogous procedure to that described in Example 3, 4-[5-fluoro-3-(4-methoxytetrahydropyran-4-yl)phenylthio]benzophenone oxime was reacted with methyl iodide to give 4-[5-fluoro-3-(4 -methoxytetrahydropyran-4-yl)phenylthio]benzophenone oxime O-methyl ether in 62% yield as an oil;

NMR Spectrum: 1.75–2.1 (m, 4H), 2.91 and 2.99 (2 s's, 3H), 3.7–3.9 (m, 4H), 3.975 and 3.98 (2 s's, 3H), 6.8–7.6 (m, 12H);

Elemental Analysis: Found C, 68.9; H, 6.0; N, 3.1; $C_{26}H_{26}FNO_3S$ requires C, 69.2; H, 5.8; N, 3.1%.

EXAMPLE 14

A mixture of ethyl 2-{4-[5-fluoro-3-(4-methoxytetrahydropyran-4-yl)phenylthio]phenyl}-2-oxoacetate (0.209 g), hydroxylamine hydrochloride (0.052 g), pyridine (2 ml) and ethanol (2 ml) was stirred and heated to reflux for 2 hours. The mixture was evaporated and the residue was partitioned between ethyl acetate and water. The organic phase was washed with brine, dried ($MgSO_4$) and evaporated. The residue was purified by column chromatography using increasingly polar mixture of petroleum ether (b.p. 40°–60° C.) and ethyl acetate as eluent. There was thus obtained ethyl 2-{4-[5-fluoro-3-(4-methoxytetrahydropyran-4-yl)phenylthio]phenyl}-2-hydroxyiminoacetate as an oil (0.2 g, 92%);

NMR Spectrum: 1.2–1.6 (m, 3H), 1.9–2.15 (m, 4H), 3.0 (s, 3H), 3.8–4.0 (m, 4H), 4.50 (m, 2H), 6.9–7.7 (m, 7H), 8.8 (hump, 1H);

Elemental Analysis: Found C, 60.2; H, 5.9; N, 3.3; $C_{22}H_{24}FNO_5S$. 0.5EtAc requires C, 60.3; H, 5.9; N, 2.9%.

The ethyl 2-{4-[5-fluoro-3-(4-methoxytetrahydropyran-4-yl)phenylthio]phenyl}-2-oxoacetate used as a starting material was obtained as follows:

A mixture of 4-(5-fluoro-3-mercaptophenyl)-4-methoxytetrahydropyran (2.42 g), 1,4-diiodobenzene (4.95 g), potassium carbonate (1.38 g), cuprous chloride (0.5 g) and DMF (30 ml) was stirred and heated to 140° C. for 90 minutes. The mixture was cooled to ambient temperature and partitioned between diethyl ether and water. The organic phase was washed with brine, dried ($MgSO_4$) and evaporated. The residue was purified by column chromatography using a 8:1 v/v mixture of petroleum ether (b.p. 40°–60° C.) and ethyl acetate as eluent. There was thus obtained 4-[5-fluoro-3-(4-iodophenylthio)phenyl]-4-methoxytetrahydropyran (2.73 g, 61%).

n-Butyl-lithium (1.6M in hexane, 1.6 ml) was added dropwise to a stirred solution of a portion (1 g) of the product so obtained in THF (10 ml) which had been cooled to –70° C. and the mixture was stirred at –70° C. for 15 minutes. The solution so obtained was added to a solution of diethyl oxalate (0.994 g) in THF (5 ml) which had been cooled to –70° C. The mixture was allowed to warm to ambient temperature and was stirred at this temperature for 90 minutes. The mixture was partitioned between diethyl ether and water. The organic phase was washed with brine, dried ($MgSO_4$) and evaporated. The residue was purified by column chromatogrpahy using a 6:1 v/v mixture of petroleum ether (b.p. 40°–60° C.) and ethyl acetate as eluent. There was thus obtained the required starting material as an oil (0.44 g, 26%).

EXAMPLE 15

A mixture of 4'-[2-(4-methoxytetrahydropyran-4-yl)thiazol-5-ylthio]acetophenone (0.2 g), hydroxylamine hydrochloride (0.044 g) and pyridine (1.5 ml) was stirred at ambient temperature for 16 hours. The mixture was partitioned between diethyl ether and water. The organic phase was washed with brine, dried ($MgSO_4$) and evaporated. The residue was purified by column chromatography using a 1:1 mixture of petroleum ether and ethyl acetate as eluent. There was thus obtained (E)-4'-[2-(4-methoxytetrahydropyran-4-yl)thiazol-5-ylthio]acetophenone oxime (0.103 g, 50%), m.p. 110° C.;

NMR Spectrum ($CD_3SOCD_3$) 1.9–2.2 (m, 4H), 2.17 (s, 3H), 3.15 (s, 3H), 3.65–3.75 (m, 4H), 7.29 (d, 2H), 7.65 (d, 2H), 8.04 (s, 1H).

The 4'-[2-(4-methoxytetrahydropyran-4-yl)thiazol-5-ylthio]acetophenone used as a starting material was obtained as follows:

A solution of 2-bromothiazole (1 g) in diethyl ether (1 ml) was added dropwise to a stirred solution of n-butyl-lithium (1.6M in hexane, 4.2 ml) which had been cooled to –78° C. The mixture was stirred at that temperature for 30 minutes. A solution of tetrahydropyran-4-one (0.537 ml) in diethyl ether (3 ml) was added. The mixture was stirred at –78° C. for 1 hour and then allowed to warm to ambient temperature. A saturated aqueous ammonium chloride solution was added and the mixture was extracted with diethyl ether. The organic phase was washed with brine, dried ($MgSO_4$) and evaporated. The residue was purified by column chromatography using a 3:1 mixture of diethyl ether and petroleum ether as eluent. There was thus obtained 4-hydroxy-4-(2-thiazolyl)tetrahydropyran (0.7 g, 60%), m.p. 93° C.

Sodium hydride (60% dispersion in mineral oil, 0.097 g) was added to a solution of a portion (0.5 g) of the product so obtained in THF (4 ml) and the mixture was stirred at ambient temperature for 30 minutes. The mixture was cooled to 0° C. and methyl iodide (0.84 ml) was added. The mixture was stirred for 4 hours and allowed to warm to ambient temperature. The mixture was partitioned between diethyl ether and brine. The organic phase was dried ($MgSO_4$) and evaporated. The residue was purified by column chromatography using a 3:1 mixture of diethyl ether and petroleum ether as eluent. There was thus obtained 4-methoxy-4-(2-thiazolyl)tetrahydropyran (0.439 g, 82%) as an oil.

A solution of the product so obtained (0.5 g) in THF (1 ml) was added to a stirred solution of n-butyl-lithium (1.6M in hexane, 1.73 ml) which had been cooled to –78° C. The mixture was stirred at –78° C. for 3 hours. A solution of di-[4-(2-methyl-1,3-dioxolan-2-yl)phenyl]disulphide (0.98 g) in THF (5 ml) was added. The mixture was stirred at –78° C. for 1 hour and at –40° C. for 1 hour. A saturated aqueous ammonium chloride solution was added and the mixture was extracted with diethyl ether. The organic phase was washed with brine, dried ($MgSO_4$) and evaporated. The residue was purified by column chromatography using a 3:1 mixture of ethyl acetate and petroleum ether as eluent. There was thus obtained 4'-[2-(4-methoxytetrahydropyran- 4-yl)thiazol-5-ylthio]acetophenone ethylene acetal (0.33 g, 34%) as a solid.

A mixture of 2N aqueous hydrochloric acid (4 drops) and acetone (2 ml) was added to a solution of a portion (0.23 g) of the product so obtained in acetone (2 ml) which been cooled to 0° C. The mixture was allowed to warm to ambient temperature and stirred for 24 hours. The mixture was neutralized by the addition of potassium carbonate. The mixture was evaporated and the residue was purified by column chromatography using a 3:1 mixture of ethyl acetate and petroleum ether as eluent. There was thus obtained 4'-[2-(4-methoxytetrahydropyran-4-yl)thiazol-5-ylthio]acetophenone (0.193 g, 95%) as an oil;

NMR Spectrum 2.0–2.1 (m, 2H), 2.2–2.35 (m, 2H), 2.55 (s, 3H), 3.20 (s, 3H), 3.75–3.90 (m, 4H), 7.25–7.3 (m, 2H), 7.85–7.95 (m, 3H).

EXAMPLE 16

Using an analogous procedure to that described in Example 15, 4'-[4-bromo-2-(4-methoxytetrahydropyran-4-yl)thiazol-5-ylthio]acetophenone was reacted with hydroxylamine hydrochloride to give (E)-4'-[4-bromo-2-(4-methoxytetrahydropyran-4-yl)thiazol-5-ylthio]acetophenone oxime in 96% yield, m.p. 130° C.;

NMR Spectrum ($CD_3SOCD_3$) 1.8–2.2 (m, 4H), 2.14 (s, 3H), 3.18 (s, 3H), 3.6–3.8 (m, 4H), 7.25–7.35 (d, 2H), 7.63–7.73 (d, 2H), 11.25 (s, 1H).

The 4'-[4-bromo-2-(4-methoxytetrahydropyran-4-yl)thiazol-5-ylthio] acetophenone used as a starting material was obtained as follows:

Using analogous procedures to those described in the first two paragraphs of the portion of Example 15 which is concerned with the preparation of starting materials, 2,4-dibromothiazole (*Bull. Soc. Chim. Fr.*, 1962, 1735) was converted into 4-(4-bromothiazole-2-yl)-4-methoxytetrahydropyran in 64% yield as an oil.

A solution of the product so obtained (0.35 g) in THF (2 ml) was added to a stirred solution of n-butyl-lithium (1.6M in hexane, 0.87 ml) which had been cooled to −78° C. The mixture was stirred at −78° C. for 2 hours. A solution of di-[4-(2-methyl-1,3-dioxolan-2-yl)phenyl]disulphide (0.49 g) in THF (4 ml) was added very slowly. The mixture was stirred at −78° C. for 2 hours and at 20° C. for 1.5 hours. A saturated aqueous ammonium chloride solution was added and the mixture was extracted with diethyl ether. The organic phase was washed with brine, dried ($MgSO_4$) and evaporated. The residue was purified by column chromatography using a 11:9 mixture of ethyl acetate and petroleum ether as eluent. There was thus obtained 4'-[4-bromo-2-(4-methoxytetrahydropyran-4-yl)thiazol-5-ylthio]acetophenone ethylene acetal (0.186 g, 40%), m.p. 71° C.

Using an analogous procedure to that described in the last paragraph of the portion of Example 15 which is concerned with the preparation of starting materials, the acetophenone ethylene acetal so obtained was converted into 4'-[4-bromo-2-(4-methoxytetrahydropyran-4-yl)thiazol-5-ylthio]acetophenone in 95% yield, m.p. 116°–118° C.;

NMR Spectrum 1.99–2.02 (m, 2H), 2.2–2.27 (m, 2H), 2.57 (s, 3H), 3.24 (s, 3H), 3.75–3.84 (m, 4H), 7.21–7.26 (d, 2H), 7.87–7.89 (d, 2H).

EXAMPLE 17

The procedure described in Example 15 was repeated except that O-methylhydroxylamine hydrochloride was used in place of hydroxylamine hydrochloride. There was thus obtained (E)-4'-[2-(4-methoxytetrahydropyran-4-yl)thiazol-5-ylthio]acetophenone oxime O-methyl ether in 47% yield as an oil.

NMR Spectrum ($CD_3SOCD_3$) 2.0–2.2 (m, 4H), 2.25 (s, 3H), 3.20 (s, 3H), 3.65–3.80 (m, 4H), 4.0 (s, 3H), 7.3–7.4 (d, 2H), 7.7–7.8 (d, 2H), 8.1 (s, 1H).

EXAMPLE 18

Sodium hydride (60%, 0.024 g) was added to a stirred solution of (E)-4'-[2-(4-methoxytetrahydropyran-4-yl)thiazol-5-ylthio]acetophenone oxime (0.18 g) in THF (2 ml). The mixture was stirred at ambient temperature for 30 minutes. The mixture was cooled to 0° C. and bromoacetonitrile (0.178 g) was added. The mixture was stirred and allowed to warm to ambient temperature. The mixture was evaporated and the residue was partitioned between diethyl ether and water. The organic phase was washed with brine, dried ($MgSO_4$) and evaporated. The residue was purified by column chromatography using a 1:1 mixture of petroleum ether and ethyl acetate as eluent. There was thus obtained (E)-4'-[2-(4-methoxytetrahydropyran-4-yl)thiazol-5-ylthio] acetophenone oxime O-cyanomethyl ether as an oil in 93% yield;

NMR Spectrum 2.0–2.1 (m, 2H), 2.2–2.3 (s & m, 5H), 3.15 (s, 3H), 3.75–3.9 (m, 4H), 4.81 (s, 2h), 7.22 (d, 2H), 7.59 (d, 2H), 7.82 (s, 1H).

EXAMPLE 19

Using an analogous procedure to that described in Example 15, 4'-[2-(4-methoxytetrahydropyran-4-yl)thiazol-4-ylthio]acetophenone was reacted with hydroxylamine hydrochloride to give (E)-4'-[2-(4-methoxytetrahydropyran-4-yl)thiazol-4-ylthio]acetophenone oxime in 95% yield, m.p. 89° C.;

NMR Spectrum 2.0–2.1 (m, 2H), 2.2–2.35 (s & m, 5H), 3.20 (s, 3H), 3.75–3.9 (m, 4H), 7.25 (d, 2H), 7.55 (d, 2H), 7.82 (s, 1H), 8.5 (broad hump, 1H).

The 4'-[2-(4-methoxytetrahydropyran-4-yl)thiazol-4-ylthio]acetophenone used as a starting material was obtained as follows:

A solution of 4-(4-bromothiazole-2-yl)-4-methoxytetrahydropyran (0.35 g) in THF (2 ml) was added dropwise to a stirred solution of n-butyl-lithium (1.6M in hexane, 0.87 ml) which had been cooled to −78° C. The mixture was stirred at −78° C. for 2 hours. A solution of di-[4-(2-methyl-1,3-dioxolan-2-yl)phenyl]disulphide (0.49 g) in THF (4 ml) was added dropwise. The mixture was stirred at −78° C. for 3 hours and at −20° C. for 1.5 hours. A saturated aqueous ammonium chloride solution was added and the mixture was extracted with diethyl ether. The organic phase was washed with brine, dried ($MgSO_4$) and evaporated. The residue was purified by column chromatography using a 11:9 mixture of ethyl acetate and petroleum ether as eluent. There was thus obtained 4'-[2-(4-methoxytetrahydropyran-4-yl)thiazol-4-ylthio]acetophenone ethylene acetal (0.1 g, 20%) as a solid.

Using an analogous procedure to that described in the last paragraph of the portion of Example 15 which is concerned with the preparation of starting materials, the ethylene acetal so obtained was converted into 4'-[2-(4-methoxytetrahydropyran-4-yl)thiazol-4-ylthio]acetophenone in 89% yield as an oil;

NMR Spectrum 2.0–2.1 (m, 2H), 2.2–2.3 (m, 2H), 2.56 (s, 3H), 3.21 (s, 3H), 3.8–3.85 (m, 4H), 7.21 (d, 2H), 7.86 (m, 3H).

EXAMPLE 20

Using an analogous procedure to that described in Example 15, 4'-[5-(4-methoxytetrahydropyran-4-yl)thiazol- 2-ylthio]acetophenone was reacted with hydroxylamine hydrochloride to give (E)-4'-[5-(4-methoxytetrahydropyran-4-yl)thiazol-2 -ylthio]acetophenone oxime in 80% yield, m.p. 114°–116° C.;

NMR Spectrum (CD$_3$SOCD$_3$) 1.85–2.05 (m, 4H), 2.30 (s, 3H), 2.90 (s, 3H), 3.55–3.75 (m, 4H), 7.55–7.9 (m, 5H), 11.38 (s, 1H).

The 4'-[5-(4-methoxytetrahydropyran-4-yl)thiazol-2-ylthio]acetophenone used as a starting material was obtained as follows:

A mixture of 4'-fluoroacetophenone (6 g), 2-thiazolethiol (3.6 g), potassium carbonate (6 g) and NMP (30 ml) was stirred and heated to 140° C. for 9 hours. The mixture was cooled to ambient temperature and partitioned between diethyl ether and water. The organic phase was washed with brine, dried (MgSO$_4$) and evaporated. The residue was purified by column chromatography using increasingly polar mixtures of petroleum ether and ethyl acetate as eluent. There was thus obtained 4'-(2-thiazolylthio)acetophenone (3.9 g, 54%) as an oil.

A mixture of a portion (0.34 g) of the material so obtained, ethylene glycol (1 ml), triethyl orthoformate (1 ml), 4-toluenesulphonic acid (10 mg) and toluene (5 ml) was stirred and heated to 40° C. for 2 hours. The mixture was cooled to ambient temperature and partitioned between diethyl ether and a saturated aqueous ammonium chloride solution. The organic phase was washed with brine, dried (MgSO$_4$) and evaporated. The residue was purified by column chromatography using a 17:3 mixture of petroleum ether and ethyl acetate as eluent. There was thus obtained 4'-(2-thiazolylthio)acetophenone ethylene acetal (0.29 g, 72%) as an oil.

A solution of a portion (0.264 g) of the material so obtained in THF (1 ml) was added dropwise to a stirred mixture of n-butyl-lithium (1.6M in hexane, 0.7 ml) and THF (1 ml) which had been cooled to −78° C. A solution of tetrahydropyran-4-one (0.1 g) in THF (1 ml) was added dropwise and the mixture was stirred at −78° C. for 1 hour. The mixture was allowed to warm to ambient temperature and partitioned between ethyl acetate and a saturated aqueous ammonium chloride solution. The organic solution was washed with brine, dried (MgSO$_4$) and evaporated. The residue was purified by column chromatography using a 1:3 mixture of petroleum ether and ethyl acetate as eluent. There was thus obtained 4'-[5-(4-hydroxytetrahydropyran-4-yl)thiazol-2-ylthio] acetophenone ethylene acetal (0.1 g), m.p. 116°–120° C.

Sodium hydride (60%, 0.04 g) was added to a solution of the material so obtained in THF (2 ml) which had been cooled to 0° C. The mixture was stirred at 0° C. for 1 hour. Methyl iodide (0.168 ml) was added and the mixture was stirred at 0° C. for 1 hour. The mixture was partitioned between ethyl acetate and a saturated aqueous ammonium chloride solution. The organic phase was washed with brine, dried (MgSO$_4$) and evaporated. The residue was purified by column chromatography using a 1:1 mixture of petroleum ether and ethyl acetate as eluent. There was thus obtained 4'-[5-(4-methoxytetrahydropyran-4-yl)thiazol-2-ylthio] acetophenone ethylene acetal (0.08 g, 74%) as an oil.

A solution of 2N aqueous hydrochloric acid (1 drop) in acetone (1 ml) was added to a solution of the ethylene acetal so obtained in acetone (1 ml) which had been cooled to 0° C. The mixture was stirred at ambient temperature for 16 hours. The mixture was neutralized by the addition of potassium carbonate (0.02 g) and evaporated. The residue was purified by column chromatography using a 3:1 mixture of diethyl ether and petroleum ether as eluent. There was thus obtained 4'-[5-(4-methoxytetrahydropyran-4-yl)thiazol-2-ylthio]acetophenone (0.063 g, 89%), m.p. 105°–106° C.;

NMR Spectrum 1.9–2.15 (m, 4H), 2.6 (s, 3H), 3.1 (s, 3H), 3.65–3.9 (m, 4H), 7.5–7.7 (m, 3H), 7.85–8.05 (m, 2H).

EXAMPLE 21

Using an analogous procedure to that described in Example 15, 4'-[4-(4-methoxytetrahydropyran-4-yl)thiazol-2-ylthio]acetophenone was reacted with hydroxylamine hydrochloride to give (E)-4'-[4-(4-methoxytetrahydropyran-4-yl)thiazol-2-ylthio]acetophenone oxime in 90% yield, m.p. 146° C.;

NMR Spectrum (CD$_3$SOCD$_3$) 1.9–2.1 (m, 4H), 2.16 (s, 3H), 2.95 (s, 3H), 3.5–3.7 (m, 4H), 7.57 (s, 1H), 7.64 (d, 2H), 7.76 (d, 2H).

The 4'-[4-(4-methoxytetrahydropyran-4-yl)thiazol-2-ylthio]acetophenone used as a starting material was obtained as follows:

4'-Mercaptoacetophenone ethylene acetal (0.656 g; obtained by the reaction of 4'-mercaptoacetophenone and ethylene glycol using an analogous procedure to that described in the third paragraph of the portion of Example 7 which is concerned with the preparation of starting materials) was added to a mixture of 2,4-dibromothiazole (0.82 g), potassium carbonate (0.468 g) and NMP (4 ml). The mixture was stirred and heated to 90° C. for 2.5 hours. The mixture was cooled to ambient temperature and partitioned between diethyl ether and brine. The organic phase was dried (MgSO$_4$) and evaporated. The mixture was purified by column chromatography using a 3:1 mixture of ethyl acetate and petroleum ether as eluent. There was thus obtained 4'-[4-bromothiazole-2-ylthio]acetophenone ethylene acetal (1.1 g, 90%), m.p. 71° C.

A solution of n-butyl-lithium (1.6M in hexane, 0.87 ml) was added to a solution of a portion (0.5 g) of the ethylene acetal so obtained in diethyl ether (3 ml) which had been cooled to −78° C. The mixture was stirred at −78° C. for 2 hours. A solution of tetrahydropyran-4-one (0.128 ml) in diethyl ether (1 ml) was added. The mixture was stirred at −78° C. for 1 hour and at −40° C. for 1 hour. A saturated aqueous ammonium chloride solution was added and the mixture was extracted with diethyl ether. The organic phase was washed with brine, dried (MgSO$_4$) and evaporated. The residue was purified by column chromatography using a 1:1 mixture of petroleum ether and ethyl acetate as eluent. There was thus obtained 4'-[4-(4-hydroxytetrahydropyran-4-yl)thiazol-2-ylthio]acetophenone ethylene acetal (0.34 g, 64%), m.p. 112° C.

Using analogous procedures to those described in the second and fourth paragraphs of the portion of Example 15 which is concerned with the preparation of starting materials, the ethylene acetal so obtained was converted into 4'-[4-(4-methoxytetrahydropyran-4-yl)thiazol-2-ylthio]acetophenone in 85% yield as a solid, m.p. 141° C.;

NMR Spectrum 1.9–2.2 (m, 4H), 2.55 (s, 3H), 3.1 (s, 3H), 3.6–3.9 (m, 4H), 7.15 (s, 1H), 7.45–7.55 (d, 2H), 7.85–8.0 (d, 2H).

EXAMPLE 22 using an analogous procedure to that described in Example 2, (Z)-4'-[4-(4-methoxytetrahydropyran-4-yl)thien-2-ylthio]acetophenone oxime was reacted with bromoacetonitrile to give (Z)-4'-[4-(4-methoxytetrahydropyran-4-yl)thien-2-ylthio] acetophenone oxime O-cyanomethyl ether in 72% yield, m.p. 105°–110° C.;

NMR Spectrum 1.95–2.1 (m, 4H), 2.20 (s, 3H), 3.08 (s, 3H), 3.75–3.9 (m, 4H), 4.68 (s, 2H), 7.1–7.4 (m, 6H).

EXAMPLE 23

Sodium hydride (60%, 0.109 g) was added to a stirred solution of (E)-4'-[4-(4-methoxytetrahydropyran-4-yl)thien-2-ylthio)acetophenone oxime (0.54 g) in DMF (6 ml) and the mixture was stirred at ambient temperature for 30 minutes. 3-Chloromethylpyridine hydrochloride (0.27 g) and sodium iodide (0.045 g) were added in turn and the mixture was stirred at ambient temperature for 16 hours. The mixture was partitioned between ethyl acetate and water. The organic phase was dried (MgSO$_4$) and evaporated. The residue was purified by column chromatography using a 9:1 mixture of ethyl acetate and petroleum ether as eluent. There was thus obtained (E)-4'-[4-(4-methoxytetrahydropyran-4-yl)thien-2-ylthio]acetophenone oxime O-(3-pyridyl)methyl ether in 38% yield, m.p. 78°–79° C.;

NMR Spectrum 1.95–2.1 (m, 4H), 2.22 (s, 3H), 3.05 (s, 3H), 3.7–3.9 (m, 4H), 5.21 (s, 2H), 7.16 (d, 2H), 7.25 (d, 2H), 7.54 (d, 2H), 7.72 (d, 1H), 8.57 (m, 1H), 8.68 (s, 1H).

EXAMPLE 24

Using an analogous procedure to that described in Example 2, (E)-4'-[4-(4-methoxytetrahydropyran-4-yl)thien-2-ylthio]acetophenone oxime was reacted with 4-chloromethylpyridine hydrochloride to give (E)-4'-[4-(4-methoxytetrahydropyran-4-yl)thien-2-ylthio]acetophenone oxime O-(4-pyridyl)methyl ether in 86% yield as an oil;

NMR Spectrum 1.95–2.05 (m, 4H), 2.26 (s, 3H), 3.03 (s, 3H), 3.74–3.84 (m, 4H), 5.22 (s, 2H), 7.14 (d, 2H), 7.26 (m, 4H), 7.52 (d, 2H), 8.57 (d, 2H).

EXAMPLE 25

A mixture of 3'-[5-fluoro-3-(4-methoxytetrahydropyran-4-yl)phenylthio]acetophenone (0.238 g), hydroxylamine hydrochloride (0.06 g) and pyridine (3 ml) was stirred and heated to 80° C. for 5 hours. The mixture was cooled to ambient temperature and partitioned between ethyl acetate and water. The organic phase was washed with brine, dried (MgSO$_4$) and evaporated. The residue was purified by column chromatography using a 5:1 mixture of petroleum ether and ethyl acetate as eluent. There was thus obtained 3'-[5-fluoro-3-(4 -methoxytetrahydropyran-4-yl)phenylthio] acetophenone oxime (0.18 g, 72%) as an oil;

NMR Spectrum 1.7–2.1 (m, 4H), 2.24 (s, 3H), 2.93 (s, 3H), 3.6–4.0 (m, 4H), 6.7–7.7 (m, 7H), 7.8 (broad s, 1H).

The 3'-[5-fluoro-3-(4-methoxytetrahydropyran-4-yl)phenylthio]acetophenone used as a starting material was obtained as follows:

Potassium tert-butoxide (0.45 g) and tetrakis(triphenylphosphine)palladium(O) (0.37 g) were added in turn to a stirred solution of 4-(5-fluoro-3-mercaptophenyl)-4-methoxytetrahydropyran (1 g) in DMSO (10 ml). The mixture was stirred at ambient temperature for 30 minutes. 3'-Bromoacetophenone (2.39 g) was added and the mixture was heated to 130° C. for 3 hours. The mixture was cooled to ambient temperature and partitioned between ethyl acetate and water. The organic phase was washed with brine, dried (MgSO$_4$) and evaporated. The residue was purified by column chromatography using a 5:1 mixture of petroleum ether and ethyl acetate as eluent. There was thus obtained the required starting material in 70% yield as an oil.

EXAMPLE 26

Using an analogous procedure to that described in Example 25, 4'-{5-fluoro-3-[(2S,4R)-4-methoxy-2-methyltetrahydropyran-4-yl]phenylthio}acetophenone was reacted with hydroxylamine hydrochloride to give (E)-4'-{5-fluoro-3-[(2S,4R)-4-methoxy-2-methyltetrahydropyran-4-yl]phenylthio}acetophenone oxime in 66% yield, m.p. 105° C.;

NMR Spectrum 1.20 (d, 3H), 1.52 (m, 1H), 1.85–1.96 (m, 3H), 2.27 (s, 3H), 3.0 (s, 3H), 3.8–3.94 (m, 3H), 6.86 (d, 1H), 6.95 (d, 1H), 7.15 (s, 1H), 7.38 (d, 2H), 7.62 (d, 2H), 7.93 (broad s, 1H).

The 4'-{5-fluoro-3-[(2S,4R)-4-methoxy-2-methyltetrahydropyran-4-yl]phenylthio}acetophenone used as a starting material was obtained as follows:

A mixture of di-[4-(2-methyl-1,3-dioxolan-2-yl)phenyl] disulphide (2 g), triphenylphosphine (1.41 g), water (3 ml) and 1,4-dioxan (20 ml) was stirred and heated to 70° C. for 7 hours. The mixture was evaporated and the residue was partitioned between diethyl ether and 1N aqueous sodium hydroxide solution. The aqueous phase was acidified to pH6 by the addition of 6N aqueous hydrochloric acid and extracted with diethyl ether. The organic phase was washed with brine, dried (MgSO$_4$) and evaporated. There was thus obtained 4-(2-methyl-1,3-dioxolan-2-yl)benzenethiol (1.4 g, 70%) as an oil.

A mixture of a portion (0.206 g) of the thiol so obtained, (2S,4R)-4-(3,5-difluorophenyl)-4-methoxy-2-methyltetrahydropyran [European Patent Application No. 0462813 (Example 10 thereof); 0.242 g], lithium hydroxide monohydrate (0.045 g) and NMP (2 ml) was stirred and heated to 140° C. for 2.5 hours. The mixture was cooled to ambient temperature and partitioned between ethyl acetate and water. The organic phase was washed with brine, dried (MgSO$_4$) and evaporated. The residue was purified by column chromatography using increasingly polar mixtures of petroleum ether and ethyl acetate as eluent. There was thus obtained (2S,4R)-4-{5-fluoro-3-[4-(2-methyl-1,3-dioxolan-2-yl)phenylthio]phenyl}-4-methoxy-2-methyltetrahydropyran (0.22 g, 52%) as an oil.

A solution of 2N aqueous hydrochloric acid (2 drops) was added to a solution of the product so obtained in acetone (5 ml). The mixture was stirred at ambient temperature for 4 hours. The mixture was neutralized by the addition of sodium bicarbonate. The mixture was evaporated and the residue was partitioned between ethyl acetate and water. The organic phase was washed with brine, dried (MgSO$_4$) and evaporated. The residue was purified by column chromatography using a 5:1 mixture of petroleum ether and ethyl acetate as eluent. There was thus obtained 4'-{5-fluoro-3-[(2S,4R)-4-methoxy-2-methyltetrahydropyran-4-yl] phenylthio]acetophenone (0.167 g, 89%) as an oil.

EXAMPLE 27

A mixture of 4'-[5-fluoro-3-(4-methoxytetrahydropyran-4-yl)phenoxymethyl]acetophenone (0.341 g), hydroxylamine hydrochloride (0.076 g) and pyridine (7 ml) was stirred and heated to reflux for 2 hours. The mixture was cooled to ambient temperature and partitioned between diethyl ether and 6N aqueous hydrochloric acid. The organic phase was washed with brine, dried (MgSO$_4$) and evaporated. The residue was recrystallized from methylene chloride. There was thus obtained (E)-4'-[5-fluoro-3-(4-methoxytetrahydropyran-4-yl)phenoxymethyl]acetophenone oxime (0.136 g, 38%), m.p. 156°–157° C.;

NMR Spectrum 1.92–2.2 (m, 4H), 2.29 (s, 3H), 2.98 (s, 3H), 3.75–4.05 (m, 4H), 5.08 (s, 2H), 6.5–6.95 (m, 3H), 7.3–7.8 (m, 4H), 8.15 (broad s, 1H).

The 4'-[5-fluoro-3-(4-methoxytetrahydropyran-4-yl)phenoxymethyl]acetophenone used as a starting material was obtained as follows:

A mixture of 4'-bromomethylacetophenone (0.305 g; prepared by heating a mixture of 4'-methylacetophenone, N-bromosuccinimide, azobisisobutyronitrile and carbon tetrachloride to 40° C. for 4 hours), 4-(5-fluoro-3-hydroxyphenyl)-4-methoxytetrahydropyran (0.3 g; European Patent Application No. 0385662, Example 2 thereof), potassium carbonate (0.192 g) and DMF (10 ml) was stirred at ambient temperature for 16 hours. The mixture was partitioned between diethyl ether and water. The organic phase was washed with brine, dried (MgSO$_4$) and evaporated. The residue was purified by column chromatography using a 4:1 mixture of petroleum ether and ethyl acetate as eluent. There was thus obtained the required starting material (0.341 g, 73%) as a solid, m.p. 75°–76° C.

EXAMPLE 28

Using an analogous procedure to that described in Example 7, 4'-[5-fluoro-3-(4-methoxytetrahydropyran-4-yl)phenylthio]-2'-methoxyacetophenone was reacted with hydroxylamine hydrochloride to give (E)-4'-[5-fluoro-3-(4-methoxytetrahydropyran-4-yl)phenylthio]-2'-methoxyacetophenone oxime in 52% yield, m.p. 155° C.;

NMR Spectrum 1.85–2.0 (m, 4H), 2.22 (s, 3H), 2.98 (s, 3H), 3.74–3.86 (m, 4H), 3.80 (s, 3H), 6.85–7.0 (m, 4H), 7.18 (s, 1H), 7.29 (m, 1H), 8.1 (broad s, 1H).

The 4'[5-fluoro-3-(4-methoxytetrahydropyran-4-yl)phenylthio]-2'-methoxyacetophenone used as a starting material was obtained as follows:

Using an analogous procedure to that described in the portion of Example 25 which is concerned with the preparation of starting materials, 4'-bromo-2'-methoxyacetophenone was reacted with 4-(5-fluoro-3-mercaptophenyl)-4-methoxytetrahydropyran to give the required starting material in 59% yield as a solid, m.p. 74°–75° C.

The 4'-bromo-2'-methoxyacetophenone used as a starting material was obtained as follows:

Concentrated sulphuric acid (2 ml) was added to a stirred mixture of 3-bromophenol (67 g) and acetic anhydride (20 ml). The mixture was stirred at ambient temperature for 4 hours and evaporated. Ice was added and the mixture was extracted with diethyl ether. The organic phase was dried (MgSO$_4$) and evaporated to give 3-bromophenyl acetate (75.4 g, 90%).

A mixture of a portion (70 g) of the material so obtained and aluminum chloride (131 g) was stirred and heated gradually to 170° C. The mixture was stirred at this temperature for 3.5 hours. The hot mixture was poured onto ice and the resultant mixture was extracted with diethyl ether. The extract was dried (MgSO$_4$) and evaporated. The residue was purified by column chromatography using a 9:1 mixture of petroleum ether and ethyl acetate as eluent. There was thus obtained 4'-bromo-2'-hydroxyacetophenone (66.7 g, 95%), m.p. 33°–40° C.

A mixture of a portion (1 g) of the product so obtained, methyl iodide (0.49 ml), potassium carbonate (0.69 g) and DMF (5 ml) was stirred at ambient temperature for 16 hours. The mixture was partitioned between ethyl acetate and water. The organic phase was dried (MgSO$_4$) and evaporated. The residue was purified by column chromatography using methylene chloride as eluent. There was thus obtained 4'-bromo-2'-methoxyacetophenone (1 g, 96%), m.p. 56°–57° C.

EXAMPLE 29

Using an analogous procedure to that described in Example 7, 2'-benzyloxy-4'-[5-fluoro-3-(4-methoxytetrahydropyran-4-yl)phenylthio]acetophenone was reacted with hydroxylamine hydrochloride to give (E)-2'-benzyloxy-4'-[5-fluoro-3-(4 -methoxytetrahydropyran-4-yl)phenylthio] acetophenone oxime in 47% yield, m.p. 130°–131° C.;

NMR Spectrum 1.8–2.0 (m, 4H), 2.23 (s, 3H), 2.99 (s, 3H), 2.7–3.95 (m, 4H), 5.03 (s, 2H), 6.8–7.4 (m, 11H), 7.6 (broad s, 1H).

The 2'-benzyloxy-4'-[5-fluoro-3-(4-methoxytetrahydropyran-4-yl)phenylthio]acetophenone used as a starting material was obtained as follows:

Using an analogous procedure to that described in the portion of Example 25 which is concerned with the preparation of starting materials, 2'-benzyloxy-4'-bromoacetophenone was reacted with 4-(5-fluoro-3-mercaptophenyl)-4-methoxytetrahydropyran to give the required starting material in 31% yield as an oil.

The 2'-benzyloxy-4'-bromoacetophenone used as a starting material was obtained as follows:

A mixture of 4'-bromo-2'-hydroxyacetophenone (3 g), benzyl bromide (1.82 ml), potassium carbonate (2.1 g) and DMF (15 ml) was stirred at ambient temperature for 16 hours. The mixture was partitioned between diethyl ether and water. The organic phase was dried (MgSO$_4$) and evaporated. The residue was purified by column chromatography using methylene chloride as eluent. There was thus obtained the required starting material (4.1 g, 96%), m.p. 75°–76° C.

EXAMPLE 30

Using an analogous procedure to that described in Example 7, 4'-[5-fluoro-3-(4-methoxytetrahydropyran-4-yl)phenylthio]-2'-hydroxyacetophenone was reacted with hydroxylamine hydrochloride to give (E)-4'-[5-fluoro-3-(4-methoxytetrahydropyran-4-yl)phenylthio]-2'-hydroxyacetophenone oxime in 77% yield, m.p. 140°–142° C.;

NMR Spectrum 1.85–2.0 (m, 4H), 2.32 (s, 3H), 2.98 (s, 3H), 3.75–3.85 (m, 4H), 6.8–7.05 (m, 4H), 7.15–7.40 (m, 2H), 7.60 (s, 1H).

The 4'-[5-fluoro-3-(4-methoxytetrahydropyran-4-yl)phenylthio]-2'-hydroxyacetophenone used as a starting material was obtained as follows:

Using an analogous procedure to that described in the portion of Example 25 which is concerned with the preparation of starting materials, 4'-bromo-2'-tert-butyldimethylsilyloxyacetophenone was reacted with 4-(5-fluoro-3-mercaptophenyl)-4-methoxytetrahydropyran to give the required starting material in 44% yield as an oil.

The 4'-bromo-2'-tert-butyldimethylsilyloxyacetophenone was obtained as follows:

A mixture of 4'-bromo-2'-hydroxyacetophenone (2.15 g), tert-butyldimethylsilyl chloride (3.0 g), imidazole (2.72 g) and DMF (5 ml) was stirred at ambient temperature for 16 hours. The mixture was partitioned between ethyl acetate and water. The organic phase was dried (MgSO$_4$) and evaporated. The residue was purified by column chromatography using a 91:9 mixture of petroleum ether and ethyl acetate as eluent. There was thus obtained the required material in 90% yield as an oil.

EXAMPLE 31

Acetyl chloride (0.072 ml) was added dropwise to a stirred mixture of (E)-4'-[5-fluoro-3-(4-methoxytetrahydropyran-4-yl)phenylthio]acetophenone oxime (0.187 g), pyridine (0.082 ml) and THF (5 ml) which had been cooled to 0° C. The mixture was allowed to warm to ambient temperature and stirred at that temperature for 5 hours. The mixture was partitioned between ethyl acetate and water. The organic phase was washed with brine, dried (MgSO$_4$) and evaporated. The residue was purified by column chromatography using increasingly polar mixtures of petroleum ether and ethyl acetate as eluent. There was thus obtained O-acetyl-(E)-4'-[5-fluoro-3-(4-methoxytetrahydropyran-4-yl)phenylthio]acetophenone oxime (0.15 g, 72%), m.p. 92° C.;

NMR Spectrum 1.85–2.0 (m, 4H), 2.26 (s, 3H), 2.39 (s, 3H), 2.98 (s, H), 3.74–3.90 (m, 4H), 6.95–7.02 (m, 2H), 7.12–7.36 (m, 3H), 7.70 (d, 2H).

EXAMPLE 32

Sodium hydride (60%, 0.03 g) was added to a stirred mixture of (E)-4'-[5-fluoro-3-(4-methoxytetrahydropyran-4-yl)phenylthio]acetophenone oxime (0.19 g), 15-crown-5 (2 drops) and THF (4 ml). The mixture was stirred at ambient temperature for 10 minutes. Pivaloyl chloride (0.09 g) was added and the mixture was stirred at ambient temperature for 4 hours. The mixture was partitioned between ethyl acetate and water. The organic phase was washed with brine, dried (MgSO$_4$) and evaporated. The residue was purified by column chromatography using a 5:1 mixture of petroleum ether and ethyl acetate as eluent. There was thus obtained O-pivaloyl-(E)-4'-[5-fluoro-3-(4-methoxytetrahydropyran-4-yl)phenylthio]acetophenone oxime (0.16 g, 70%) as an oil.

NMR Spectrum 1.34 (s, 9H), 1.8–2.0 (m, 4H), 2.38 (s, 3H), 2.98 (s, 3H), 3.78–3.90 (m, 4H), 6.8–7.0 (m, 2H), 7.17 (d, 1H), 7.28–7.38 (m, 2H), 7.70–7.75 (m, 2H).

EXAMPLE 33

Using an analogous procedure to that described in Example 32, (E)-4'-[5-fluoro-3-(4-methoxytetrahydropyran-4-yl)phenylthio] acetophenone oxime was reacted with methyl 2-bromo-2-methylpropanoate to give (E)-4'-[5-fluoro-3-(4-methoxytetrahydropyran-4-yl)phenylthio] acetophenone oxime O-(1-methoxycarbonyl-1-methylethyl)ether in 88% yield as an oil;

NMR Spectrum 1.57 (s, 6H), 1.7–2.0 (m, 4H), 2.25 (s, 3H), 2.98 (s, 3H), 3.72 (s, 3H), 3.7–3.9 (m, 4H), 6.6–7.8 (m, 7H).

EXAMPLE 34

Using an analogous procedure to that described in Example 32, (E)-4'-[5-fluoro-3-(4-methoxytetrahydropyran-4-yl)phenylthio]acetophenone oxime was reacted with N,N-dimethylcarbamoyl chloride to give O-(N,N-dimethylcarbamoyl)-(E)-4'-[5-fluoro-3-(4-methoxytetrahydropyran-4-yl)phenylthio]acetophenone oxime in 73% yield as an oil;

NMR Spectrum 1.8–2.0 (m, 4H), 2.36 (s, 3H), 2.98 (s, 3H), 3.04 (s, 6H), 3.78–3.90 (m, 4H), 6.85–7.0 (m, 2H), 7.16 (d, 1H), 7.3–7.38 (m, 2H), 7.72–7.75 (m, 2H).

EXAMPLE 35

Using an analogous procedure to that described in Example 32, (E)-4'-[5-fluoro-3-(4-methoxytetrahydropyran-4-yl)phenylthio]acetophenone oxime was reacted with isopropyl bromide to give (E)-4'-[5-fluoro-3-(4-methoxytetrahydropyran-4-yl)phenylthio]acetophenone oxime O-isopropyl ether in 88% yield as an oil;

NMR Spectrum 1.30 (d, 6H), 1.7–2.05 (m, 4H), 2.18 (s, 3H), 2.96 (s, 3H), 3.65–3.95 (m, 4H), 4.2–4.7 (m, 1H), 6.7–7.8 (m, 7H).

EXAMPLE 36

Using an analogous procedure to that described in Example 32, (E)-4'-[5-fluoro-3-(4-methoxytetrahydropyran-4-yl)phenylthio]acetophenone oxime was reacted with 2-chloromethylpyridine hydrochloride in the presence of 4 equivalents of sodium hydride. There was thus obtained (E)-4'-[5-fluoro-3-(4-methoxytetrahydropyran-4-yl)phenylthio]acetophenone oxime O-(2-pyridyl)methyl ether in 45% yield as an oil;

NMR Spectrum 1.85–2.0 (m, 4H), 2.3 (s, 3H), 2.98 (s, 3H), 3.78–3.85 (m, 4H), 5.38 (s, 2H), 6.8–7.7 (m, 10H), 8.59 (m, 1H).

EXAMPLE 37

Using an analogous procedure to that described in Example 32, (E)-4'-[5-fluoro-3-(4-methoxytetrahydropyran-4-yl)phenylthio]acetophenone oxime was reacted with 3-chloromethylpyridine hydrochloride in the presence of 2 equivalents of sodium hydride. There was thus obtained (E)-4'-[5-fluoro-3-(4-methoxytetrahydropyran-4-yl)phenylthio]acetophenone oxime O-(3-pyridyl)methyl ether in 65% yield as an oil;

NMR Spectrum 1.75–2.05 (m, 4H), 2.25 (s, 3H), 2.98 (s, 3H), 3.7–3.95 (m, 4H), 5.29 (s, 2H), 6.7–7.8 (m, 9H), 8.5–8.8 (m, 2H).

EXAMPLE 38

Using an analogous procedure to that described in Example 32, (E)-4'-[5-fluoro-3-(4-methoxytetrahydropyran-4-yl)phenylthio]acetophenone oxime was reacted with 4-chloromethylpyridine hydrochloride in the presence of 4 equivalents of sodium hydride. There was thus obtained (E)-4'-[5-fluoro-3-(4-methoxytetrahydropyran-4-yl)phenylthio]acetophenone oxime O-(4-pyridyl)methyl ether in 70% yield as an oil;

NMR Spectrum 1.8–2.0 (m, 4H), 2.31 (s, 3H), 2.98 (s, 3H), 3.75–3.85 (m, 4H), 5.25 (s, 2H), 6.8–7.65 (m, 9H), 8.58 (m, 2H).

EXAMPLE 39

Using an analogous procedure to that described in Example 32, (E)-4'-[5-fluoro-3-(4-methoxytetrahydropyran-4-yl)phenylthio]acetophenone oxime with reacted with methyl 5-bromomethylisoxazole-3-carboxylate to give (E)-4'-[5-fluoro-3-(4-methoxytetrahydropyran-4-yl)phenylthio]acetophenone oxime O-(3-methoxycarbonylisoxazol-5-yl)methyl ether in 44% yield as an oil;

NMR Spectrum 1.8–2.1 (m, 4H), 2.25 (s, 3H), 2.98 (s, 3H), 3.7–3.95 (m, 4H), 3.97 (s, 3H), 5.37 (s, 2H), 6.7–7.8 (m, 8H).

EXAMPLE 40

Using an analogous procedure to that described in Example 32, (E)-4'-[5-fluoro-3-(4-methoxytetrahydropyran-4-yl)phenylthio]acetophenone oxime was reacted with 1,2-dibromoethane to give (E)-4'-[5-fluoro-3-(4-methoxytetrahydropyran-4-yl)phenylthio]acetophenone oxime O-(2-bromoethyl) ether in 45% yield as an oil.

5-Methyl-2-thiadiazolethiol (0.058 g) was added to a mixture of the product so obtained (0.21 g), sodium bicarbonate (0.037 g) and DMF (3 ml). The mixture was stirred at ambient temperature for 20 hours. The mixture was partitioned between ethyl acetate and water. The organic phase was washed with brine, dried (MgSO$_4$) and evaporated. The residue was purified by column chromatography using increasingly polar mixtures of petroleum ether and ethyl acetate as eluent. There was thus obtained (E)-4'-[5-fluoro-3-(4-methoxytetrahydropyran-4-yl)phenylthio]acetophenone oxime O-[2-(5-methylthiadiazol-2-ylthio)ethyl] ether (0.15 g, 65%) as an oil;

NMR Spectrum 1.7–2.1 (m, 4H), 2.22 (s, 3H), 2.71 (s, 3H), 2.98 (s, 3H), 3.5–4.0 (m, 6H), 4.53 (t, 2H), 6.6–7.8 (m, 7H).

EXAMPLE 41

Using analogous procedures to those described in Example 40, except that 1-methyl-5-tetrazolethiol was used in place of 5-methyl-2-thiadiazolethiol, there was obtained (E)-4'[5-fluoro-3-(4-methoxytetrahydropyran-4-yl)phenylthio]acetophenone oxime O-[2-(1-methyltetrazol-5-ylthio)ethyl]ether in 31% yield as an oil;

NMR Spectrum 1.75–2.05 (m, 4H), 2.2 (s, 3H), 2.98 (s, 3H), 3.6–4.0 (m, 6H), 3.91 (s, 3H), 4.53 (t, 2H), 6.7–7.7 (m, 7H).

EXAMPLE 42

Using analogous procedures to those described in Example 40, except that sodium methanethiolate was used in place of 5-methyl-2-thiadiazolethiol, there was obtained (E)-4'-[5-fluoro-3-(4-methoxytetrahydropyran-4-yl)phenylthio]acetophenone oxime O-(2-methylthio)ethyl ether in 23% yield as an oil;

NMR Spectrum 1.85–2.0 (m, 4H), 2.19 (s, 2H), 2.25 (s, 3H), 2.84 (t, 2H), 2.98 (s, 3H), 3.74–3.84 (m, 4H), 4.35 (m, 2H), 6.8–7.7 (m, 7H).

EXAMPLE 43

A mixture of 4'-[2-amino-6-(4-methoxytetrahydropyran-4-yl)pyrimidin-4-yloxymethyl]acetophenone (0.358 g), hydroxylamine hydrochloride (0.414 g), sodium acetate (0.492 g), water (2 ml) and 1,4-dioxan (20 ml) was stirred and heated to reflux for 2 hours. The mixture was evaporated and the residue was partitioned between ethyl acetate and water. The organic phase was dried (MgSO$_4$) and evaporated. The residue was recrystallized from methanol. There was thus obtained 4'-[2-amino-6-(4-methoxytetrahydropyran-4-yl)pyrimidin-4-yloxymethyl]acetophenone oxime (0.294 g, 80%), m.p. 172°–175° C.;

NMR Spectrum (CD$_3$SOCD$_3$) 1.6–2.4 (m, 4H), 2.17 (s, 3H), 3.04 (s, 3H), 3.5–3.8 (m, 4H), 5.35 (s, 2H), 6.1 (s, 1H), 6.55 (broad s, 2H), 7.4 (d, 2H), 7.7 (d, 2H).

The 4'-[2-amino-6-(4-methoxytetrahydropyran-4-yl)pyrimidin-4-yloxymethyl]acetophenone used as a starting material was obtained as follows:

Sodium hydride (50%, 0.3 g) was added to a stirred mixture of 4-(2-methyl-1,3-dioxolan-2-yl)benzyl alcohol (1.21 g), 4-(4-bromo-2-methylthiopyrimidin-6-yl)-4-methoxytetrahydropyran (2 g) and DMF (40 ml) which had been cooled to 0° C. The mixture was allowed to warm to ambient temperature and was stirred for 2 hours. The mixture was partitioned between ethyl acetate and water. The organic phase was washed with brine, dried (MgSO$_4$) and evaporated. The residue was purified by column chromatography using a 19:1 mixture of methylene chloride and ethyl acetate as eluent. There was thus obtained 4-methoxy-4-{4-[4-(2-methyl-1,3-dioxolan-2-yl)benzyloxy]-2-methylthiopyrimidin-6-yl}tetrahydropyran (1.7 g, 63%) as an oil.

3-Chloroperoxybenzoic acid (2.7 g) was added portionwise to a stirred mixture of the tetrahydropyran so obtained and methylene chloride (100 ml) which had been cooled to 0° C. The mixture was allowed to warm to ambient temperature and was stirred for 3 hours. The mixture was filtered and the filtrate was purified by column chromatography using a 9:1 mixture of methylene chloride and ethyl acetate as eluent. There was thus obtained 4-methoxy-4-{4-[4-(2-methyl-1,3-dioxolan-2-yl)benzyloxy]-2-methylsulphonylpyrimidin-6-yl}tetrahydropyran (0.96 g, 53%) as an oil.

A mixture of a portion (0.814 g) of the tetrahydropyran so obtained and a saturated solution (60 ml) of ammonia in ethanol was heated to 120° C. in an autoclave for 3 hours. The mixture was evaporated and the residue was purified by column chromatography using a 3:2 mixture of methylene chloride and ethyl acetate as eluent. There was thus obtained 4-{2-amino-4-[4-(2-methyl-1,3-dioxolan-2-yl)benzyloxy]pyrimidin-6-yl}-4-methoxytetrahydropyran (0.291 g, 42%) as an oil.

After repetition of the above-mentioned reactions, a mixture of the tetrahydropyran so obtained (0.55 g), 12N aqueous hydrochloric acid (0.12 ml), water (2 drops), methylene chloride (5 ml) and acetone (10 ml) was stirred at ambient temperature for 20 minutes. The mixture was evaporated and the residue was partitioned between methylene chloride and a saturated aqueous sodium bicarbonate solution. The organic phase was dried (MgSO$_4$) and evaporated. The residue was purified by column chromatography using a 3:2 mixture of methylene chloride and ethyl acetate as eluent. There was thus obtained 4'-[2-amino-6-(4-methoxytetrahydropyran-4-yl)pyrimidin-4-yloxymethyl]acetophenone (0.44 g, 90%) as a solid, m.p. 183°–186° C.;

NMR Spectrum 1.9–2.2 (m, 4H), 2.53 (s, 3H), 3.05 (s, 3H), 3.5–3.7 (m, 4H), 4.8 (m, 2H), 5.33 (s, 2H), 6.22 (s, 1H), 7.35 (d, 2H), 8.85 (d, 2H).

The 4-(2-methyl-1,3-dioxolan-2-yl)benzyl alcohol was obtained as follows:

A mixture of 4'-bromoacetophenone (10 g), ethylene glycol (14 ml), 4-toluenesulphonic acid (20 mg), trimethyl orthoformate (28 ml) and toluene (100 ml) was stirred and heated to 60° C. for 3 hours. The mixture was cooled to ambient temperature and washed with a saturated aqueous sodium bicarbonate solution. The organic solution was evaporated and the residue was distilled. There was thus obtained 4-(2-methyl-1,3-dioxolan-2-yl)bromobenzene (11 g, 91%) as a liquid.

n-Butyl-lithium (1.5M in hexane, 26 ml) was added dropwise to a stirred solution of a portion (7.3 g) of the bromobenzene so obtained in THF (70 ml) which had been cooled to –78° C. The mixture was stirred at –78° C. for 15 minutes. DMF (4.6 ml) was added and the mixture was allowed to warm to ambient temperature. The mixture was poured into a saturated aqueous ammonium chloride solution and extracted with diethyl ether. The organic phase was washed with brine, dried (MgSO$_4$) and evaporated. The residue was purified by column chromatography using methylene chloride as eluent. There was thus obtained 4-(2-methyl-1,3-dioxolan-2-yl)benzaldehyde (3.5 g, 60%) as a liquid.

Sodium borohydride (2 g) was added portionwise to a mixture of the benzaldehyde so obtained, ethanol (10 ml) and 1,4-dioxan (50 ml). The mixture was stirred at ambient temperature for 2 hours. The mixture was evaporated and the residue was partitioned between ethyl acetate and a saturated aqueous ammonium chloride solution. The organic phase was dried (MgSO$_4$) and evaporated. The residue was purified by column chromatography using a 9:1 mixture of methylene chloride and ethyl acetate as eluent. There was thus obtained 4-(2-methyl-1,3-dioxolan-2-yl)benzyl alcohol (2 g, 58%) as an oil.

The 4-(4-bromo-2-methylthiopyrimidin-6-yl)-4-methoxytetrahydropyran was obtained as follows:

4,6-Dihydroxy-2-methylthiopyrimidin (27 g; European Patent Application No. 0343752) was added portionwise to a mixture of phosphoryl bromide (196 g) and acetonitrile (500 ml). The mixture was stirred and heated to reflux for 3 hours. The mixture was evaporated and the residue was poured onto ice and extracted with diethyl ether. The organic phase was dried (MgSO$_4$) and evaporated. The residue was purified by column chromatography using a 97:3 mixture of petroleum ether and ethyl acetate as eluent. There was thus obtained 4,6-dibromo-2-methylthiopyrimidin (35 g, 73%).

n-Butyl-lithium (1.6M in hexane, 41.2 ml) was added dropwise to a stirred solution of a portion (16.8 g) of the pyrimidine so obtained in THF (150 ml) which had been cooled to −110° C. The mixture was stirred at −110° C. for 10 minutes. A solution of tetrahydropyran-4-one (9 g) in THF (30 ml) was added and the mixture was stirred at −110° C. for 30 minutes. The mixture was allowed to warm to ambient temperature, poured into a saturated aqueous ammonium chloride solution and extracted with diethyl ether. The organic phase was washed with brine, dried (MgSO$_4$) and evaporated. The residue was purified by column chromatography using a 4:1 mixture of petroleum ether and ethyl acetate as eluent. There was thus obtained 4-(4-bromo-2-methylthiopyrimidin-6-yl)-4-hydroxytetrahydropyran (11.6 g, 33%) as an oil.

Sodium hydride (50%, 2.7 g) was added portionwise to a stirred solution of the tetrahydropyran so obtained, methyl iodide (9.4 ml) and DMF (70 ml) which had been cooled to 0° C. The mixture was stirred at ambient temperature for 2 hours. The mixture was partitioned between diethyl ether and a saturated aqueous ammonium chloride solution. The organic phase was washed with brine, dried (MgSO$_4$) and evaporated. The residue was purified by column chromatography using a 9:1 mixture of petroleum ether and ethyl acetate as eluent. There was thus obtained 4-(4-bromo-2-methylthiopyrimidin-6-yl)-4-methoxytetrahydropyran (11.2 g, 92%), m.p. 91°–93° C.;

NMR Spectrum 1.5–2.5 (m, 4H), 2.56 (s, 3H), 3.14 (s, 3H), 3.6–4.0 (m, 4H), 7.3 (s, 1H).

EXAMPLE 44

Sodium hydride (50%, 0.048 g) was added to a stirred solution of 4'-[2-amino-6-(4-methoxytetrahydropyran-4-yl)pyrimidin-4-yloxymethyl]acetophenone oxime (0.184 g) in DMF (3 ml). The mixture was stirred for 10 minutes and methyl iodide (0.062 ml) was added. The mixture was stirred at ambient temperature for 1 hour. The mixture was partitioned between ethyl acetate and water. The organic phase was dried (MgSO$_4$) and evaporated. The residue was purified by column chromatography using a 3:2 mixture of methylene chloride and ethyl acetate as eluent. There was thus obtained 4'-[2-amino-6-(4-methoxytetrahydropyran-4-yl)pyrimidin-4-yloxymethyl]acetophenone oxime O-methyl ether (0.05 g, 30%), m.p. 151°–154° C.;

NMR Spectrum 1.6–2.4 (m, 4H), 2.22 (s, 3H), 3.1 (s, 3H), 3.6–3.9 (m, 4H), 3.99 (s, 3H), 4.9 (broad s, 2H), 5.34 (s, 2H), 6.26 (s, 1H), 7.4 (d, 2H), 7.65 (d, 2H).

EXAMPLE 45

Using an analogous procedure to that described in Example 43, 7-[2-amino-6-(4-methoxytetrahydropyran-4-yl)pyrimidin-4-yloxymethyl]chroman-4-one was reacted with hydroxylamine hydrochloride to give 7-[2-amino-6-(4-methoxytetrahydropyran-4-yl)pyrimidin-4-yloxymethyl]chroman-4-one oxime in 79% yield, m.p. 224°–228° C.;

NMR Spectrum (CD$_3$SOCD$_3$) 1.65–1.78 (m, 2H), 1.93–2.06 (m, 2H), 2.82 (t, 2H), 3.0 (s, 3H), 3.52–3.75 (m, 4H), 4.2 (t, 2H), 5.28 (s, 2H), 6.1 (s, 1H), 6.6 (s, 2H), 6.95 (s, 1H), 7.0 (d, 2H), 7.8 (d, 2H).

The 7-[2-amino-6-(4-methoxytetrahydropyran-4-yl)pyrimidin-4-yloxymethyl]chroman-2-one used as a starting material was obtained as follows:

Using analogous procedures to those described in the portion of Example 43 which is concerned with the preparation of starting materials, 7-hydroxymethylchroman-4-one ethylene acetal was reacted with 4-(4-bromo-2-methylthiopyrimidin-6-yl)-4-methoxytetrahydropyran. There were thus obtained in turn:

7-[6-(4-methoxytetrahydropyran-4-yl)-2-methylthiopyrimidin-4-yloxymethyl]chroman-4-one ethylene acetal in 58% yield;

7-[6-(4-methoxytetrahydropyran-4-yl)-2-methylsulphonylpyrimidin-4-yloxymethyl]chroman-4-one ethylene acetal in 60% yield;

7-[2-amino-6-(4-methoxytetrahydropyran-4-yl)pyrimidin-4-yloxymethyl]chroman-4-one ethylene acetal in 45% yield; and 7-[2-amino-6-(4-methoxytetrahydropyran-4-yl)pyrimidin-4-yloxymethyl]chroman-4-one in 91% yield as a solid, m.p. 192°–195° C.;

NMR Spectrum 1.6–1.8 (m, 2H), 1.9–2.1 (m, 2H), 2.7–2.85 (t, 2H), 3.34 (s, 3H), 3.55–3.75 (m, 4H), 4.5–4.6 (t, 2H), 5.53 (s, 2H), 6.12 (s, 1H), 6.63 (s, 2H), 7.07 (s, 1H), 7.10 (d, 1H), 7.75 (d, 1H).

The 7-hydroxymethylchroman-4-one was obtained as follows:

A mixture of 3-bromophenol (8.6 g) and 3-chloropropionyl chloride (4.8 ml) was stirred and heated to 110° C. for 45 minutes. The mixture was cooled to 80° C. and aluminum chloride (20 g) was added portionwise. The mixture was heated to 90° C. for a further 2 hours. The mixture was poured onto a mixture of ice and water and extracted with diethyl ether. The organic phase was washed with brine, dried (MgSO$_4$) and evaporated. The residue was purified by column chromatography using a 4:1 mixture of petroleum ether and methylene chloride as eluent. There was thus obtained 4-bromo-2-hydroxyphenyl 2-chloroethyl ketone (8.2 g, 63%).

A mixture of the product so obtained and 2N aqueous sodium hydroxide (100 ml) was stirred at ambient temperature. The precipitate was isolated and purified by column chromatography using a 4:1 mixture of petroleum ether and methylene chloride as eluent. There was thus obtained 7-bromochroman-4-one in 39% yield, m.p. 95°–97° C.

Using analogous procedures to those described in the portion of Example 43 which is concerned with the preparation of 4-(2-methyl-1,3-dioxolan-2-yl)benzyl alcohol, 7-bromochroman-4-one was converted in turn to:

7-bromochroman-4-one ethylene acetal in 64% yield;

7-formylchroman-4-one ethylene acetal in 75% yield (the n-butyl-lithium and DMF additions were carried out at a reaction temperature of −110° C.); and 7-hydroxymethylchroman-4-one ethylene acetal in 65% yield.

EXAMPLE 46

Sodium hydride (50%, 0.016 g) was added to a stirred solution of 7-[2-amino-6-(4-methoxytetrahydropyran-4-yl)pyrimidin-4-yloxymethyl]chroman-4-one oxime (0.14 g) in DMF (4 ml) which had been cooled to 0° C. The mixture was stirred at 0° C. for 15 minutes. Methyl iodide (0.043 ml) was added and the mixture was stirred at ambient temperature for 1 hour. The mixture was partitioned between ethyl acetate and water. The organic phase was washed with brine, dried (MgSO$_4$) and evaporated. The residue was purified by column chromatography using a 3:2 mixture of methylene chloride and ethyl acetate as eluent. There was thus obtained 7-[2-amino-6-(4 -methoxytetrahydropyran-4-yl)pyrimidin-4-yloxymethyl]chroman-4-one oxime O-methyl ether (0.08 g, 55%), m.p. 178°–180° C.;

NMR Spectrum 1.76 (m, 2H), 2.05 (m, 2H), 2.86 (t, 2H), 3.04 (s, 3H), 3.72 (m, 4H), 3.91 (s, 3H), 4.15 (t, 2H), 4.86 (s, 2H), 5.21 (s, 2H), 6.19 (s, 1H), 6.88 (s, 1H), 6.91 (d, 1H), 7.85 (d, 1H).

EXAMPLE 47

A mixture of 7-[5-fluoro-3-(4-methoxytetrahydropyran-4-yl)phenylthio]chroman-4-one (0.172 g), hydroxylamine hydrochloride (0.04 g) and pyridine (3 ml) was stirred and heated to 80° C. for 2 hours. The mixture was cooled to ambient temperature and partitioned between ethyl acetate and dilute aqueous hydrochloric acid. The organic phase was washed with brine, dried (MgSO$_4$) and evaporated. The product was purified by column chromatography using a 4:1 mixture of petroleum ether and ethyl acetate as eluent. There was thus obtained, as a mixture of (E)- and (Z)-isomers, 7-[5-fluoro-3-(4-methoxytetrahydropyran-4-yl)phenylthio]chroman-4-one oxime (0.112 g, 63%), m.p. 173°–174° C.;

NMR Spectrum 1.85–2.0 (m, 4H), 2.9–3.0 (s & t, 5H), 3.75–3.86 (m, 4H), 4.23 (t, 2H), 6.8–7.02 (m, 4H), 7.21 (s, 1H), 7.62 (broad s's, 1H), 7.77 (d, 1H).

The 7-[5-fluoro-3-(4-methoxytetrahydropyran-4-yl)phenylthio]chroman-4-one used as a starting material was obtained as follows:

A mixture of 7-bromochroman-4-one (0.34 g), 4-(5-fluoro-3-mercaptophenyl)-4-methoxytetrahydropyran (0.252 g), potassium tert-butoxide (0.45 g), tetrakis(triphenylphosphine)palladium(O) (0.092 g) and DMSO (2 ml) was stirred and heated to 110° C. for 1 hour. The mixture was cooled to ambient temperature and partitioned between ethyl acetate and water. The organic phase was washed with brine, dried (MgSO$_4$) and evaporated. The residue was purified by column chromatography using a 4:1 mixture of petroleum ether and ethyl acetate as eluent. There was thus obtained the required starting material (0.172 g, 44%) as a gum.

EXAMPLE 48

Using an analogous procedure to that described in Example 3, except that the reaction mixture was stirred at ambient temperature for 16 hours, 7-[5-fluoro-3-(4-methoxytetrahydropyran-4-yl)phenylthio]chroman-4-one oxime was reacted with methyl iodide to give 7-[5-fluoro-3-(4-methoxytetrahydropyran-4-yl)phenylthio]chroman-4-one oxime O-methyl ether in 72% yield as an oil;

NMR Spectrum 1.82–2.05 (m, 4H), 2.88 (t, 2H), 2.98 (s, 3H), 3.65–3.90 (m, 4H), 3.98 (s, 3H), 4.2 (t, 2H), 6.75–7.6 (m, 5H), 7.88 (m, 1H).

EXAMPLE 49

Using an analogous procedure to that described in Example 3, except that the reaction mixture was stirred at ambient temperature for 7 hours, 7-[5-fluoro-3-(4-methoxytetrahydropyran-4-yl)phenylthio]chroman-4-one oxime was reacted with bromoacetonitrile to give 7-[5-fluoro-3-(4-methoxytetrahydropyran-4-yl)phenylthio]chroman-4-one oxime O-cyanomethyl ether in 86% yield as an oil;

NMR Spectrum 1.8–2.05 (m, 4H), 2.91 (t, 2H), 2.99 (s, 3H), 3.7–3.9 (m, 4H), 4.22 (t, 2H), 4.80 (s, 2H), 6.7–7.3 (m, 5H), 7.83 (m, 1H).

EXAMPLE 50

A mixture of 5-[5-fluoro-3-(4-methoxytetrahydropyran-4-yl)phenylthio]indan-1-one (0.2 g), hydroxylamine hydrochloride (0.056 g) and pyridine (2 ml) was stirred and heated to 60° C. for 2 hours. The mixture was then stirred at ambient temperature for 16 hours. The mixture was partitioned between ethyl acetate and water. The aqueous phase was neutralized by the addition of 6N aqueous hydrochloric acid and extracted with ethyl acetate. The organic solutions were combined, washed with brine, dried (MgSO$_4$) and evaporated.

The residue was purified by column chromatography using increasingly polar mixtures of petroleum ether and ethyl acetate as eluent. There was thus obtained (E)-5-[5-fluoro-3-(4-methoxytetrahydropyran-4-yl)phenylthio] indan-1-one oxime (0.168 g, 81%), m.p. 163°–164° C. (recrystallized from ethyl acetate);

NMR Spectrum (CD$_3$SOCD$_3$) 1.8–2.0 (m, 4H), 2.81 (m, 2H), 2.90 (s, 3H), 3.0 (m, 2H), 3.6–3.71 (m, 4H), 7.0–7.5 (m, 5H), 7.59 (m, 1H).

The 5-[5-fluoro-3-(4-methoxytetrahydropyran-4-yl)phenylthio]indan-1-one used as a starting material was obtained as follows:

A solution of 3-chloropropionyl chloride (15 ml) in methylene chloride (10 ml) was added to a stirred suspension of aluminum chloride (20.1 g) in methylene chloride (35 ml) and the mixture was stirred at ambient temperature for 15 minutes. A mixture of bromobenzene (15 ml) in methylene chloride (10 ml) was added portionwise during a period of 1 hour. The mixture was stirred at ambient temperature for 16 hours. The mixture was poured onto a mixture of ice and 1N aqueous hydrochloric acid. The organic phase was washed with water and with a saturated aqueous sodium bicarbonate solution, dried (MgSO$_4$) and evaporated. The residue was purified by column chromatography using a 15:1 mixture of petroleum ether and ethyl acetate as eluent.

There was thus obtained 4-bromophenyl 2-chloroethyl ketone (27.9 g, 85%).

A mixture of aluminum chloride (54 g) and sodium chloride (11.8 g) was stirred and heated to 200° C. 4-Bromophenyl 2-chloroethyl ketone (10 g) and added portionwise and the mixture was maintained at 200° C. for 2 hours. The mixture was poured onto a mixture of ice and 1N aqueous hydrochloric acid. The resultant mixture was extracted with ethyl acetate. The organic solution was washed with a saturated aqueous sodium bicarbonate solution and with water, dried ($MgSO_4$) and evaporated. The residue was purified by column chromatography using increasingly polar mixtures of petroleum ether and ethyl acetate as eluent. There was thus obtained 5-bromoindan-1-one (5.7 g, 67%).

Potassium tert-butoxide (0.093 g) was added to a solution of 4-(5-fluoro-3-mercaptophenyl)-4-methoxytetrahydropyran (0.2 g) in DMSO (2 ml) and the mixture was stirred at ambient temperature for 10 minutes. 5-Bromoindan-1-one (0.261 g) and tetrakis(triphenylphosphine)palladium(O) (0.076 g) were added in turn and the mixture was stirred and heated to 120° C. for 15 minutes. The mixture was cooled to ambient temperature and partitioned between ethyl acetate and water. The organic phase was washed with water, dried ($MgSO_4$) and evaporated. The residue was purified by column chromatography using a 5:1 mixture of petroleum ether and ethyl acetate as eluent. There was thus obtained 5-[5-fluoro-3-(4-methoxytetrahydropyran-4-yl)phenylthio]indan-1-one (0.29 g, 94%), m.p. 120°–121° C.;

NMR Spectrum 1.7–2.0 (m, 4H), 2.45–2.7 (m, 2H), 2.94 (s, 3H), 2.9–3.1 (m, 2H), 3.6–3.9 (m, 4H), 6.9–7.3 (m, 5H), 7.6 (d, 1H).

EXAMPLE 51

Using an analogous procedure to that described in Example 3, except that the reaction mixture was stirred at ambient temperature for 16 hours, (E)-5-[5-fluoro-3-(4-methoxytetrahydropyran-4-yl)phenylthio]indan-1-one oxime was reacted with methyl iodide to give (E)-5-[5-fluoro-3-(4-methoxytetrahydropyran-4-yl)phenylthio]indan-1-o oxime O-methyl ether in 51% yield, m.p. 92°–94° C.;

NMR Spectrum 1.8–2.0 (m, 4H), 2.88 (m, 2H), 2.96 (s, 3H), 3.0 (m, 2H), 3.75–3.87 (m, 4H), 3.99 (s, 3H), 6.8–7.3 (m, 5H), 7.63 (d, 1H).

EXAMPLE 52

Using an analogous procedure to that described in Example 3, except that the reaction mixture was stirred at ambient temperature for 16 hours, (E)-5-[5-fluoro-3-(4-methoxytetrahydropyran-4-yl)phenylthio]indan-1-one oxime was reacted with bromoacetonitrile to give (E)-5-[5-fluoro-3-(4-methoxytetrahydropyran-4-yl)phenylthio]indan-1-one oxime O-cyanomethyl ether in 66% yield, m.p. 91°–93° C.;

NMR Spectrum 1.8–2.0 (m, 4H), 2.90 (m, 2H), 2.99 (s, 3H), 3.02 (m, 2H), 3.78–3.85 (m, 4H), 4.80 (s, 2H), 6.88–7.02 (m, 2H), 7.15–7.35 (m, 3H), 7.65 (d, 1H).

EXAMPLE 53

Sodium hydride (50%, 0.248 g) was added to a stirred solution of (E)-5-[5-fluoro-3-(4-methoxytetrahydropyran-4-yl)phenylthio]indan-1-one oxime (0.4 g) in THF (20 ml) and the mixture was stirred at ambient temperature for 10 minutes. 4-Chloromethylpyridine hydrochloride (0.22 g), 15-crown-5 (2 drops) and sodium iodide (0.309 g) were added in turn. The mixture was stirred and heated to 60° C. for 16 hours. The mixture was cooled to ambient temperature and partitioned between ethyl acetate and water. The organic phase was washed with brine, dried ($MgSO_4$) and evaporated. The residue was purified by column chromatography using increasingly polar mixtures of petroleum ether and ethyl acetate as eluent. There was thus obtained (E)-5-[5-fluoro-3-(4-methoxytetrahydropyran-4-yl)phenylthio]indan-1-one oxime O-(4-pyridyl)methyl ether (0.3 g, 61%) as a gum;

NMR Spectrum 1.75–1.90 (m, 4H), 2.91 (s, 3H), 2.86–3.0 (m, 4H), 3.68–3.80 (m, 4H), 5.15 (s, 2H), 6.85 (m, 2H), 7.1 (s, 1H), 7.12–7.3 (m, 4H), 7.55 (d, 1H), 8.6 (broad s, 2H).

EXAMPLE 54

Using an analogous procedure to that described in Example 50, 5-[5-fluoro-3-(4-methoxytetrahydropyran-4-yl)phenylthio]inden-1-one was reacted with hydroxylamine hydrochloride to give 5-[5-fluoro-3-(4-methoxytetrahydropyran-4-yl)phenylthio]inden-1-one oxime in 43% yield, m.p.124°–136° C., as a 11:9 mixture of the (E)- and (Z)-isomers;

NMR Spectrum ($CD_3SOCD_3$) 1.7–2.0 (m, 4H), 2.87 (s, 3H), 3.5–3.8 (m, 4H), 6.59 (d, 0.5H), 6.82 (d, 0.5H), 6.9–7.5 (m, 6H), 7.62 (d, 0.5H), 8.1 (d, 0.5H).

The 5-[5-fluoro-3-(4-methoxytetrahydropyran-4-yl)phenylthio]inden-1-one used as a starting material was obtained as follows:

Ethylene glycol (5 ml) and bromine (0.218 ml) were added in turn to a stirred solution of 5-[5-fluoro-3-(4-methoxytetrahydropyran-4-yl)phenylthio]indan-1-one (1.5 g) in THF (10 ml). The mixture was stirred at ambient temperature for 1 hour. A further portion of bromine (0.15 ml) was added and the mixture was stirred at ambient temperature for 1 hour. The mixture was partitioned between ethyl acetate and a saturated aqueous sodium metabisulphite solution. The organic phase was washed with water and with brine, dried ($MgSO_4$) and evaporated.

A mixture of the product so obtained, ethylene glycol (2.7 ml), triethyl orthoformate (2.7 ml), 4-toluenesulphonic acid (0.01 g) and toluene (5 ml) was stirred and heated to 45° C. for 16 hours. The mixture was cooled to ambient temperature and partitioned between ethyl acetate and water. The organic phase was washed with water, dried ($MgSO_4$) and evaporated. There was thus obtained 2-bromo-5-[5-fluoro-3-(4-methoxytetrahydropyran-4-yl)phenylthio]indan-1-one ethylene acetal (2 g) which was used without further purification.

Sodium methoxide (0.65 g) was added portionwise to a stirred solution of the acetal so obtained in DMSO (15 ml) which had been cooled to 10° C. The mixture was stirred at 10° C. for 1 hour. A further portion (0.3 g) of sodium methoxide was added and the mixture was heated to 40° C. for 2 hours. The mixture was partitioned between ethyl acetate and a saturated aqueous ammonium chloride solution. The organic phase was washed with water and with brine, dried ($MgSO_4$) and evaporated. The residue was purified by column chromatography using a 5:1 mixture of petroleum ether and ethyl acetate as eluent. There was thus obtained 5-[5-fluoro-3-(4-methoxytetrahydropyran-4-yl)phenylthio]inden-1-one ethylene acetal (1.4 g, 84%), m.p. 126°–127° C.

A mixture of a portion (0.8 g) of the product so obtained, 0.5N aqueous hydrochloric acid (4 m) and THF (10 ml) was stirred at ambient temperature for 16 hours. The mixture was partitioned between ethyl acetate and water. The organic phase was dried (MgSO$_4$) and evaporated. There was thus obtained 5-[5-fluoro-3-(4-methoxytetrahydropyran-4-yl)phenylthio] inden-1-one (0.705 g, 98%) which was used without further purification.

EXAMPLE 55

A mixture of 4'-[5-fluoro-3-(4-methoxytetrahydropyran-4-yl)phenylthio]propiophenone (0.88 g), hydroxylamine hydrochloride (0.212 g) and pyridine (4 ml) was stirred and heated to 70° C. for 8 hours. The mixture was cooled to ambient temperature and partitioned between ethyl acetate and 1N aqueous hydrochloric acid. The organic phase was washed with brine, dried (MgSO$_4$) and evaporated. The residue was purified by column chromatography using a 4:1 mixture of petroleum ether and ethyl acetate as eluent. There was thus obtained 4'-[5-fluoro-3-(4-methoxytetrahydropyran-4-yl)phenylthio]propiophenone (0.71 g, 78%), m.p. 125°–127° C.;

NMR Spectrum 1.17 (t, 3H), 1.83–2.0 (m, 4H), 2.80 (q, 2H), 2.97 (s, 3H), 3.84–3.92 (m, 4H), 6.85–7.0 (m, 2H), 7.16 (s, 1H), 7.36 (d, 2H), 7.60 (d, 2H).

The 4'-[5-fluoro-3-(4-methoxytetrahydropyran-4-yl)phenylthio]propiophenone used as a starting material was obtained as follows:

Using an analogous procedure to that described in the portion of Example 25 which is concerned with the preparation of starting materials, 4'-bromopropiophenone was reacted with 4-(5-fluoro-3-mercaptophenyl)-4-methoxytetrahydropyran to give the required starting material in 68% yield, m.p. 89°–90° C.;

NMR Spectrum 1.19 (t, 3H), 1.8–2.0 (m, 4H), 2.92–3.0 (m, 5H), 3.75–3.85 (m, 4H), 7.03 (m, 2H), 7.24 (m, 1H), 7.30 (d, 2H), 7.86 (d, 2H).

EXAMPLE 56

Using an analogous procedure to that described in Example 3, 4'-[5-fluoro-3-(4-methoxytetrahydropyran-4-yl)phenylthio]propiophenone oxime was reacted with methyl iodide to give 4'-[5-fluoro-3-(4-methoxytetrahydropyran-4-yl)phenylthio]propiophenone oxime O-methyl ether in 87% yield as an oil;

NMR Spectrum 1.13 (t, 3H), 1.8–2.0 (m, 4H), 2.73 (q, 2H), 2.98 (s, 3H), 3.8–3.84 (m, 4H), 3.98 (s, 3H), 6.8–6.98 (m, 2H), 7.15 (s, 1H), 7.37 (d, 2H), 7.61 (d, 2H).

EXAMPLE 57

Using an analogous procedure to that described in Example 3, 4'-[5-fluoro-3-(4-methoxytetrahydropyran-4-yl)phenylthio]propiophenone oxime was reacted with allyl bromide to give 4'-[5-fluoro-3-(4-methoxytetrahydropyran-4-yl)phenylthio]propiophenone oxime O-allyl ether in 91% yield as an oil;

NMR Spectrum 1.15 (t, 3H), 1.8–2.0 (m, 4H), 2.78 (q, 2H), 3.0 (s, 3H), 3.78–3.85 (m, 4H), 4.68 (m, 2H), 5.21 (d, 1H), 5.31 (d, 1H), 5.9–6.1 (m, 1H), 6.8–6.98 (m, 2H), 7.15 (s, 1H), 7.35 (d, 2H), 7.61 (d, 2H).

EXAMPLE 58

Using an analogous procedure to that described in Example 55, 4'-[5-fluoro-3-(4-methoxytetrahydropyran-4-yl)phenylthio]isobutyrophenone was reacted with hydroxylamine hydrochloride to give a 1:1 mixture (E)- and (Z)-4'-[5-fluoro-3-(4-methoxytetrahydropyran-4-yl)phenylthio] isobutyrophenone oxime in 83% yield, m.p. 107°–108° C.;

NMR Spectrum 1.14 (d, 3H), 1.22 (d, 3H), 1.83–2.0 (m, 4H), 2.82 and 3.58 (2 m's, 1H), 2.99 (s, 3H), 3.77–3.86 (m, 4H), 6.84–7.0 (m, 2H), 7.15–7.40 (m, 5H), 7.78 and 8.04 (2 broad s's, 1H).

The 4'-[5-fluoro-3-(4-methoxytetrahydropyran-4-yl)phenylthio]isobutyrophenone used as a starting material was obtained as follows:

Isopropylmagnesium bromide (2M in diethyl ether, 0.815 ml) was added dropwise to a stirred solution of 4-[5-fluoro-3-(4-methoxytetrahydropyran-4-yl)phenylthio]benzaldehyde (0.47 g) in THF (5 ml). The mixture was stirred at ambient temperature for 3 hours. The mixture was partitioned between diethyl ether and dilute aqueous hydrochloric acid. The organic phase was washed with brine, dried (MgSO$_4$) and evaporated. The residue was purified by column chromatography using a 5:1 mixture of petroleum ether and ethyl acetate as eluent. There was thus obtained 4-[5-fluoro-3-(4-methoxytetrahydropyran-4-yl)phenylthio]-α-isopropylbenzyl alcohol (0.18 g, 34%) as an oil.

Pyridinium chlorochromate (0.16 g) was added to a solution of the product so obtained in methylene chloride (5 ml). The mixture was stirred at ambient temperature for 4 hours. The mixture was partitioned between methylene chloride and water. The organic phase was washed with brine, dried (MgSO$_4$) and evaporated. The residue was purified by column chromatography using a 5:1 mixture of petroleum ether and ethyl acetate as eluent. Ther was thus obtained 4'-[5 -fluoro-3-(4-methoxytetrahydropyran-4-yl)phenylthio]isobutyrophenone (0.14 g, 78%) as an oil.

EXAMPLE 59

A solution of 4-[5-fluoro-3-(4-methoxytetrahydropyran-4-yl)phenylthio]benzyl methyl ketone (0.25 g) in ethanol (1 ml) was added to a stirred sodium ethoxide solution [prepared by the addition of sodium (0.02 g) to ethanol (1 ml)]. The mixture was stirred at ambient temperature for 5 minutes. Isopentylnitrite (0.09 ml) was added dropwise. The mixture was stirred at ambient temperature for 2 hours and then heated to 60° C. for 2 hours. The mixture was partitioned between ethyl acetate and dilute aqueous hydrochloric acid. The organic phase was washed with brine, dried (MgSO$_4$) and evaporated. The residue was purified by column chromatography using increasingly polar mixture of petroleum ether and ethyl acetate as eluent. There was thus obtained acetyl 4-[5-fluoro-3-(4-methoxytetrahydropyran-4-yl)phenylthio]phenyl ketone oxime (0.14 g), 44%), m.p. 151°–152° C.;

NMR Spectrum 1.85–2.0 (m, 4H), 2.52 (s, 3H), 2.99 (s, 3H), 3.76–3.86 (m, 4H), 6.92–7.04 (m, 2H), 7.16–7.40 (m, 5H), 8.23 (s, 1H).

The 4-[5-fluoro-3-(4-methoxytetrahydropyran-4-yl)phenylthio]benzyl methyl ketone used as starting material was obtained as follows:

n-Butylamine (1 ml) was added to a mixture of 4-Bromobenzaldehyde (18.5 g), nitroethane (8.25 g) and ethanol (40 ml). The mixture was stirred and heated to reflux for 24 hours. The mixture was cooled to ambient temperature and partitioned between diethyl ether and water. The organic phase was washed with brine, dried (MgSO$_4$) and evaporated. The residue was purified by column chromatography using a 20:1 mixture of petroleum ether and diethyl ether as eluent to give a solid (5.6 g, 23%). A mixture of the solid so obtained, iron (11 g), ferric chloride (0.13 g) and water (20 ml) was stirred and heated to reflux for 2.5 hours. Concentrated hydrochloric acid (10 ml) was added and the mixture was heated to reflux for 1 hour. The mixture was cooled to ambient temperature and partitioned between ethyl acetate and water. The organic phase was washed with brine, dried ($MgSO_4$) and evaporated. The residue was purified by column chromatography using increasingly polar mixtures of petroleum ether and ethyl acetate as eluent. There was thus obtained 4-bromobenzyl methyl ketone (2.6 g, 52%) as an oil.

Using an analogous procedure to that described in the portion of Example 25 which is concerned with the preparation of starting materials, 4-bromobenzyl methyl ketone was reacted with 4-(5-fluoro-3-mercaptophenyl)-4-methoxytetrahydropyran to give the required starting material in 64% yield as an oil.

EXAMPLE 60

A solution of 4'-[5-fluoro-3-(4-methoxytetrahydropyran-4-yl)phenylthio]phenylacetonitrile (0.384 g) in ethanol (1 ml) was added to a stirred sodium ethoxide solution [prepared by the addition of sodium (0.032 g) to ethanol (1.5 ml)]. The mixture was stirred at ambient temperature for 5 minutes. Isopentylnitrite (0.145 ml) was added dropwise and the mixture was stirred at ambient temperature for 15 minutes. The mixture was partitioned between ethyl acetate and dilute aqueous hydrochloric acid. The organic phase was washed with brine, dried ($MgSO_4$) and evaporated. The residue was purified by column chromatography using a 10:3 mixture of petroleum ether and ethyl acetate as eluent. There was thus obtained, as a mixture of (E)- and (Z)-isomers, 4'-[5-fluoro-3-(4-methoxytetrahydropyran-4-yl)phenylthio]benzoyl cyanide oxime (0.075 g, 18%), m.p. 197°–198° C.;

NMR Spectrum 1.85–2.0 (m, 4H), 3.0 (s, 3H), 3.78–3.86 (m, 4H), 6.92–7.10 (m, 2H), 7.2–7.37 (m, 3H), 7.72 (d, 2H), 7.96 & 9.2 (2 m's, 1H).

The 4'-[5-fluoro-3-(4-methoxytetrahydropyran-4-yl)phenylthio]phenylacetonitrile used as a starting material was obtained as follows:

Using an analogous procedure to that described in the portion of Example 25 which is concerned with the preparation of starting materials, 4'-bromophenylacetonitrile was reacted with 4-(5-fluoro-3-mercaptophenyl)-4-methoxytetrahydropyran to give the required starting material in 95% yield as an oil.

EXAMPLE 61

Pyridine (0.02 ml) was added to a stirred mixture of 4-[5-fluoro-3-(4-methoxytetrahydropyran-4-yl)phenylthio] benzaldehyde oxime (0.36 g), N-chlorosuccinimide (0.135 g) and chloroform (2 ml). The mixture was heated to 60° C. for 45 minutes. The mixture was cooled to ambient temperature. Trimethylamine (0.15 ml) and a solution of dimethylamine (2 equivalents) in methylene chloride (1 ml) were added in turn. The mixture was stirred at ambient temperature for 3 hours. The mixture was partitioned between ethyl acetate and dilute aqueous hydrochloric acid. The organic phase was washed with brine, dried ($MgSO_4$) and evaporated. The residue was purified by column chromatography using a 2:1 mixture of petroleum ether and ethyl acetate as eluent. There was thus obtained N,N-dimethyl-4-[5-fluoro-3-(4-methoxytetrahydropyran-4-yl)phenylthio] benzamide oxime (0.55 g, 12%), m.p. 106°–107° C.;

NMR Spectrum 1.83–2.0 (m, 4H), 2.68 (s, 6H), 2.98 (s, 3H), 3.75–3.84 (m, 4H), 6.52 (broad s, 1H), 6.9–7.0 (m, 2H), 7.16 (s, 1H), 7.3–7.4 (m, 4H).

EXAMPLE 62

Using an analogous procedure to that described in Example 12, 4-[5-fluoro-3-(4-methoxytetrahydropyran-4-yl)phenylthio]phenyl 2-thiazolyl ketone was reacted with hydroxylamine hydrochloride to give in turn the geometric isomers of 4-[5-fluoro-3-(4-methoxytetrahydropyran-4-yl)phenylthio]phenyl 2-thiazolyl ketone oxime:

Isomer A in 40% yield, m.p. 153°–154° C.,

NMR Spectrum ($CD_3SOCD_3$) 1.8–2.0 (m, 4H), 2.91 (s, 3H), 3.6–3.8 (m, 4H), 7.0–7.3 (m, 3H), 7.46 (d, 2H), 7.72 (d, 2H), 8.06 (s, 2H); and Isomer B in 26% yield, m.p. 164°–165° C., NMR Spectrum ($CD_3SOCD_3$) 1.8–2.0 (m, 4H), 2.90 (s, 3H), 3.6–3.8 (m, 4H), 7.1–7.3 (m, 3H), 7.46 (d, 2H), 7.54 (d, 2H), 7.7–7.9 (m, 2H).

The 4-[5-fluoro-3-(4-methoxytetrahydropyran-4-yl)phenylthio]phenyl 2-thiazolyl ketone used as a starting material was obtained as follows:

n-Butyl-lithium (1.6M in hexane, 3.7 ml) was added dropwise to a stirred solution of thiazole (0.41 ml) in THF (5 ml) which had been cooled to −70° C. The mixture was stirred at −70° C. for 1 hour. A solution of 4-[5-fluoro-3-(4-methoxytetrahydropyran-4-yl)phenylthio]benzaldehyde (1.7 g) in THF (10 ml) was added. The mixture was stirred at −50° C. for 1 hour and at ambient temperature for 2 hours. The mixture was partitioned between ethyl acetate and water. The organic phase was washed with brine, dried ($MgSO_4$) and evaporated. The residue was purified by column chromatography using a 3:2 mixture of petroleum ether and ethyl acetate as eluent. There was thus obtained 4-[5-fluoro-3-(4-methoxytetrahydropyran-4-yl)phenylthio]-α-(2-thiazolyl)benzyl alcohol (1.36 g, 65%) as an oil.

A mixture of a portion (0.85 g) of the product so obtained, pyridinium chlorochromate (0.68 g) and methylene chloride (10 ml) was stirred at ambient temperature for 2 hours. The mixture was partitioned between diethyl ether and 1N aqueous sodium hydroxide solution. The organic phase was washed with 1N aqueous hydrochloric acid solution and with water, dried ($MgSO_4$) and evaporated. The residue was purified by column chromatography using a 7:3 mixture of petroleum ether and ethyl acetate as eluent. There was thus obtained the required starting material (0.634 g, 75%) as an oil.

EXAMPLE 63

A mixture of 6-[5-fluoro-3-(4-methoxytetrahydropyran-4-yl)phenylthio]pyrid-3-yl methyl ketone (0.2 g), hydroxylamine hydrochloride (0.058 g) and pyridine (2 ml) was stirred and heated to 100° C. for 2 hours. The mixture was cooled to ambient temperature and partitioned between ethyl acetate and water. The organic phase was washed with brine, dried ($MgSO_4$) and evaporated. The residue was purified by column chromatography using a 5:1 mixture of petroleum ether and ethyl acetate as eluent. There was thus obtained 6-[5-fluoro-3-(4-methoxytetrahydropyran-4-yl)phenylthio] pyrid-3-yl methyl ketone oxime (0.19 g, 90t), m.p. 121°–123° C.;

NMR Spectrum 1.86–2.06 (m, 4H), 2.26 (s, 3H), 3.01 (s, 3H), 3.75–3.90 (m, 4H), 6.96–7.4 (m, 4H), 7.78 (m, 1H), 8.07 (s, 1H), 8.68 (m, 1H).

The 6-[5-fluoro-3-(4-methoxytetrahydropyran-4-yl)phenylthio] pyrid-3-yl methyl ketone used as a starting material was obtained as follows:

A mixture of 4-(5-fluoro-3-mercaptophenyl)-4-methoxytetrahydropyran (2.42 g), potassium hydroxide (0.56 g) and DMF (5 ml) was stirred and heated to 140° C. until all of the base had reacted. Cuprous oxide (0.7 g) and 2,5-dibromopyridine (2.84 g) were added and the mixture was heated to 140° C. for 1 hour. The mixture was cooled to ambient temperature and partitioned between ethyl acetate and water. The organic phase was washed with brine, dried (MgSO$_4$) and evaporated. The residue was purified by column chromatography using a 5:1 mixture of petroleum ether and ethyl acetate as eluent. There was thus obtained 5-bromo-2-[5-fluoro-3-(4-methoxytetrahydropyran-4-yl)phenylthio)pyridine (2.32 g, 58%), m.p. 77°–78° C.

n-Butyl-lithium (1.6M in hexane, 3.45 ml) was added dropwise to a solution of the pyridine so obtained (2 g) in THF (20 ml) which had been cooled to −100° C. The mixture was stirred at −100° C. Acetaldehyde (0.33 g) was added and the mixture was stirred and allowed to warm over 2 hours to ambient temperature. The mixture was partitioned between ethyl acetate and water. The organic phase was washed with brine, dried (MgSO$_4$) and evaporated. The residue was purified by column chromatography using increasingly polar mixtures of petroleum ether and ethyl acetate as eluent. There was thus obtained 2-[5-fluoro-3-(4-methoxytetrahydropyran-4-yl)phenylthio]-5-(1-hydroxyethyl)pyridine (1.54 g, 86%) as an oil A mixture of the material so obtained, pyridinium chlorochromate (1.35 g) and methylene chloride (30 ml) was stirred at ambient temperature for 2.5 hours. The mixture was washed with water and with brine, dried (MgSO$_4$) and evaporated. The residue was triturated under a mixture of pentane and diethyl ether to give 6-[5-fluoro-3-(4-methoxytetrahydropyran-4-yl)phenylthio]pyrid-3-yl methyl ketone (1.15 g, 77%), m.p. 73°–74° C.;

NMR Spectrum 1.8–2.05 (m, 4H), 2.57 (s, 3H), 3.05 (s, 3H), 3.7–4.0 (m, 4H), 7.0–7.5 (m, 4H), 8.0–8.15 (m, 1H), 8.95 (m, 1H).

EXAMPLE 64

Using an analogous procedure to that described in Example 3, except that the reaction mixture was stirred at ambient temperature for 16 hours, 6-[5-fluoro-3-(4-methoxytetrahydropyran-4-yl)phenylthio]pyrid-3-yl methyl ketone oxime was reacted with methyl iodide to give 6-[5-fluoro-3-(4-methoxytetrahydropyran-4-yl)phenylthio]pyrid-3 -yl methyl ketone oxime O-methyl ether in 61% yield as an oil;

NMR Spectrum 1.8–21. (m, 4H), 2.19 (s, 3H), 3.01 (s, 3H), 3.6–3.9 (m, 4H), 3.99 (s, 3H), 6.9–7.4 (m, 4H), 7.7–7.9 (m, 1H), 8.65 (m, 1H).

EXAMPLE 65

Using an analogous procedure to that described in Example 3, except that the reaction mixture was stirred at ambient temperature for 5 hours, 6-[5-fluoro-3-(4-methoxytetrahydropyran-4-yl)phenylthio] pyrid-3-yl methyl ketone oxime was reacted with bromoacetonitrile to give 6-[5-fluoro-3-(4-methoxytetrahydropyran-4-yl)phenylthio]pyrid-3-yl methyl ketone oxime O-cyanomethyl ether in 70% yield, m.p. 128°–130° C.;

NMR Spectrum 1.75–2.0 (m, 4H), 2.18 (s, 3H), 2.96 (s, 3H), 3.6–3.9 (m, 4H), 4.75 (s, 2H), 6.8–7.4 (m, 4H), 7.65–7.85 (m, 1H), 8.60 (d, 1H).

EXAMPLE 66

A mixture of 4'-{5-fluoro-3-[(2RS,3SR)-3-methoxy-2-methyltetrahydrofuran-3-yl] phenylthio}acetophenone (3.6 g), hydroxylamine hydrochloride (0.765 g), pyridine (6.5 ml) and ethanol (30 ml) was stirred and heated to reflux for 3 hours. The mixture was cooled to ambient temperature and partitioned between methylene chloride and water. The organic phase was washed with 1N aqueous hydrochloric acid and with brine, dried (MgSO$_4$) and evaporated. The residue was purified by column chromatography using a 20:1 mixture of methylene chloride and methanol as eluent. There was thus obtained (E)-4'-{5 -fluoro-3-[(2RS,3SR)-3-methoxy-2-methyltetrahydrofuran-3-yl] phenylthio}acetophenone oxime (2.4 g, 64%), m.p. 105°–106° C.

The 4'-{5-fluoro-3-[(2RS,3SR)-3-methoxy-2-methyltetrahydrofuran-3-yl]phenylthio}acetophenone used as a starting material was obtained as follows:

A solution of 2-methyltetrahydrofuran-3-one (18.4 g) in THF (30 ml) was added to a THF solution of 3,5-difluorophenylmagnesium bromide [prepared by the addition of magnesium (4.8 g) to a mixture of 3,5-difluorobromobenzene (31 g), 1,2-dibromoethane (0.3 g) and THF (60 ml)]. The mixture was stirred at ambient temperature for 3 hours. The mixture was partitioned between ethyl acetate and a saturated aqueous ammonium chloride solution. The organic phase was washed with water and with brine, dried (MgSO$_4$) and evaporated. The residue was purified by column chromatography using increasingly polar mixtures of hexane and ethyl acetate as eluent. There was thus obtained (2RS,3SR)-3-(3,5-difluorophenyl)-3-hydroxy-2-methyltetrahydrofuran (16.3 g, 38%), m.p. 89°–90° C.

A solution of the product so obtained in DMF (30 ml) was added to a stirred suspension of sodium hydride (50%, 4.8 g) in DMF (25 ml) which had been cooled to 0° C. The mixture was stirred at ambient temperature for 1 hour. The mixture was recooled to 0° C. and methyl iodide (14.2 g) was added. The mixture was stirred at ambient temperature for 4 hours. The mixture was partitioned between diethyl ether and water. The organic phase was washed with water and with brine, dried (MgSO$_4$) and evaporated. The residue was purified by column chromatography using a 10:3 mixture of hexane and ethyl acetate as eluent. There was thus obtained (2RS,3SR)-3-(3,5-difluorophenyl)-3-methoxy-2-methyltetrahydrofuran (12.51 g, 74%) as a liquid;

NMR Spectrum (CD$_3$SOCD$_3$) 1.05 (d, 3H), 2.5 (m, 2H), 3.15 (s, 3H), 3.62 (q, 1H), 3.9 (m, 2H), 7.05–7.25 (m, 3H).

Sodium methanethiolate (3.84 g) was added to a stirred solution of the product so obtained in DMA (30 ml). The mixture was heated to 60° C. for 3 hours. The mixture was partitioned between ethyl acetate and water. The organic phase was washed with water and with brine, dried (MgSO$_4$) and evaporated. The residue was purified by column chromatography using a 10:3 mixture of hexane and ethyl acetate as eluent. There was thus obtained (2RS,3SR)-3-(5-fluoro-3 -methylthiophenyl)-3-methoxy-2-methyltetrahydrofuran (12.6 g, 90%) as a liquid;

NMR Spectrum (CD$_3$SOCD$_3$) 1.0 (d, 3H), 2.5 (m, 2H), 3.1 (s, 3H), 3.6 (q, 1H), 3.9 (m, 2H), 6.9–7.1 (m, 3H).

3-Chloroperoxybenzoic acid (12.6 g) was added portionwise to a stirred solution of the product so obtained in methylene chloride (25 ml) which had been cooled to 0° C. The mixture was stirred at ambient temperature for 30 minutes. The mixture was recooled to 0° C. and calcium hydroxide (13.4 g) was added. The mixture was stirred at ambient temperature for 10 minutes. The mixture was filtered and the filtrate was dried (MgSO₄) and evaporated. The residue was cooled to 0° C. and stirred. Trifluoroacetic anhydride (85 ml) was added portionwise. The mixture was stirred at ambient temperature for 30 minutes. The mixture was evaporated. A 1:1 mixture of triethylamine and methanol (total volume 80 ml) was added and the residue was partitioned between diethyl ether and 2N aqueous sodium hydroxide solution. The aqueous layer was acidified by the addition of concentrated hydrochloric acid. The acid solution was extracted with diethyl ether. The organic phase was washed with water and with brine, dried (MgSO₄) and evaporated. There was thus obtained (2RS,3SR)-3-(5-fluoro-3-mercaptophenyl)-3-methoxy-2-methyltetrahydrofuran (4.4 g, 37%), m.p. 78°–80° C.

A mixture of a portion (3.71 g) of the product so obtained, 4'-fluoroacetophenone (2.12 g), potassium carbonate (4.64 g) and DMF (20 ml) was stirred and heated to 140° C. for 2 hours. The mixture was cooled to ambient temperature and partitioned between ethyl acetate and water. The organic phase was washed with water and with brine, dried (MgSO₄) and evaporated. The residue was purified by column chromatography using a 3:1 mixture of hexane and ethyl acetate as eluent. There was thus obtained 4'-{5-fluoro-3-[(2RS, 3SR)-3-methoxy-2-methyltetrahydrofuran-3-yl]phenylthio}acetophenone (4.29 g, 78%) an oil;

NMR Spectrum (CD₃SOCD₃) 1.0 (d, 3H), 2.45 (m, 2H), 2.55 (s, 3H), 3.1 (s, 3H), 3.65 (q, 1H), 3.9 (m, 2H), 7.2–8.0 (m, 7H).

EXAMPLE 67

A mixture of (E)-4'-[4-(1,2-dihydroxyprop-2-yl)thien-2-ylthio]acetophenone oxime (0.21 g), acetone dimethyl acetal (0.5 ml), 4-toluenesulphonic acid (0.02 g) and acetone (5 ml) was stirred and heated to reflux for 1 hour. The mixture was cooled to ambient temperature and neutralized by the addition of dilute aqueous potassium carbonate solution. The mixture was evaporated and the residue was partitioned between ethyl acetate and water. The organic phase was washed with water and with brine, dried (MgSO₄)and evaporated. The residue was purified by column chromatography using increasingly polar mixtures of hexane and ethyl acetate as eluent. There was thus obtained (E)-4'-[4-(2,2,4-trimethyl-1,3-dioxolan-4-yl)thien-2-ylthio] acetophenone oxime (0.65 g, 28%) as a gum, NMR Spectrum 1.4 (s, 3H), 1.5 (s, 3H), 1.6 (s, 3H), 2.2 (s, 3H), 4.0–4.1 (q, 2H), 7.2 (d, 2H), 7.25 (d, 1H), 7.35 (d, 1H), 7.5 (d, 2H), 7.8 (broad s, 1H).

The (E)-4'-[4-(1,2-dihydroxyprop-2-yl)thien-2-ylthio]acetophenone oxime used as a starting material was obtained as follows:

n-Butyl-lithium (1.6M in hexane, 4.23 ml) was added dropwise to a stirred solution of 2,4-dibromothiophene (1.74 g) in diethyl ether (60 ml) which had been cooled to –70° C. The mixture was stirred at –70° C. for 30 minutes. A solution of di-[4-(2-methyl-1,3-dioxolan-2-yl)phenyl]disulphide (2.29 g) in THF (25 ml) was added. The mixture was stirred at –70° C. for 30 minutes and then allowed to warm to ambient temperature. The mixture was poured into a saturated aqueous ammonium chloride solution and extracted with diethyl ether. The organic phase was washed with a dilute aqueous potassium carbonate solution, with water and with brine, dried (MgSO₄)and evaporated. The residue was purified by column chromatography using a 10:1 mixture of hexane and ethyl acetate as eluent. There was thus obtained 4'-(4-bromothien-2-ylthio)acetophenone ethylene acetal (1.64 g, 78%) as an oil;

NMR Spectrum 1.65 (s, 3H), 3.7–3.8 (m, 2H), 4.0–4.1 (m, 2H), 7.2–7.5 (m, 6H).

n-Butyl-lithium (1.6M in hexane, 3 ml) was added to a solution of the ethylene acetal so obtained in diethyl ether (40 ml) which had been cooled to –78° C. The mixture was stirred at –78° C. for 1 hour. A solution of 1-tetrahydropyran-2-yloxypropan-2-one (0.77 g) in THF (4 ml) was added dropwise. The mixture was stirred at –70° C. for 2 hours and at ambient temperature for 16 hours. The mixture was partitioned between diethyl ether and a saturated aqueous ammonium chloride solution. The organic phase was washed with brine, dried (MgSO₄)and evaporated. The residue was purified by column chromatography using a 10:3 mixture of toluene and ethyl acetate as eluent. There was thus obtained 4'-[4-(2-hydroxy-1-tetrahydropyran-2-yloxyprop-2-yl)thien-2-ylthio]acetophenone ethylene acetal (1 g, 50%) as a gum;

NMR Spectrum 1.5–1.7 (m, 12H), 3.4–4.1 (m, 8H), 4.6 (m, 1H), 7.1–7.4 (m, 6H).

A mixture of the ethylene acetal so obtained, 2N aqueous hydrochloric acid (3 ml) and methanol (12 ml) was stirred at ambient temperature for 1.5 hours. The bulk of the methanol was evaporated and the residue was partitioned between ethyl acetate and dilute aqueous potassium carbonate solution. The organic phase was washed with brine, dried (MgSO₄)and evaporated. The residue was purified by column chromatography using increasingly polar mixtures of toluene and ethyl acetate as eluent. There was thus obtained 4'-[4-(1,2-dihydroxyprop-2-yl)thien-2-ylthio]acetophenone (6.0 g, 85%) as a gum;

NMR Spectrum (CD₃SOCD₃) 1.4 (s, 3H), 2.5 (s, 3H), 3.4 (broad s, 2H), 4.8 (broad s, 1H), 5.0 (broad s, 1H), 7.4 (d, 1H), 7.6 (d, 1H), 7.2 (d, 2H), 7.9 (d, 2H).

A mixture of a portion (0.2 g) of the acetophenone so obtained, hydroxylamine hydrochloride (0.24 g), sodium acetate (0.29 g) and ethanol (3 ml) was stirred and heated to 100° C. for 1.5 hours. The bulk of the ethanol was evaporated and the residue was partitioned between ethyl acetate and brine. The organic phase was dried (MgSO₄) and evaporated. The residue was purified by column chromatography using a 5:4 mixture of toluene and ethyl acetate as eluent. There was thus obtained (E)-4'-[4-(1,2-dihydroxyprop-2-yl)thien-2-ylthio]acetophenone oxime (0.21 g, 99%) as a gum.

EXAMPLE 68

A mixture of 4'-[4-(2,2,4-trimethyl-1,3-dioxolan-4-yl)thien-2-ylthio]acetophenone (0.14 g), O-methylhydroxylamine hydrochloride (0.16 g), sodium acetate (0.16 g) and ethanol (3 ml) was stirred and heated to reflux for 1.5 hours. The bulk of the ethanol was evaporated and the residue was partitioned between ethyl acetate and water. The organic phase was washed with brine, dried (MgSO₄)and evaporated. The residue was purified by column chromatography using a 10:1 mixture of hexane and ethyl acetate as eluent. There was thus obtained (E)-4'-[4-(2,2,4-trimethyl-1,3-dioxolan-4-yl)thien-2-ylthio]acetophenone oxime O-methyl ether (0.146 g, 97%) as an oil;

NMR Spectrum 1.45 (s, 3H), 1.5 (s, 3H), 1.62 (s, 3H), 2.2 (s, 3H), 3.9–4.1 (m 5H), 7.25 (m, 1H), 7.3 (m, 1H), 7.15–7.2 (d, 2H), 7.5–7.6 (d, 2H).

The 4'-[4-(2,2,4-trimethyl-1,3-dioxolan-4-yl)thien-2-ylthio]acetophenone used as a starting material was obtained as follows:

A mixture of 4'-[4-(1,2-dihydroxyprop-2-yl)thien-2-ylthio]acetophenone (0.2 g), acetone dimethyl acetal (10% solution in acetone, 0.9 ml), 4-toluenesulphonic acid (0.014 g) and acetone (5 ml) was stirred and heated to 70° C. for 1 hour. The mixture was cooled to ambient temperature and neutralized by the addition of dilute aqueous potassium carbonate solution. The mixture was evaporated and the residue was partitioned between ethyl acetate and water. The organic phase was washed with brine, dried (MgSO$_4$)and evaporated. The residue was purified by column chromatography using a 7:3 mixture of hexane and ethyl acetate as eluent. There was thus obtained the required starting material (0.17 g, 75%) as a gum;

NMR Spectrum 1.45 (s, 3H), 1.53 (s, 3H), 1.65 (s, 3H), 2.15 (s, 3H), 4.0–4.1 (q, 2H), 7.15–7.2 (d, 2H), 7.3 (d, 1H), 7.4 (d, 1H), 7.8–7.9 (d, 2H).

EXAMPLE 69

A mixture of 4'-[3-(4-methoxytetrahydropyran-4-yl)phenylthio]acetophenone (0.28 g), hydroxylamine hydrochloride (0.074 g) and pyridine (3 ml) was stirred and heated to 60° C. for 6 hours. The mixture was cooled to ambient temperature and partitioned between ethyl acetate and dilute aqueous hydrochloric acid. The organic phase was washed with brine, dried (MgSO$_4$)and evaporated. The residue was purified by column chromatography using a 10:3 mixture of petroleum ether and ethyl acetate as eluent. There was thus obtained (E)-4'-[3-(4-methoxytetrahydropyran-4-yl)phenylthio]acetophone oxime (0.2 g, 69%), m.p. 142°–144° C.;

NMR Spectrum 1.85–1.95 (m, 4H), 2.17 (s, 3H), 2.86 (s, 3H), 3.6–3.75 (m, 4H), 7.2–7.5 (m, 6H), 7.65 (m, 2H).

The 4'-[3-(4-methoxytetrahydropyran-4-yl)phenylthio]acetophenone used as starting material was obtained as follows:

n-Butyl-lithium (1.6M in hexane, 25 ml) was added dropwise to a stirred solution of 1,3-dibromobenzene (9.36 g) in THF (47 ml) which had been cooled to −65° C. The mixture was stirred at −65° C. for 30 minutes. Tetrahydropyran-4-one (4 g) was added. The mixture was stirred at −65° C. for 1 hour and then allowed to warm to ambient temperature. The mixture was partitioned between diethyl ether and dilute aqueous hydrochloric acid. The organic phase was washed with brine, dried (MgSO$_4$)and evaporated. There was thus obtained 4-(3-bromophenyl)-4-hydroxytetrahydropyran (7.78 g, 78%).

Sodium hydride (60%, 1.6 g) was added portionwise to a stirred solution of 4-(3-bromophenyl)-4-hydroxytetrahydropyran (8.53 g) in DMF (35 ml) and the mixture was stirred at ambient temperature for 2 hours. Methyl iodide (4 ml) was added and the mixture was stirred at ambient temperature for 2.5 hours. The mixture was poured into water, acidified to pH5 by the addition of dilute hydrochloric acid and extracted with diethyl ether. The organic phase was washed with brine, dried (MgSO$_4$) and evaporated. The residue was purified by column chromatography using a 15:1 mixture of methylene chloride and diethyl ether as eluent. There was thus obtained 4-(3-bromophenyl)-4-methoxytetrahydropyran (6.87 g, 76%).

Potassium tert-butoxide (0.112 g) and tetrakis(triphenylphosphine)palladium(O) (0.092 g) were added in turn to a stirred solution of 4-(2-methyl-1,3-dioxolan-2-yl)benzenethiol (0.2 g) and 4-(3-bromophenyl)-4-methoxytetrahydropyran (0.27 g) in DMSO (2 ml). The mixture was heated to 110° C. for 15 minutes. The mixture was cooled to ambient temperature and partitioned between ethyl acetate and water. The organic phase was washed with brine, dried (MgSO$_4$)and evaporated. The residue was purified by column chromatography using a 5:1 mixture of petroleum ether and ethyl acetate as eluent. There was thus obtained 4-methoxy-4-[3-[4-(2 -methyl-1,3-dioxolan-2-yl)phenylthio]phenyl]tetrahydropyran as an oil (0.338 g, 87%).

2N aqueous hydrochloric acid (6 drops) was added to a solution of the product so obtained in acetone (8 ml). The mixture was stirred at ambient temperature for 7 hours. The mixture was neutralized by the addition of sodium bicarbonate. The mixture was evaporated and the residue was purified by column chromatography using a 10:3 mixture of petroleum ether and ethyl acetate as eluent. There was thus obtained 4'-[3-(4-methoxytetrahydropyran-4-yl)phenylthio] acetophenone as an oil (0.28 g, 96%).

EXAMPLE 70

Using an analogous procedure to that described in Example 69, 4'-[5-fluoro-3-(4-methoxytetrahydropyran-4-yl)phenylthio]-α-hydroxyacetophenone was reacted with hydroxylamine hydrochloride to give (E)-4'-[5-fluoro-3-(4-methoxytetrahydropyran-4-yl)phenylthio]-α-hydroxyacetophenone oxime in 59% yield, m.p. 145°–146° C.;

NMR Spectrum 1.85–2.05 (m, 4H), 2.80 (broad s, 1H), 2.99 (s, 3H), 3.75–3.85 (m, 4H), 4.75 (s, 2H), 6.83–7.02 (m, 2H), 7.17 (m, 1H), 7.37 (m, 2H), 7.60 (m, 2H), 8.53 (broad s, 1H).

The 4'-[5-fluoro-3-(4-methoxytetrahydropyran-4-yl)phenylthio]-α-hydroxyacetophenone used as a starting material was obtained as follows:

Bromine (0.516 ml) was added dropwise to a stirred mixture of 4'-[5-fluoro-3-(4-methoxytetrahydropyran-4-yl)phenylthio]acetophenone (3.6 g), aluminum chloride (0.05 g) and diethyl ether (250 ml) which had been cooled to 0° C. The mixture was stirred at 0° C. for 1 hour. The mixture was partitioned between ethyl acetate and water. The organic phase was washed with brine, dried (MgSO$_4$) and evaporated. There was thus obtained α-bromo-4'-[5-fluoro-3-(4 -methoxytetrahydropyran-4-yl)phenylthio]acetophenone (4.3 g, 98%), m.p. 112°–114° C.

Sodium formate (0.612 g) was added to a mixture of a portion (0.657 g) of the material so obtained, water (1.5 ml) and ethanol (8.5 ml). The mixture was stirred and heated to reflux for 0.75 hours. The mixture was cooled to ambient temperature and partitioned between ethyl acetate and water. The organic phase was washed with brine, dried (MgSO$_4$)and evaporated. The residue was purified by column chromatography using a 7:3 mixture of petroleum ether and ethyl acetate as eluent. There was thus obtained 4'-[5-fluoro-3-(4 -methoxytetrahydropyran-4-yl)phenylthio]-α-hydroxyacetophenone as an oil (0.24 g, 42%).

EXAMPLE 71

Using an analogous procedure to that described in Example 69, 4'-[5-fluoro-3-(4-methoxytetrahydropyran-4-yl)phenylthio]-α,α,α-trifluoroacetophenone was reacted with hydroxylamine hydrochloride to give 4'-[5-fluoro-3-(4-methoxytetrahydropyran-4-yl)phenylthio]-α,α,α-trifluoroacetophenone oxime in 70% yield, m.p. 131°–133° C.;

NMR Spectrum 1.84–2.02 (m, 4H), 2.99 (s, 3H), 3.78–3.87 (m, 4H), 6.9–7.06 (m, 2H), 7.18–7.50 (m, 5H), 8.5 and 8.8 (2s's, 1H).

The 4'-[5-fluoro-3-(4-methoxytetrahydropyran-4-yl)phenylthio]-α,α,α-trifluoroacetophenone used as a starting material was obtained as follows:

n-Butyl-lithium (1.6M in hexane, 10 ml) was added dropwise to a solution of 1,4-diiodobenzene (5.05 g) in THF (30 ml) which had been cooled to −65° C. The mixture was stirred at −60° C. for 15 minutes and then added to a solution of ethyl trifluoroacetate (1.82 ml) in diethyl ether (30 ml) which had been cooled to −60° C. The mixture was stirred and allowed to warm to ambient temperature. The mixture was partitioned between diethyl ether and dilute aqueous hydrochloric acid. The organic phase was washed with brine, dried (MgSO$_4$) and evaporated. The residue was purified by column chromatography using a 12:1 mixture of petroleum ether and ethyl acetate as eluent. There was thus obtained 4'-iodo-α,α,α-trifluoroacetophenone as an oil (3.22 g, 72%).

Using an analogous procedure to that described in the portion of Example 1 which is concerned with the preparation of starting materials except that the reaction mixture was heated to 120° C. for 1 hour, the product so obtained was reacted with 4-(5-fluoro-3-mercaptophenyl)-4-methoxytetrahydropyran to give 4'-[5-fluoro-3-(4-methoxytetrahydropyran-4-yl)phenylthio]-α,α,α-trifluoroacetophenone in 66% yield, m.p. 63° C.

EXAMPLE 72

Using an analogous procedure to that described in Example 43, 4'-[2-amino-6-(4-methoxytetrahydropyran-4-yl)pyrimidin-4-ylthio]acetophenone was reacted with hydroxylamine hydrochloride to give (E)-4'-[2-amino-6-(4-methoxytetrahydropyran-4-yl)pyrimidin-4-ylthio]acetophenone oxime in 75% yield, m.p. 237°–240° C.;

NMR Spectrum (CD$_3$SOCD$_3$) 1.5–1.65 (m, 2H), 1.9–2.05 (m, 2H), 2.20 (s, 3H), 2.90 (s, 3H), 3.4–3.7 (m, 4H), 6.11 (s, 1H), 6.76 (s, 2H), 7.63 (d, 2H), 7.79 (d, 2H).

The 4'-[2-amino-6-(4-methoxytetrahydropyran-4-yl)pyrimidin-4-ylthio]acetophenone used as a starting material was obtained as follows:

Using an analogous procedure to that described in the second paragraph of the portion of Example 43 which is concerned with the preparation of starting materials, 4-(4-bromo-2-methylthiopyrimidin-6-yl)-4-methoxytetrahydropyran was reacted with 3-chloroperoxybenzoic acid to give 4-(4-bromo-2-methylsulphonylpyrimidin-6-yl)-4-methoxytetrahydropyran in 60% yield.

Sodium hydride (50%, 0.075 g) was added portionwise to a mixture of the product so obtained (0.5 g), 4-(2-methyl-1,3-dioxolan-2-yl)benzenethiol (0.307 g) and DMF (10 ml) which had been cooled to 0° C. The mixture was stirred at ambient temperature for 1 hour. The mixture was partitioned between ethyl acetate and water. The organic phase was washed with brine, dried (MgSO$_4$) and evaporated. The residue was purified by column chromatography using a 9:1 mixture of methylene chloride and ethyl acetate as eluent. There was thus obtained 4-methoxy-4-{4-[4-(2-methyl-1,3-dioxolan-2-yl)phenylthio]-2-methylsulphonylpyrimidin-6-yl}tetrahydropyran (0.46 g, 70%).

A mixture of the material so obtained and a saturated solution (40 ml) of ammonia in ethanol was heated to 100° C. in an autoclave for 3 hours. The mixture was evaporated and the residue was purified by column chromatography using a 3:2 mixture of methylene chloride and ethyl acetate as eluent. There was thus obtained 4-{2 -amino-4-[4-(2-methyl-1,3-dioxolan-2-yl)phenylthio]pyrimidin-6-yl}-4-methoxytetrahydropyran (0.257 g, 64%).

A mixture of the material so obtained, 12N aqueous hydrochloric acid (0.056 ml), 2N aqueous hydrochloric acid (5 drops) and acetone (10 ml) was stirred at ambient temperature for 30 minutes. The mixture was evaporated and the residue was partitioned between methylene chloride and sodium bicarbonate. The organic phase was dried (MgSO$_4$) and evaporated. There was thus obtained 4'-[2-amino-6-(4-methoxytetrahydropyran-4-yl)pyrimidin-4-ylthio]acetophenone (0.207 g, 93%), m.p. 185°–188° C.

EXAMPLE 73

Using an analogous procedure to that described in Example 7, 7-[4-(4-methoxytetrahydropyran-4-yl)thien-2-ylthio]chroman-4-one was reacted with hydroxylamine hydrochloride to give (E)-7-[4-(4 -methoxytetrahydropyran-4-yl)thien-2-ylthio]chroman-4-one oxime in 82% yield, m.p. 137°–138° C.;

NMR Spectrum 1.92–2.08 (m, 4H), 2.95 (t, 2H), 3.03 (s, 3H), 3.72–3.88 (m, 4H), 4.21 (t, 2H), 6.6–6.75 (m, 2H), 7.27 (m, 2H), 7.6–7.72 (m, 2H).

The 7-[4-(4-methoxytetrahydropyran-4-yl)thien-2-ylthio]chroman-4-one used as a starting material was obtained as follows:

A solution of sodium hydrosulfide hydrate (8.88 g) in NMP (150 ml) was stirred and heated to 140° C. The mixture was partially evaporated under vacuum to remove the water. The mixture was cooled to 45° C. and a solution of 7-bromochroman-4-one (12 g) in NMP (150 ml) was added dropwise. The mixture was stirred and heated to 50° C. for 30 minutes. The mixture was poured onto a mixture of ice and water and extracted with ethyl acetate. The organic phase was dried (MgSO$_4$) and evaporated to give 7-mercaptochroman-4-one (7 g, 73%).

A solution of the material so obtained in DMSO (20 ml) was stirred at ambient temperature for 16 hours. The mixture was poured onto a mixture of ice and water. The precipitate was isolated and dried. The crude product (5.4 g) was purified by column chromatography using a 19:1 mixture of methylene chloride and diethyl ether as eluent. There was thus obtained di-(4-oxochroman-7-yl)disulphide (2.1 g, 30%), m.p. 144°–145° C.

After repetition of the above-mentioned reactions, a mixture of the disulphide so obtained (7 g), ethylene glycol (18 ml), triethyl orthoformate (18.5 ml) and 4-toluenesulphonic acid (0.43 g) was stirred and heated to 40° C. for 4 hours. The mixture was cooled to ambient temperature and partitioned between diethyl ether and a saturated aqueous sodium bicarbonate solution. The organic phase was dried (MgSO$_4$) and evaporated. The residue was purified by column chromatography using methylene chloride as eluent. There was thus obtained di-[4-(2-methyl-1,3-dioxolan-2-yl)chroman-7-yl]disulphide (5.2 g, 60%), m.p. 130°–132° C.

Using analogous procedures to those described in the fourth and fifth paragraphs of the portion of Example 7 which is concerned with the preparation of starting materials, the disulphide so obtained was reacted with 4-methoxy-4-(3-thienyl)tetrahydropyran and the resultant product was treated with 2N aqueous hydrochloric acid. There was thus obtained 7-[4-(4-methoxytetrahydropyran-4-yl)thien-2-ylthiolchroman-4-one in 42% yield, m.p. 97°–98° C.

EXAMPLE 74

Using an analogous procedure to that described in Example 50, 5-[5-fluoro-3-(4-methoxytetrahydropyran-4- yl)phenylsulphonyl]indan-1-one was reacted with hydroxylamine hydrochloride to give (E)-5-[5-fluoro-3-(4-methoxytetrahydropyran-4-yl)phenylsulphonyl]indan-1-one oxime in 49% yield, m.p. 225°–226° C.;

NMR Spectrum (CD$_3$SOCD$_3$) 1.82–2.02 (m, 4H), 2.82 (m, 2H), 2.91 (s, 3H), 3.09 (m, 2H), 3.61–3.78 (m, 4H), 7.58 (m, 1H), 7.73–7.82 (m, 3H), 7.91 (m, 1H), 8.07 (m, 1H).

The 5-[5-fluoro-3-(4-methoxytetrahydropyran-4-yl)phenylsulphonyl]indan-1-one used as a starting material was obtained as follows:

3-Chloroperoxybenzoic acid (50%, 0.555 g) was added portionwise to a stirred solution of 5-[5-fluoro-3-(4-methoxytetrahydropyran-4-yl)phenylthio] indan-1-one (0.2 g) in methylene chloride (4 ml) which had been cooled to 0° C. The mixture was stirred at 0° C. for 10 minutes. The mixture was partitioned between ethyl acetate and a saturated aqueous sodium bicarbonate solution. The organic phase was washed with water, dried (MgSO$_4$) and evaporated. The residue was purified by column chromatography using a 3:2 mixture of petroleum ether and ethyl acetate as eluent. There was thus obtained the required starting material (0.12 g, 55%).

EXAMPLE 75

Using an analogous procedure that described in Example 66, 4'-{5-fluoro-3-[(2RS,3SR)-3-methoxy-2-methyltetrahydrofuran-3 -yl]phenylthio}propiophenone was reacted with hydroxylamine hydrochloride to give 4'-{5-fluoro-3-[(2RS,3SR)-3-methoxy-2 -methyltetrahydrofuran-3-yl]phenylthio}propiophenone oxime in 15% yield, m.p. 113°–114° C.

The 4'-{5-fluoro-3-[(2RS,3SR)-3-methoxy-2-methyltetrahydrofuran-3-yl]phenylthio}propiophenone used as a starting material was obtained as follows:

Using an analogous procedure to that described in the last paragraph of the portion of Example 66 which is concerned with the preparation of starting materials, 4'-fluoropropiophenone was reacted with (2RS,3SR)-3-(5-fluoro-3-mercaptophenyl)-3-methoxy-2-methyltetrahydrofuran to give the required starting material in 70% yield as an oil;

NMR Spectrum (CD$_3$SOCD$_3$) 0.95 (d, 3H), 1.1 (t, 3H), 2.5 (m, 2H), 3.0 (q, 2H), 3.1 (s, 3H), 3.6 (q, 1H), 3.9 (m, 2H), 7.2–7.4 (m, 5H), 7.9 (d, 2H).

EXAMPLE 76

Using an analogous procedure to that described in Example 66, 4'{5-fluoro-3-[(2RS,3SR)-3-methoxy-2-methyltetrahydrofuran-3-yl]phenoxy}propiophenone was reacted with hydroxylamine hydrochloride to give 4'-{5-fluoro-3-{(2RS,3SR)-3-methoxy-2-methyltetrahydrofuran-3-yl]phenoxy}propiophenone oxime in 83% yield, m.p. 94°–96° C.

The 4'-{5-fluoro-3-[(2RS,3SR)-3-methoxy-2-methyltetrahydrofuran-3-yl]phenoxy}propiophenone starting material was obtained as follows:

A mixture of 4'-fluoropropiophenone (0.6 g), (2RS,3SR)-3-(5-fluoro-3-hydroxyphenyl)-3-methoxy-2-methyltetrahydrofuran (European Patent Application No. 0385662, Example 10, Note c. thereof, 0.452 g), potassium carbonate (0.6 g) and DMF (10 ml) was stirred and heated to reflux for 3 hours. The mixture was cooled to ambient temperature and partitioned between ethyl acetate and water. The organic phase was washed with water and with brine, dried (MgSO$_4$) and evaporated. The residue was purified by column chromatography using a 3:1 mixture of hexane and ethyl acetate as eluent. There was thus obtained the required starting material in 78% yield as a gum.

NMR Spectrum (CD$_3$SOCD$_3$) 1.0 (d, 3H), 1.1 (t, 3H), 2.5 (m, 2H), 3.0 (q, 2H), 3.1 (s, 3H), 3.7 (q, 1H), 3.9 (m, 2H), 6.9–7.2 (m, 5H), 8.0 (d, 2H).

EXAMPLE 77

Using an analogous procedure to that described in Example 66, 4'-{5-fluoro-3-[(2RS,3SR)-3-methoxy-2-methyltetrahydrofuran-3-yl]phenoxy}acetophenone was reacted with hydroxylamine hydrochloride to give (E)-4'-{5-fluoro-3-[(2RS,3SR)-3-methoxy-2-methyltetrahydrofuran-3-yl] phenoxy}acetophenone oxime in 42% yield, m.p. 126°–127° C.

The 4'-{5-fluoro-3-[(2RS,3SR)-3-methoxy-2-methyltetrahydrofuran-3-yl]phenoxy}acetophenone used as a starting material was obtained as follows;

Using an analogous procedure to that described in the portion of Example 76 which is concerned with the preparation of starting materials, 4'-fluoroacetophenone was reacted with (2RS,3SR)-3-(5-fluoro-3-hydroxyphenyl)-3-methoxy-2-methyltetrahydrofuran to give the required starting material in 95% yield as a gum.

NMR Spectrum 1.2 (d, 3H), 2.4 (m, 2H), 2.6 (s, 3H), 3.2 (s, 3H), 3.7 (m, 1H), 4.1 (m, 2H), 6.6–7.1 (m, 5H), 8.0 (m, 2H).

EXAMPLE 78

Using an analogous procedure to that described in Example 66, 5-{5-fluoro-3-[(2RS,3SR)-3-methoxy-2-methyltetrahydrofuran-3-yl]phenylthio}indan-1-one was reacted with hydroxylamine hydrochloride to give (E)-5-{5-fluoro-3-[(2RS,3SR)-3-methoxy-2-methyltetrahydrofuran-3-yl] phenylthio}indan-1-one oxime in 48% yield, m.p. 136°–137° C.

The 5-{5-fluoro-3-[(2RS,3SR)-3-methoxy-2-methyltetrahydrofuran-3-yl]phenylthio} indan-1-one used as a starting material was obtained as follows:

Using an analogous procedure to that described in the last paragraph of the portion of Example 66 which is concerned with the preparation of starting materials, 5-bromoindan-1-one was reacted with (2RS,3SR)-3-(5-fluoro-3-mercaptophenyl)-3-methoxy-2-methyltetrahydrofuran to give the required starting material in 79% yield.

NMR Spectrum (CD$_3$SOCD$_3$) 1.0 (d, 3H), 2.5 (m, 2H), 2.6 (m, 2H), 3.1 (m, 2H), 3.1 (s, 3H), 3.7 (q, 1H), 3.9 (m, 2H), 7.2–7.6 (m, 6H).

EXAMPLE 79

Using an analogous procedure to that described in Example 66, 7-{5-fluoro-3-[4-(2RS,3SR)-3-methoxy-2-methyltetrahydrofuran-3-yl]phenylthio}chroman-4-one was reacted with hydroxylamine hydrochloride to give (E)-7-{5-fluoro-3-[4-(2RS,3SR)-3-methoxy-2 -methyltetrahydrofuran-3-yl]phenylthio}chroman-4-one oxime in 71% yield as a gum.

NMR Spectrum 1.2 (d, 3H), 2.5 (m, 2H), 3.0 (t, 2H), 3.2 (s, 3H), 3.7 (q, 1H), 4.0 (m, 2H), 4.2 (t, 2H), 6.8–7.8 (m, 6H).

The 7-{5-fluoro-3-[4-(2RS,3SR)-3-methoxy-2-methyltetrahydrofuran-3-yl]phenylthio}chroman-4-one used as a starting material was obtained as follows:

Using an analogous procedure to that described in the portion of Example 25 which is concerned with the preparation of starting materials, 7-bromochroman-4-one was reacted with (2RS,3SR)-3-(5-fluoro-3-mercaptophenyl)-3-methoxy-2-methyltetrahydrofuran to give the required starting material in 51% yield as a gum.

NMR Spectrum (CD$_3$SOCD$_3$) 1.0 (d, 3H), 2.5 (m, 3H), 2.8 (t, 2H), 3.0 (s, 3H), 3.7 (q, 1H), 3.9 (m, 2H), 4.5 (t, 2H), 6.8–7.7 (m, 6H).

EXAMPLE 80

Using an analogous procedure to that described in Example 66, 4'-{4-[(2RS,3SR)-3-methoxy-2-methyltetrahydrofuran-3-yl]thien-2-ylthio}acetophenone was reacted with hydroxylamine hydrochloride to give (E)-4'-{4-[(2RS,3SR)-3-methoxy-2-methyltetrahydrofuran-3-yl] thien-2-ylthio}acetophenone oxime in 87% yield, m.p. 105°–107° C.

The 4'-{4-[(2RS,3SR)-3-methoxy-2-methyltetrahydrofuran-3-yl]thien-2-ylthio} acetophenone used as a starting material was obtained as follows:

n-Butyl-lithium (1.6M in THF, 28.5 ml) was added to a stirred mixture of 2,4-dibromothiophene (*J. Org. Chem.*, 1988, 53, 417; 10 g) and diethyl ether (150 ml) which had been cooled to −70° C. After 1 hour, a solution of dimethyl disulphide (3 ml) in diethyl ether (10 ml) was added and the mixture was stirred and allowed to warm to −20° C. during 1 hour. The mixture was poured into water. The organic phase was washed with brine, dried (MgSO$_4$) and evaporated. The residue was purified by column chromatography using hexane as eluent. There was thus obtained 4-bromo-2-methylthiothiophene (4.76 g, 90%).

n-Butyl-lithium (1.6M in THF, 18.5 ml) was added to a stirred solution of the material so obtained in diethyl ether (100 ml) which had been cooled to −70° C. After 15 minutes, a solution of 2-methyltetrahydrofuran-3-one (3 g) in diethyl ether (8 ml) was added. The mixture was stirred at −70° C. for 30 minutes and then allowed to warm to ambient temperature. The mixture was poured into water. The organic phase was washed with brine, dried (MgSO$_4$)and evaporated. The residue was purified by column chromatography using a 5:2 mixture of hexane and ethyl acetate as eluent. There was thus obtained (2RS,3SR)-3-hydroxy-2-methyl-3-(2-methylthiothien-4-yl)tetrahydrofuran (4.05 g, 63%).

NMR Spectrum 1.1 (d, 3H), 2.0 (s, 1H), 2.2 (m, 1H), 2.5 (m, 4H), 3.9–4.2 (m, 3H), 7.0–7.2 (m, 2H).

Using an analogous procedure to that described in the second paragraph of the portion of Example 66 which is concerned with the preparation of starting materials, the product so obtained was reacted with methyl iodide to give (2RS,3SR)-3-methoxy-2-methyl-3-(2-methylthiothien-4-yl)tetrahydrofuran in 72% yield as an oil.

NMR Spectrum 1.2 (d, 3H), 2.4 (m, 2H), 2.5 (s, 3H), 3.2 (s, 3H), 3.7 (q, 1H), 4.0 (m, 2H), 7.0–7.2 (m, 2H).

A mixture of the product so obtained (3.06 g), sodium methanethiolate (1.32 g) and DMF (40 ml) was stirred and heated to 130° C. for 90 minutes. The mixture was cooled to ambient temperature and partitioned between ethyl acetate and water. The mixture was acidified by the addition of a 1M aqueous citric acid solution. The organic layer was washed with water and with brine, dried (MgSO$_4$) and evaporated. There was thus obtained (2RS,3SR)-3-(2-mercaptothien-4-yl)-3-methoxy-2-methyltetrahydrofuran (1.79 g, 62%) as a liquid.

NMR Spectrum 1.2 (d, 3H), 2.4 (m, 2H), 3.2 (s, 3H), 3.6 (s, 1H), 3.8 (q, 1H), 4.0 (m, 2H), 7.0–7.2 (m, 2H).

Using an analogous procedure to that described in the last paragraph of the portion of Example 66 which is concerned with the preparation of starting materials, the product so obtained was reacted with 4'-fluoroacetophenone to give 4'-{4-[(2RS,3SR)-3-methoxy-2-methyltetrahydrofuran-3-yl]thien-2-ylthio}acetophenone in 83% yield as an oil.

NMR Spectrum 1.1 (d, 3H), 2.4 (m, 2H), 2.6 (s, 3H), 3.2 (s, 3H), 3.8 (q, 1H), 4.0 (m, 2H), 7.1–7.8 (m, 6H).

EXAMPLE 81

Using an analogous procedure to that described in Example 66, 5-{4-[(2RS,3SR)-3-methoxy-2-methyltetrahydrofuran-3-yl]thien-2-ylthio}indan-1-one was reacted with hydroxylamine hydrochloride to give (E)-5-{4-[(2RS,3SR)-3-methoxy-2-methyltetrahydrofuran-3-yl]thien-2-ylthio}indan-1-one oxime in 64% yield, m.p. 149°–151° C.

The 5-{4-[(2RS,3SR)-3-methoxy-2-methyltetrahydrofuran-3-yl] thien-2-ylthio}indan-1-one used as a starting material was obtained as follows:

Using an analogous procedure to that described in the last paragraph of the portion of Example 66 which is concerned with the preparation of starting materials, 5-bromoindan-1-one was reacted with (2RS,3SR)-3-(2-mercaptothien-4-yl)-3-methoxy-2-methyltetrahydrofuran to give the required starting material in 83% yield as a gum.

NMR Spectrum 1.2 (d, 3H), 2.5 (m, 4H), 3.1 (t, 2H), 3.3 (s, 3H), 3.8 (q, 1H), 4.0 (m, 2H), 7.1–7.6 (m, 5H).

EXAMPLE 82

Using an analogous procedure to that described in Example 68, 4'-[4-(2,2-diethyl-4-methyl-1,3-dioxolan-4-yl)thien-2-ylthio]acetophenone was reacted with hydroxylamine hydrochloride to give (E)-4'-[4-(2,2-diethyl-4-methyl-1,3-dioxolan-4-yl)thien-2-ylthio]acetophenone oxime in 80% yield as a gum.

NMR Spectrum (CD$_3$SOCD$_3$) 0.75–0.95 (2 t's, 6H), 1.5 (s, 3H), 1.52–1.7 (m, 4H), 2.1 (s, 3H), 3.93–4.1 (m, 2H), 7.2 (d, 2H), 7.4 (m, 1H), 7.6 (m, 3H), 11.2 (broad s, 1H).

The 4'-[4-(2,2-diethyl-4-methyl-1,3-dioxan-4-yl)thien-2-ylthio]acetophenone used as a starting material was obtained as follows:

The procedure described in the portion of Example 68 which is concerned with the preparation of starting materials was repeated except that diethyl ketone was used in place of acetone. There was thus obtained the required starting material in 24% yield as an oil.

EXAMPLE 83

Using an analogous procedure to that described in Example 68, 4'-[4-(2-cyclopropyl-4-methyl-1,3-dioxolan-4-yl)thien-2-ylthio]acetophenone was reacted with hydroxylamine hydrochloride to give 4'-[4-(2-cyclopropyl-4-methyl-1,3-dioxolan-4 -yl)thien-2-ylthio]acetophenone oxime in 50% yield as an oil.

NMR Spectrum (CD$_3$SOCD$_3$) 0.3–0.6 (m, 4H), 1.0–1.2 (m, 1H), 1.55 (s, 3H), 2.11 (s, 3H), 3.97–4.05 (m, 2H), 4.6 (m, 1H), 7.2 (m, 2H), 7.4 (d, 1H), 7.6–7.7 (m, 3H), 11.2 (broad s, 1H).

The 4'-[4-(2-cyclopropyl-4-methyl-1,3-dioxolan-4-yl)thien-2-ylthio]acetophenone used as a starting material was obtained as follows:

A mixture of 4'-[4-(1,2-dihydroxyprop-2-yl)thien-2-ylthio]acetophenone (0.2 g), cyclopropoanecarbaldehyde (3 ml) and 4-toluenesulphonic acid (0.01 g) was stirred at ambient temperature for 16 hours. The mixture was neutralized by the addition of a saturated aqueous sodium bicarbonate solution. The mixture was evaporated and the residue was partitioned between ethyl acetate and water. The organic phase was washed with brine, dried ($MgSO_4$) and evaporated. The residue was purified by column chromatography using a 10:3 mixture of toluene and ethyl acetate as eluent. There was thus obtained the required starting material (0.076 g, 32%) as a gum.

NMR Spectrum ($CD_3SOCD_3$) 0.3–0.6 (m, 4H), 1.0–1.2 (m, 1H), 1.55 (s, 3H), 2.5 (s, 3H), 3.7–4.1 (m, 2H), 4.6 (m, 1H), 7.2 (d, 2H), 7.5 (d, 1H), 7.7 (d, 1H), 7.9 (d, 2H).

EXAMPLE 84

Using an analogous procedure to that described in Example 68, 5-[4-(2,2,4-trimethyl-1,3-dioxolan-4-yl)thien-2-ylthio]indan-1-one was reacted with hydroxylamine hydrochloride to give (E)-5-[4-(2,2,4-trimethyl-1,3-dioxolan-4-yl)thien-2-ylthio]indan-1-one oxime in 60% yield as a foam.

NMR Spectrum ($CD_3SOCD_3$) 1.3 (s, 3H), 1.4 (s, 3H), 1.55 (s, 3H), 2.7–3.0 (m, 4H), 3.9–4.1 (m, 2H), 7.0–7.6 (m, 5H), 10.85 (broad s, 1H).

The 5-[4-(2,2,4-trimethyl-1,3-dioxolan-4-yl)thien-2-ylthio] indan-1-one used as a starting material was obtained as follows:

n-Butyl-lithium (1.5M in hexane, 16.6 ml) was added to a stirred solution of 4-bromo-2-methylthiothiophene (5.2 g) in diethyl ether (150 ml) which had been cooled to −78° C. The mixture was stirred at −70° C. for 1 hour. A solution of 1-tetrahydropyran-2-yloxypropan-2-one (4.3 g) in diethyl ether (5 ml) was added. The mixture was stirred at −70° C. for 1 hour and then allowed to warm to −30° C. The mixture was poured onto a mixture of ice and a saturated aqueous solution of ammonium chloride. The mixture was extracted with diethyl ether. The organic layer was washed with brine, dried ($MgSO_4$) and evaporated. The residue was purified by column chromatography using a 10:3 mixture of hexane and ethyl acetate as eluent. There was thus obtained 4-(2-hydroxy-1-tetrahydropyran-2-yloxyprop-2-yl)-2-methylthiophene (5.35 g, 75%) as an oil.

A mixture of the product so obtained, 2N aqueous hydrochloric acid (3 ml) and methanol (20 ml) was stirred at ambient temperature for 1.5 hours. The bulk of the methanol was evaporated and the residue was partitioned between ethyl acetate and a dilute aqueous potassium carbonate solution. The organic phase was washed with brine, dried ($MgSO_4$) and evaporated. The residue was purified by column chromatography using a 2:1 mixture of hexane and ethyl acetate as eluent. There was thus obtained 4-(1,2-dihydroxyprop-2-yl)-2-methylthiothiophene (3.08 g, 82%), m.p. 40°–42° C.

A mixture of a portion (1 g) of the compound so obtained, acetone dimethyl acetal (1 ml), 4-toluenesulphonic acid (0.01 g) and acetone (12 ml) was stirred and heated to reflux for 45 minutes. The mixture was cooled to ambient temperature and neutralized by the addition of a dilute aqueous potassium carbonate solution. The mixture was extracted with ethyl acetate. The organic phase was washed with brine, dried ($MgSO_4$) and evaporated. The residue was purified by column chromatography using a 20:1 mixture of hexane and ethyl acetate as eluent. There was thus obtained 4-(2,2,4-trimethyl-1,3-dioxolan-4-yl)-2-methylthiothiophene (0.97 g, 81%) as an oil.

A mixture of a portion (0.347 g) of the material so obtained, sodium methanethiolate (0.35 g) and DMF (4 ml) was stirred and heated to 130° C. for 30 minutes. The mixture was cooled to ambient temperature and partitioned between diethyl ether and a dilute aqueous citric acid solution. The organic phase was washed with brine, dried ($MgSO_4$) and evaporated. There was thus obtained 4-(2,2,4-trimethyl-1,3-dioxolan-4-yl)-2-mercaptothiophene as an oil.

Using an analogous procedure to that described in the last paragraph of the portion of Example 66 which is concerned with the preparation of starting materials, the product so obtained was reacted with 5-bromoindan-1-one to give 5-[4-(2,2,4-trimethyl-1,3-dioxolan-4-yl)thien-2-ylthio]indan-1-one in 33% yield as an oil.

NMR Spectrum ($CD_3SOCD_3$) 1.35 (s, 3H), 1.4 (s, 3H), 1.6 (s, 3H), 2.60 (t, 2H), 3.05 (t, 2H), 4.02 (q, 2H), 7.1–7.8 (m, 5H).

EXAMPLE 85

Using an analogous procedure to that described in Example 68, 7-[4-(2,2,4-trimethyl-1,3-dioxolan-4-yl)thien-2-ylthio]chroman-4-one was reacted with hydroxylamine hydrochloride to give (E)-7-[4-(2,2,4-trimethyl-1,3-dioxolan-4-yl)thien-2-ylthio]chroman-4-one oxime in 65% yield as a gum.

NMR Spectrum ($CD_3SOCD_3$) 1,3 (s, 3H), 1.4 (s, 3H), 1.55 (s, 3H), 2.75–2.83 (t, 2H), 4.02 (q, 2H), 4.15 (t, 2H), 6.6 (d, 1H), 6.78 (m, 1H), 7.4 (d, 1H), 7.65–7.75 (m, 2H), 11.2 (broad s, 1H).

The 7-[4-(2,2,4-trimethyl-1,3-dioxolan-4-yl)thien-2-ylthio]chroman-4-one used as a starting material was obtained as follows:

Using an analogous procedure to that described in the portion of Example 25 which is concerned with the preparation of starting materials 7-bromochroman-4-one was reacted with 4-(2,2,4-trimethyl-1,3-dioxolan-4-yl)-2-mercaptothiophene to give the required starting material in 21% yield as a gum.

NMR Spectrum ($CD_3SOCD_3$) 1.35 (s, 3H), 1.4 (s, 3H), 1.55 (s, 3H), 2.73 (t, 2H), 4.02 (q, 2H), 4.50 (t, 2H), 6.6–7.7 (m, 5H).

EXAMPLE 86

Using an analogous procedure to that described in Example 68, 4'-[3-(2,2,4-trimethyl-1,3-dioxolan-4-yl)phenylthio]acetophenone was reacted with hydroxylamine hydrochloride to give (E)-4'-[3-(2,2,4-trimethyl-1,3-dioxolan-4-yl)phenylthio]acetophenone oxime in 51% yield as a gum.

NMR Spectrum 1.2 (s, 3H), 1.5 (s, 6H), 2.2 (s, 3H), 4.0 (m, 2H), 7.2 (m, 5H), 7.4 (m, 1H), 7.5 (m, 2H).

The 4'-[3-(2,2,4-trimethyl-1,3-dioxolan-4-yl)phenylthio]acetophenone used as a starting material was obtained as follows:

Using an analogous procedure to that described in the last paragraph of the portion of Example 66 which is concerned with the preparation of starting materials, 4'-fluoroacetophenone was reacted with 3-bromobenzenethiol to give 4'-(3-bromophenylthio)acetophenone in 82% yield, m.p. 54°–57° C.

A mixture of the material so obtained (17.9 g), ethylene glycol (14.46 g), triethyl orthoformate (34.5 g), 4-toluenesulphonic acid (1 g) and toluene (200 ml) was stirred and heated to 60° C. for 1 hour. The mixture was evaporated and the residue was partitioned between ethyl acetate and a dilute aqueous sodium carbonate solution. The organic phase was dried (MgSO$_4$)and evaporated. The residue was purified by column chromatography using a 4:1 mixture of hexane and ethyl acetate as eluent. There was thus obtained 4'-(3-bromophenyl)acetophenone ethylene acetal (16.1 g, 78%), m.p. 44°–45° C.

Using analogous procedures to those described in the second and third paragraphs of the portion of Example 67 which is concerned with the preparation of starting materials, the product so obtained was converted into 4'-[3-(1,2-dihydroxyprop-2-yl)phenylthio]acetophenone in 58% yield as a gum.

NMR Spectrum 1.5 (s, 3H), 2.5 (s, 3H), 2.7 (broad s, 1H), 3.65 (m, 2H), 7.2 (m, 2H), 7.3 (m, 3H), 7.6 (s, 1H), 7.8 (d, 2H).

Using an analogous procedure to that described in Example 67, the product so obtained was reacted with acetone dimethyl acetal to give 4'-[3-(2,2,4-trimethyl-1,3-dioxolan-4-yl)phenylthio]acetophenone in 57% yield as a gum.

NMR Spectrum 1.3 (s, 3H), 1.51 (s, 6H), 2.5 (s, 3H), 4.1 (m, 2H), 7.2 (m, 2H), 7.3 (m, 1H), 7.5 (m, 3H), 7.8 (m, 2H).

EXAMPLE 87

Using an analogous procedure to that described in Example 68, 4'-[3-(2,2,4-trimethyl-1,3-dioxolan-4-yl)phenylthio]acetophenone was reacted with O-methylhydroxylamine hydrochloride to give (E)-4'-[3-(2,2,4-trimethyl-1,3-dioxolan-4-yl)phenylthio]acetophenone oxime O-methyl ether in 60% yield as a gum.

NMR Spectrum 1.3 (s, 3H), 1.5 (s, 6H), 2.2 (s, 3H), 3.9 (s, 3H), 4.0 (m, 2H), 7.2 (m, 5H), 7.4 (s, 1H), 7.6 (d, 2H).

EXAMPLE 88

Using an analogous procedure to that described in Example 68, 4'-[3-(2,4-dimethyl-1,3-dioxolan-4-yl)phenylthio]acetophenone was reacted with hydroxylamine hydrochloride to give 4'-[3-(2,4-dimethyl-1,3-dioxolan-4-yl)phenylthio]acetophenone oxime in 82% yield as a gum.

NMR Spectrum 1.5 (s, 3H), 1.6 (s, 3H), 2.2 (s, 3H), 3.9 (m, 2H), 5.3 (m, 1H), 7.25 (m, 5H), 7.4 (s, 1H), 7.5 (m, 2H), 7.7 (broad s, 1H).

The 4'-{3-(2,4-dimethyl-1,3-dioxolan-4-yl)phenylthio] acetophenone used as a starting material was obtained as follows:

A mixture of 4'-[3-(1,2-dihydroryprop-2-yl)phenylthio] acetophenone (0.6 g), acetaldehyde (6.5 ml) and 4-toluenesulphonic acid (0.06 g) was stirred at ambient temperature for 1 hour. The mixture was partitioned between ethyl acetate and a dilute aqueous potassium carbonate solution. The organic phase was washed with water, dried (MgSO$_4$) and evaporated. The residue was purified by column chromatography using a 3:1 mixture of hexane and ethyl acetate as eluent. There was thus obtained the required starting material in 65% yield as a gum.

NMR Spectrum 1.5 (s, 3H), 1.6 (s, 3H), 2.5 (s, 3H), 3.9 (m, 2H), 5.3 (broad s, 1H), 7.2–7.8 (m, 8H).

EXAMPLE 89

Using an analogous procedure to that described in Example 68, 4'-[3-(2-ethyl-4-methyl-1,3-dioxolan-4-yl)phenylthio]acetophenone was reacted with hydroxylamine hydrochloride to give 4'-[3-(2-ethyl-4-methyl-1,3-dioxolan-4-yl)phenylthio]acetophenone oxime in 31% yield as a gum.

NMR Spectrum 1.5 (t, 3H), 1.6 (m, 2H), 2.2 (s, 3H), 3.8–4.1 (m, 2H), 5.05 (m, 1H), 7.2–7.6 (m, 8H), 8.1 (broad s, 1H).

The 4'-[3-(2-ethyl-4-methyl-1,3-dioxolan-4-yl)phenylthio]acetophenone used as a starting material was obtained as follows:

The procedure described in the portion of Example 88 which is concerned with the preparation of starting materials was repeated except that propanol was used in place of acetaldehyde. There was thus obtained the required starting material in 50% yield as a gum.

EXAMPLE 90

Using an analogous procedure to that described in Example 2, (E)-4'-[3-(4-methoxytetrahydropyran-4-yl)phenylsulphonyl]acetophenone oxime was reacted with bromoacetonitrile to give (E)-4'-[3-(4-methoxytetrahydropyran-4-yl)phenylsulphonyl]acetophenone oxime O-cyanomethyl ether in 73% yield, m.p. 124°–125° C.;

NMR Spectrum 1.87–2.06 (m, 4H), 2.27 (s, 3H), 2.95 (s, 3H), 3.82–3.90 (m, 4H), 4.84 (s, 2H), 7.46–7.64 (m, 2H), 7.75–8.0 (m, 6H).

EXAMPLE 91

Using an analogous procedure to that described in Example 2, (E)-4'-[5-fluoro-3-(4-methoxytetrahydropyran-4-yl)phenylthio]-α-tert-butyldimethylsilyloxyacetophenone oxime was reacted with bromoacetonitrile to give (E)-4'-[5-fluoro-3-(4-methoxytetrahydropyran-4-yl)phenylthio]-α-tert-butyldimethylsilyloxyacetophenone oxime O-cyanomethyl ether in 89% yield as an oil.

Tetrabutylammonium fluoride (1M in THF, 1.6 ml) was added to a mixture of the product so obtained (0.58 g) and THF (25 ml). The mixture was stirred at ambient temperature for 2 hours. The mixture was partitioned between ethyl acetate and water. The organic phase was washed with brine, dried (MgSO$_4$) and evaporated. The residue was purified by column chromatography using a 3:2 mixture of petroleum ether and ethyl acetate as eluent. There was thus obtained (E)-4'-[5-fluoro-3-(4-methoxytetrahydropyran-4-yl)phenylthio]-α-hydroxyacetophenone oxime O-cyanomethyl ether (0.32 g, 70%) as oil.

NMR Spectrum 1.82–2.02 (m, 4H), 2.99 (s, 3H), 3.75–3.85 (m, 4H), 4.74 (m, 2H), 4.86 (s, 2H), 6.92–7.04 (m, 2H), 7.20 (m, 1H), 7.38 (m, 2H), 7.65 (m, 2H).

The (E)-4'-[5-fluoro-3-(4-methoxytetrahydropyran-4-yl)phenylthio]-α-tert-butyldimethylsilyloxyacetophenone oxime used as a starting material was obtained as follows:

Imidazole (0.7 g) was added to a stirred mixture of 4'-[5-fluoro-3-(4-methoxytetrahydropyran-4-yl)phenylthio]-α-hydroxyacetophenone (1.3 g), tert-butyldimethylsilyl chloride (1.04 g) and THF (20 ml). The mixture was stirred at ambient temperature for 16 hours. The mixture was partitioned between ethyl acetate and water. The organic phase was washed with brine, dried (MgSO$_4$) and evaporated. The residue was purified by column chromatography using a 19:1 mixture of petroleum ether and ethyl acetate as eluent. There was thus obtained 4'-[5-fluoro-3-(4-methoxytetrahydropyran-4-yl)phenylthio]-α-tert-butyldimethylsilyloxyacetophenone (1.6 g, 96%) as an oil.

Using an analogous procedure to that described in Example 15, the product so obtained was reacted with hydroxylamine hydrochloride to give (E)-4'-[5-fluoro-3-(4-methoxytetrahydropyran-4-yl)phenylthio]-α-tert-butyldimethylsilyloxyacetophenone oxime in 85% yield, m.p. 120°–121° C.

EXAMPLE 92

Using an analogous procedure to that described in Example 2, the appropriate (E)-oxime was reacted with the appropriate alkylating agent to product the (E)-oxime derivatives described in the following table, in which the appropriately substituted phenylthio group is attached to the 2-position of the thiazole or thiophene ring.

TABLE 1

| Example 92 Compd. No. | $R^5$ | $Ar^2$ | Yield (%) | m.p. (°C.) |
|---|---|---|---|---|
| 1[a] | cyanomethyl | 2,5-thiazolediyl | 98 | 66–68 |
| 2[b] | 2-propynyl | 2,5-thiazolediyl | 77 | oil |
| 3[c] | 2-hydroxyethyl | 2,4-thiophenediyl | 57 | oil |
| 4[d] | 2-propynyl | 2,4-thiophenediyl | 74 | oil |
| 5[e] | cyanomethyl | 2,4-thiazolediyl | 98 | 137–139 |
| 6[f] | 2-propynyl | 2,4-thiazolediyl | 79 | 107–109 |

Notes:
[a]Bromoacetonitrile was used as the alkylating agent. The product gave the following NMR data: 1.95–2.05(m, 4H), 2.28(s, 3H), 3.06(s, 3H), 3.68–3.82(m, 4H), 4.84(s, 2H), 7.51(s, 1H), 7.62(d, 2H), 7.72(d, 2H).
[b]Propargyl bromide was used as the alkylating agent. The product gave the following NMR data: 1.92–2.06(m, 4H), 2.27(s, 3H), 2.49(m, 1H), 3.05(s, 3H), 3.67–3.83(m, 4H), 4.81(s, 2H), 7.48(s, 1H), 7.51(d, 2H), 7.72(d, 2H).
[c]2-(Tetrahydropyran-2-yloxy)ethyl bromide was used as the alkylating agent. The initial product was treated with acid to cleave the tetrahydropyranyloxy protecting group using the following procedure:-
A mixture of the oxime O-2-(tetrahydropyran-2-yloxy)ethyl ether (0.247 g), 2N aqueous hydrochloric acid (6 drops) and acetone (3 ml) was stirred at ambient temperature for 2.5 hours. The mixture was partitioned between diethyl ether and water. The organic phase was washed with brine, dried (MgSO$_4$) and evaporated. The residue was purified by column chromatography using a 1:3 mixture of petroleum ether and diethyl ether as eluent. There was thus obtained the required product as an oil (0.169 g, 82%).
NMR Spectrum 1.95–2.05(m, 4H), 2.22(s, 3H), 2.49(m, 1H), 3.04(s, 3H), 3.73–3.94(m, 6H), 4.29(m, 2H), 7.16(m, 2H), 7.28(d, 2H), 7.50(d, 2H).
[d]Propargyl bromide was used as the alkylating agent. The product gave the following NMR data: 1.95–2.04(m, 4H), 2.21(s, 3H), 2.48(s, 1H), 3.04(s, 3H), 3.72–3.86(m, 4H), 4.76(d, 2H), 7.16(d, 2H), 7.27(m, 2H), 7.56(d, 2H).
[e]Bromoacetonitrile was used as the alkylating agent. The product gave the following NMR data: 2.02–2.20(s, 4H), 2.27(s, 3H), 3.10(s, 3H), 3.70–3.90(m, 4H), 4.85(s, 2H), 7.10(s, 1H), 7.60(d, 2H), 7.71(d, 2H).
[f]Propargyl bromide was used as the alkylating agent. The product gave the following NMR data: 2.0–2.20(m, 4H), 2.24(s, 3H), 2.49(s, 1H), 3.09(s, 3H), 3.66–3.87(m, 4H), 4.80(d, 2H), TABLE 1-continued 7.07(s, 1H), 7.60(d, 2H), 7.72(d, 2H).

EXAMPLE 93

Using a similar procedure to that described in Example 2 except that the reaction mixture was heated to 60° C. for 6 hours, the appropriate (E)-oxime was reacted with the appropriate alkylating agent to product the (E)-oxime derivatives described in the following table, in which the appropriately substituted phenylthio group is attached to the 2-position of the thiophene or thiazole ring.

TABLE II

| Example 93 Compd. No. | $R^5$ | $Ar^2$ | Yield (%) | m.p. (°C.) |
|---|---|---|---|---|
| 1[a] | benzyl | 2,4-thiophenediyl | 46 | 88–89 |
| 2[b] | acetonyl | 2,4-thiophenediyl | 35 | oil |
| 3[c] | 4-methoxycarbonylbenzyl | 2,4-thiophenediyl | 59 | oil |
| 4[d] | 3-pyridylmethyl | 2,4-thiazolediyl | 30 | 120–121 |
| 5[e] | 4-pyridylmethyl | 2,4-thiazolediyl | 76 | 112–114 |

Notes:
[a]Benzyl bromide was used as the alkylating agent. The product gave the following NMR data: 1.95–2.02(m, 4H), 2.22(s, 3H), 3.04(s, 3H), 3.73–3.85(m, 4H), 5.21(s, 2H), 7.16(d, 2H), 7.23–7.42(m, 7H), 7.56(d, 2H).
[b]1-Iodopropan-2-one, used as the alkylating agent, was obtained by heating a mixture of 1-chloropropan-2-one, potassium iodide and ethanol to reflux for 1 hour. The oxime product gave the following NMR data: 1.94–2.04(m, 4H), 2.20(s, 3H), 2.28(s, 3H), 3.04(s, 3H), 3.75–3.85(m, 4H), 4.65(s, 2H), 7.15(d, 2H), 7.27(m, 2H), 7.53(d, 2H).
[c]4-Methoxycarbonylbenzyl bromide was used as the alkylating agent. The product gave the following NMR data: 1.95–2.05(m, 4H), 2.24(s, 3H), 3.04(s, 3H), 3.70–3.85(m, 4H), 3.91(s, 3H), 5.26(s, 2H), 7.14(d, 2H), 7.26(m, 2H), 7.44(d, 2H), 7.52(m, 2H), 8.01(d, 2H).
[d]A mixture of 3-chloromethylpyridine and sodium iodide was used as the alkylating agent. The product gave the following NMR data: 2.0–2.20(m, 4H), 2.26(s, 3H), 3.09(s, 3H), 3.68–3.88(m, 4H), 5.25(s, 2H), 7.06(s, 1H), 7.31(m, 1H), 7.58(d, 2H), 7.67(d, 2H), 7.74(m, 1H), 8.57(m, 1H), 8.68(m, 1H).
[e]A mixture of 4-chloromethylpyridine and sodium iodide was used as the alkylating agent. The product gave the following NMR data: 1.98–2.20(m, 4H), 2.32(s, 3H), 3.03(s, 3H), 3.66–3.88(m, 4H), 5.26(s, 2H), 7.06(s, 1H), 7.28(d, 2H), 7.58(d, 2H), 7.66(d, 2H), 8.60(m, 2H).

EXAMPLE 94

Using an analogous procedure to that described in Example 44, (E)-4'-[2-amino-6-(4-methoxytetrahydropyran-4-yl)pyrimidin-4-ylthio]acetophenone oxime was reacted with methyl iodide to give (E)-4'-[2-amino-6-(4-methoxytetrahydropyran-4-yl)pyrimidin-4-ylthio]acetophenone oxime O-methyl ether in 54% yield as an oil.

NMR Spectrum 1.5–1.65 (m, 2H), 1.9–2.05 (m, 2H), 2.18 (s, 3H), 2.93 (s, 3H), 3.55–3.70 (m, 4H), 4.9 (s, 3H), 6.27 (s, 1H), 7.50 (d, 2H), 7.66 (d, 2H).

EXAMPLE 95 n-Butyl-lithium (1.6M in hexane, 6.77 ml) was added dropwise to stirred solution of di-isopropylamine (1.52 ml) in THF (25 ml) which had been cooled to −70° C. The mixture was allowed to warm to −33° C. during 1 hour. The mixture was recooled to −70° C. and a solution of 4-methoxy-4-(3-thienyl)tetrahydropyran (1.43 g) in THF (5 ml) was added dropwise. The mixture was allowed to warm to −14° C. and stirred for 3 hours. The mixture was recooled to −70° C. and a solution of di-[(E)-1-tert-butyldimethylsilyloxyiminoindan-5-yl]disulphide (4 g) in THF (20 ml) was added. The mixture was allowed to warm to −25° C. during 2 hours. The mixture was poured into a cold aqueous ammonium chloride solution and extracted with ethyl acetate. The organic phase was washed with brine, dried (MgSO$_4$) and evaporated. The residue was purified by column chromatography using a 19:1 mixture of methylene chloride and diethyl ether as eluent. There was thus obtained (E)-5-[4-(4-methoxytetrahydropyran-4-yl)thien-2-ylthio]indan-1-one oxime O-tert-butyldimethylsilyl ether (2.82 g, 84%).

Tetrabutylammonium fluoride (1M in THF, 1.75 ml) was added dropwise to a stirred mixture of a portion (0.57 g) of the product so obtained in THF (10 ml) which had been cooled to 0° C. The mixture was stirred at to 0° C. for 1 hour. The mixture was partitioned between ethyl acetate and water. The organic phase was washed with water, dried (MgSO$_4$) and evaporated. The residue was purified by column chromatography using a 2:1 mixture of petroleum ether and ethyl acetate as eluent. There was thus obtained (E)-5-[4-(4 -methoxytetrahydropyran-4-yl)thien-2-ylthio] indan-2-one oxime (0.392 g, 90%), m.p. 137°–138° C.;

NMR Spectrum (CD$_3$SOCD$_3$) 1.88–2.02 (m, 4H), 2.68–2.78 (m, 2H), 2.90–2.98 (m, 5H), 3.58–3.70 (m, 4H), 7.06 (d, 1H), 7.13 (s, 1H), 7.41 (s, 1H), 7.49 (d, 1H), 7.71 (s, 1H).

The di-[(E)-1-tert-butyldtmethylstlyloxyiminoindan-5-yl disulphide used as a starting material was obtained as follows:

A solution of sodium hydrosulfide hydrate (31 g) in NMP (600 ml) was stirred and heated to 140° C. Approximately 150 ml of the mixture was evaporated under vacuum to remove the water. A solution of 5-bromoindan-1-one (38 g) in NMP (150 ml) was added to the hot (130° C.) reaction mixture and the mixture was stirred at 130° C. for 15 minutes. The mixture was cooled to ambient temperature. Ethyl acetate was added and the mixture was acidified to pH2 by the addition of 6N aqueous hydrochloric acid. The solution was washed with water, dried (MgSO$_4$) and evaporated. A solution of the product so obtained in DMSO (150 ml) was stirred at ambient temperature for 48 hours. The mixture was partitioned between ethyl acetate and water. The organic phase was washed with water, dried (MgSO$_4$) and evaporated. The residue was purified by column chromatography using a 5:2 mixture of petroleum ether and ethyl acetate as eluent. There was thus obtained di-(1-oxoindan-5-yl) disulphide (24.3 g, 41%).

A mixture of a portion (3 g) of the material so obtained, hydroxylamine hydrochloride (1.92 g) and pyridine (20 ml) was stirred and heated to 50° C. for 3 hours. The mixture was then stirred at ambient temperature for 16 hours. The mixture was filtered and the precipitate so isolated was washed with water and ethyl acetate and dried. There was thus obtained di-[(E)-1-hydroxyiminoindan-5-yl]disulphide (2.79 g, 85%).

After repetition of the preceding step, a mixture of the material so obtained (3.39 g), tert-butyldimethylsilyl chloride (3.16 g), imidazole (2.59 g) and DMF (26 ml) was stirred at ambient temperature for 24 hours. The mixture was partitioned between ethyl acetate and water. The organic phase was washed with water, dried (MgSO$_4$) and evaporated. The residue was purified by column chromatography using a 40:1 mixture of petroleum ether and diethyl ether as eluent. There was thus obtained di-[(E)-1-tert-butyldimethylsilyloxyiminoindan-5-yl]disulphide (4 g, 72%).

EXAMPLE 96

Using an analogous procedure to that described in Example 3, (E)-5-[4-(4-methoxytetrahydropyran-4-yl)thien-2-ylthio]indan-1-one oxime was reacted with bromoacetonitrile to give (E)-5-[4-(4-methoxytetrahydropyran-4-yl)thien-2-ylthio]indan-1-one oxime O-cyanomethyl ether in 72% yield, m.p. 109°–110° C.;

NMR Spectrum 1.96–2.06 (m, 4H), 2.82–3.0 (m, 4H), 3.04 (s, 3H), 3.72–3.88 (m, 4H), 4.78 (s, 2H), 7.04–7.10 (m, 2H), 7.24–7.31 (m, 2H), 7.57 (d, 1H).

EXAMPLE 97

Using an analogous procedure to that described in Example 2, (E)-7-[4-(4-methoxytetrahydropyran-4-yl)thien-2-ylthio]chroman-4-one oxime was reacted with bromoacetonitrile to give (E)-7-[4-(4-methoxytetrahydropyran-4-yl)thien-2-ylthio]chroman-4-one oxime O-cyanomethyl ether in 66% yield, m.p. 120°–121° C.;

NMR Spectrum 1.94–2.04 (m, 4H), 2.88 (t, 2H), 3.06 (s, 3H), 3.72–3.88 (m, 4H), 4.19 (t, 2H), 4.79 (s, 2H), 6.62 (s, 1H), 6.72 (m, 1H), 7.22–7.31 (m, 2H), 7.78 (d, 1H).

EXAMPLE 98

Using an analogous procedure to that described in Example 53, (E)-7-[4-(4-methoxytetrahydropyran-4-yl)thien-2-ylthio]chroman-4-one oxime was reacted with 3-chloromethylpyridine to give (E)-7-[4-(4-methoxytetrahydropyran-4-yl)thien-2-ylthio]chroman-4-one oxime O-(3-pyridyl)methyl ether in 56% yield as an oil.

NMR Spectrum 1.96–2.03 (m, 4H), 2.88 (t, 2H), 3.04 (s, 3H), 3.70–3.86 (m, 4H), 4.17 (t, 2H), 5.19 (s, 2H), 6.62 (s, 1H), 6.70 (m, 1H), 7.20–7.30 (m, 3H), 7.67–7.74 (m, 2H), 8.55 (d, 1H), 8.63 (s, 1H).

EXAMPLE 99

Using an analogous procedure to that described in Example 53, (E)-7-[4-(4-methoxytetrahydropyran-4-yl)thien-2-ylthio] chroman-4-one oxime was reacted with 4-chloromethylpyridine to give (E)-7-[4-(4-methoxytetrahydropyran-4-yl)thien-2-ylthio]chroman-4-one oxime O-(4-pyridyl)methyl ether in 69% yield as an oil.

NMR Spectrum 1.92–2.02 (m, 4H), 2.93 (t, 2H), 3.02 (s, 3H), 3.72–3.87 (m, 4H), 4.19 (t, 2H), 5.19 (s, 2H), 6.62 (s, 1H), 6.70 (m, 1H), 7.21–7.31 (m, 4H), 7.70 (d, 1H), 8.57 (m, 1H).

EXAMPLE 100

Using analogous procedures to those described in Example 95, di-[(E)-5-(1-tert-butyldimethylsilyloxyiminoethyl)pyrid-2-yl]disulphide was reacted with 4-methoxy-4-(3-thienyl)tetrahydropyran and the resultant product was treated with tetrabutylammonium fluoride to give (E)-6-[4-(4-methoxytetrahydropyran-4-yl)thien-2-ylthio]pyrid-3-yl methyl ketone oxime in 75% yield, m.p. 151°–153° C.;

NMR Spectrum (CD$_3$SOCD$_3$) 1.90–2.02 (m, 4H), 2.50 (m, 3H), 2.96 (s, 3H), 3.55–3.70 (m, 4H), 6.92 (d, 1H), 7.46 (d, 1H), 7.80 (d, 1H), 7.93 (d, 1H), 8.66 (m, 1H).

The di-[(E)-5-(1-tert-butyldimethylsilyloxyiminoethyl)pyrid-2-yl]disulphide used as a starting material was obtained as follows:

Using analogous procedures to those described in the second and third paragraphs of the portion of Example 63 which is concerned with the preparation of starting materials, 2,5-dibromopyridine was converted into 6-bromopyrid-3-yl methyl ketone in 62% yield.

A solution of sodium hydrosulfide hydrate (5.26 g) in NMP (50 ml) was stirred and heated to 140° C. The mixture was partially evaporated under vacuum to remove the water. A solution of 6-bromopyrid-3-yl methyl ketone (6.26 g) in NMP (20 ml) was added and the mixture was heated to 80° C. for 1 hour. The mixture was cooled to ambient temperature and partitioned between ethyl acetate and water. The organic phase was washed with brine, dried (MgSO$_4$) and evaporated. There was thus obtained 6-mercaptopyrid-3-yl methyl ketone (3.57 g, 75%).

A dilute (0.1N) solution of sodium hydroxide (10.5 ml) was added to a mixture of the product so obtained, iodine (3.14 g) and ethanol (63 ml). The mixture was stirred at ambient temperature for 0.75 hours. The mixture was evaporated and the residue was partitioned between methylene chloride and water. The organic phase was washed with an aqueous sodium thiosulphate solution and with brine, dried (MgSO$_4$) and evaporated. The residue was purified by column chromatography using a 19:1 mixture of methylene chloride and diethyl ether as eluent. There was thus obtained di-[5-acetylpyrid-2-yl]disulphide (3.29 g, 95%), m.p. 149°–150° C.

Using an analogous procedure to that described in Example 14, except that the reaction mixture was heated to 80° C. for 8 hours, the product so obtained was reacted with hydroxylamine hydrochloride to give di-[(E)-5-(1-hydroxyiminoethyl)pyrid-2-yl]disulphide in 79% yield, m.p. 200°–201° C.

Using an analogous procedure to that described in the last paragraph of the portion of Example 95 which is concerned with the preparation of starting materials, the product so obtained was reacted with tert-butyldimethylsilyl chloride to give di-[(E)-5-(1-tert-butyldimethylsilyloxyiminoethyl)pyrid-2-yl]disulphide in 95% yield as an oil.

EXAMPLE 101

Using an analogous procedure to that described in Example 2, (E)-6-[4-(4-methoxytetrahydropyran-4-yl)thien-2-ylthio]pyrid-3-yl methyl ketone oxime was reacted with bromoacetonitrile to give (E)-6-[4-(4-methoxytetrahydropyran-4-yl)thien-2-ylthio]pyrid-3-yl methyl ketone oxime O-cyanomethyl ether in 40% yield, m.p. 97°–98° C.;

NMR Spectrum 1.97–2.05 (m, 4H), 2.24 (s, 3H), 3.06 (s, 3H), 3.75–3.88 (m, 4H), 4.82 (s, 2H), 6.89 (m, 1H), 7.36 (m, 2H), 7.85 (m, 1H), 8.65 (m, 1H).

EXAMPLE 102

Using an analogous procedure to that described in Example 2, (E)-6-[4-(4-methoxytetrahydropyran-4-yl)thien-2-ylthio]pyrid-3-yl methyl ketone oxime was reacted with propargyl bromide to give (E)-6-[4-(4-methoxytetrahydropyran-4-yl)thien-2-ylthio]pyrid-3-yl methyl ketone oxime O-(2-propynyl) ether in 55% yield, m.p. 80°–81° C.;

NMR Spectrum 1.97–2.08 (m, 4H), 2.23 (s, 3H), 2.46 (m, 1H), 3.05 (s, 3H), 3.72–3.88 (m, 4H), 4.77 (s, 2H), 6.87 (m, 1H), 7.35 (m, 2H), 7.83 (m, 1H), 8.64 (m, 1H).

EXAMPLE 103

Using an analogous procedure to that described in Example 2, (E)-4'-{5-fluoro-3-[(2S,4R)-4-methoxy-2-methyltetrahydropyran-4-yl]phenylthio}acetophenone oxime was reacted with bromoacetonitrile to give (E)-4'-{5-fluoro-3-[(2S,4R)-4-methoxy-2-methyltetrahydropyran-4-yl]phenylthio}acetophenone oxime O-cyanomethyl ether in 85% yield as an oil.

NMR Spectrum 1.20 (d, 3H), 1.52 (m, 1H), 1.83–1.97 (m, 3H), 2.26 (s, 3H), 2.99 (s, 3H), 3.80–3.92 (m, 3H), 4.83 (s, 2H), 6.90 (d, 1H), 6.98 (d, 1H), 7.18 (s, 1H), 7.35 (d, 2H), 7.64 (d, 2H).

EXAMPLE ψ

Using an analogous procedure to that described in Example 2, (E)-4'-{5-fluoro-3-[(2S,4R)-4-methoxy-2-methyltetrahydropyran-4-yl]phenylsulphonyl}acetophenone oxime was reacted with bromoacetonitrile to give (E)-4'-{5-fluoro-3-[{2S,4R)-4-methoxy-2-methyltetrahydropyran-4-yl]phenylsulphonyl}acetophenone oxime O-cyanomethyl ether in 71% yield, m.p. 170°–171° C.;

NMR Spectrum 1.20 (d, 3H), 1.53 (m, 1H), 1.85–1.97 (m, 3H), 2.28 (s, 3H), 3.0 (s, 3H), 3.80–3.93 (m, 3H), 4.85 (s, 2H), 7.32 (m, 1H), 7.54 (m, 1H), 7.77 (s, 1H), 7.83 (m, 2H), 7.96 (m, 2H).

EXAMPLE 105

Using an analogous procedure to that described in Example 11, 4'-{5-fluoro-3-[(2RS,3SR)-3-methoxy-2-methyltetrahydrofuran-3-yl]phenylthio}propiophenone oxime was reacted with methyl iodide to give 4'-{5-fluoro-3-[(2RS,3SR)-3-methoxy-2-methyltetrahydrofuran-3-yl]phenylthio}proptophenone oxime O-methyl ether in 60% yield as a gum.

NMR Spectrum (CD$_3$SOCD$_3$) 1.0 (m, 6H), 2.4 (m, 2H), 2.8 (q, 2H), 3.2 (s, 3H), 3.7 (q, 1H), 4.0 (m, 5H), 6.8–7.6 (m, 7H).

EXAMPLE 106

Using an analogous procedure to that described in Example 11, the appropriate (E)-oxime was reacted with the appropriate alkylating agent to produce the (E)-oxime derivatives described in the following table. In each case the relative stereochemistry in the tetrahydrofuran ring has the methoxy and methyl groups in a cis-relationship.

TABLE III

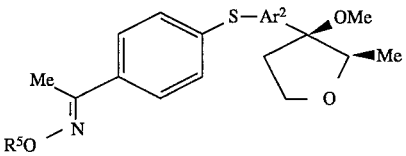

| Example 106 Compd. No. | R$^5$ | Ar$^2$ | Yield (%) | m.p. (°C.) |
|---|---|---|---|---|
| 1$^a$ | cyanomethyl | 5-fluoro-1,3-phenylene | 87 | gum |

TABLE III-continued

| | | | | |
|---|---|---|---|---|
| 2[b] | methyl | 5-fluoro-1,3-phenylene | 81 | gum |
| 3[c] | 4-pyridylmethyl | 5-fluoro-1,3-phenylene | 35 | gum |
| 4[d] | cyanomethyl | 2,4-thiophenediyl | 84 | gum |
| 5[e] | methyl | 2,4-thiophenediyl | 87 | gum |

Notes

[a]Bromoacetonitrile was used as the alkylating agent. The product gave the following NMR data: ($CD_3SOCD_3$) 1.0(d, 3H), 2.2(s, 3H), 2.5(m, 2H), 3.1(s, 3H), 3.6(q, 1H), 3.9(m, 2H), 5.1(s, 2H), 7.0–7.8(m, 7H).

[b]Methyl iodide was used as the alkylating agent. The product gave the following NMR data: ($CD_3SOCD_3$) 1.0(d, 3H), 2.2(s, 3H), 2.5(m, 2H), 3.1(s, 3H), 3.6(q, 1H), 3.9(m, 2H), 3.95(s, 3H), 7.0–7.7 (m, 7H).

[c]4-Chloromethylpyridine was used as the alkylating agent. The product gave the following NMR data: ($CD_3SOCD_3$) 1.0(d, 3H), 2.25(s, 3H), 2.4(m, 2H), 3.1(s, 3H), 3.6(q, 1H), 3.9(m, 2H), 5.3(s, 2H), 7.0–7.7(s, 9H), 8.6(d, 2H).

[d]The substituted phenylthio group is attached to the 2-position of the thiophene ring. Bromoacetonitrile was used as the alkylating agent. The product gave the following NMR data: 1.3(d, 3H), 2.2(s, 3H), 2.5(m, 2H), 3.2(s, 3H), 3.8(q, 1H), 4.0(m, 2H), 4.8(s, 2H), 7.1–7.6(m, 6H).

[e]The substituted phenylthio group is attached to the 2-position of the thiophene ring. Methyl iodide was used as the alkylating agent. The product gave the following NMR data: 1.2(d, 3H), 2.2(s, 3H), 2.5(m, 2H), 3.2(s, 3H), 3.8(q, 1H), 4.0(m, 5H), 7.1–7.6(m, 6H).

EXAMPLE 107

Using an analogous procedure to that described in Example 11, 4'-{5-fluoro-3-[(2RS,3SR)-3-methoxy-2-methyltetrahydrofuran-3-yl]phenoxy}propiophenone oxime was reacted with methyl iodide to give 4'-{5-fluoro-3-[(2RS,3SR)-3-methoxy-2-methyltetrahydrofuran-3-yl]phenoxy}propiophenone oxime O-methyl ether in 73% yield as a gum.

NMR Spectrum ($CD_3SOCD_3$) 1.0 (m, 6H), 2.5 (m, 2H), 2.7 (q, 2H), 3.1 (s, 3H), 3.6 (q, 1H), 3.9 (m, 5H), 6.8–7.7 (m, 7H).

EXAMPLE 108

Using an analogous procedure to that described in Example 2, the appropriate indanone (E)-oxime was reacted with the appropriate alkylating agent to product the (E)-oxime derivatives described in the following table. In each case the relative stereochemistry in the tetrahydrofuran ring has the methoxy and methyl groups in a cis-relationship.

TABLE IV

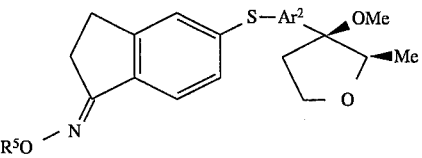

| Example 108 Compd. No. | R[5] | Ar[2] | Yield (%) | m.p. (°C.) |
|---|---|---|---|---|
| 1[a] | methyl | 5-fluoro-1,3-phenylene | 87 | gum |
| 2[b] | cyanomethyl | 5-fluoro-1,3-phenylene | 34 | gum |
| 3[c] | 3-pyridylmethyl | 5-fluoro-1,3-phenylene | 68 | gum |
| 4[d] | cyanomethyl | 2,4-thiophenediyl | 68 | gum |

Notes

[a]Methyl iodide was used as the alkylating agent. The product gave the following NMR data: 1.1(d, 3H), 2.4(m, 2H), 2.9(m, 4H), 3.2(s, 3H), 3.7(q, 1H), 4.0(m, 5H), 6.8–7.7(m, 6H).

[b]Bromoacetonitrile was used as the alkylating agent. The product gave the following NMR data: 1.1(d, 3H), 2.4(m, 2H), 3.0(m, 4H), 3.2(s, 3H), 3.7(q, 1H), 4.0(m, 2H), 4.8(s, 2H), 6.9–7.7(m, 6H).

[c]3-Chloromethylpyridine was used as the alkylating agent. The product gave the following NMR data: 1.1(d, 3H), 2.4(m, 2H), 3.0(m, 4H), 3.2(s, 3H), 3.7(q, 1H), 4.0(m, 2H), 5.2(s, 2H), 6.8–7.8(m, 8H), 8.5–8.7(m, 2H).

[d]Bromoacetonitrile was used as the alkylating agent. The substituted phenylthio group is attached to the 2-position of the thiophene ring. The product gave the following NMR data: ($CD_3SOCD_3$) 1.1(d, 3H), 2.5(m, 2H), 2.8–3.0(m, 4H), 3.1(s, 3H), 3.7(q, 1H), 3.9(m, 2H), 5.0(s, 2H), 7.1–7.8(m, 5H).

EXAMPLE 109

Using an analogous procedure to that described in Example 11, (E)-7-{5-fluoro-3-[4-(2RS,3SR)-3-methoxy-2-methyltetrahydrofuran-3-yl]phenylthio}chroman-4-one oxime was reacted with bromoacetonitrile to give (E)-7-{5-fluoro-3-[4-(2RS,3SR)-3-methoxy-2-methyltetrahydrofuran-3-yl]phenylthio}chroman-4-one oxime O-cyanomethyl ether in 54% yield as a gum.

NMR Spectrum 1.2 (d, 3H), 2.5 (m, 2H), 2.9 (t, 2H), 3.2 (s, 2H), 3.7 (q, 1H), 4.0 (m, 2H), 4.2 (t, 2H), 4.8 (s, 2H), 6.8–7.8 (m, 6H).

EXAMPLE 110

Sodium hydride (60%, 0.5 g) was added to a stirred solution of (E)-4'-[4-(2,2,4-trimethyl-1,3-dioxolan-4-yl)thien-2-ylthio]acetophenone oxime (0.23 g) in DMF (2 ml) which had been cooled to 0° C. The mixture was allowed to warm to ambient temperature and was stirred for 1 hour. The mixture was recooled to 0° C. and a solution of bromoacetonitrile (0.15 g) in DMF (1 ml) was added. The mixture was stirred at 0° C. for 3 hours and then partitioned between ethyl acetate and a cold dilute aqueous citric acid solution. The organic phase was washed with a saturated aqueous sodium bicarbonate solution and with brine, dried ($MgSO_4$) and evaporated. The residue was purified by column chromatography using a 19:1 mixture of toluene and ethyl acetate as eluent. There was thus obtained (E)-4'-[4-(2,2,4-trimethyl-1,3-dioxolan-4-yl)thien-2-ylthio]acetophenone oxime O-cyanomethyl ether (0.237 g, 93%) as an oil.

NMR Spectrum 1.33 (s, 3H), 1.4 (s, 3H), 1.55 (s, 3H), 2.2 (s, 3H), 3.95–4.08 (q, 2H), 5.05 (s, 2H), 7.15–7.25 (m, 2H), 7.4 (d, 1H), 7.6–7.7 (m, 3H).

EXAMPLE 111

Using an analogous procedure to that described in Example 44, (E)-4'-[3-(2,2,4-trimethyl-1,3-dioxolan-4-yl)phenylthio]acetophenone oxime was reacted with bromoacetonitrile to give (E)-4'-[3-(2,2,4-trimethyl-1,3-dioxolan-4-yl)phenylthio]acetophenone oxime O-cyanomethyl ether in 68% yield as a gum.

NMR Spectrum 1.3 (s, 3H), 1.5 (s, 6H), 2.2 (s, 3H), 4.0 (m, 2H), 4.8 (s, 2H), 7.2–7.6 (m, 8H).

EXAMPLE 112

Using an analogous procedure to that described in Example 31, (E)-4'-[3-(4-methoxytetrahydropyran-4-yl)phenylthio]acetophenone oxime was reacted with acetyl chloride to give O-acetyl-(E)-4'-[3-(4-methoxytetrahydropyran-4-yl)phenylthio]acetophenone oxime in 69% yield as an oil.

NMR Spectrum 1.86–2.04 (m, 4H), 2.26 (s, 3H), 2.36 (s, 3H), 2.97 (s, 3H), 3.75–3.88 (m, 4H), 7.23 (m, 2H), 7.28–7.36 (m, 3H), 7.47 (s, 1H), 7.66 (d, 2H).

EXAMPLE 113

Using an analogous procedure to that described in Example 31, (E)-4'-[3-(4-methoxytetrahydropyran-4-yl)phenylsulphonyl]acetophenone oxime was reacted with acetyl chloride to give O-acetyl-(E)-4'-[3-(4-methoxytetrahydropyran-4-yl)phenylsulphonyl]acetophenone oxime in 40% yield, m.p. 143°–145° C.;

NMR Spectrum 1.88–2.04 (m, 4H), 2.26 (s, 3H), 2.39 (s, 3H), 2.94 (s, 3H), 3.78–3.88 (m, 4H), 7.52 (m, 1H), 7.62 (m, 1H), 7.85 (m, 3H), 7.96 (m, 3H).

EXAMPLE 114

Using an analogous procedure to that described in Example 31 except that THF was used as a co-solvent, (E)-4'-[5-(4-methoxytetrahydropyran-4-yl)thiazol-2-ylthio] acetophenone oxime was reacted with pivaloyl chloride to give O-pivaloyl-(E)-4'-[5-(4-methoxytetrahydropyran-4-yl)thiazol-2-ylthio] acetophenone oxime in 92% yield as an oil.

NMR Spectrum 1.34 (s, 9H) 1.93–2.05 (m, 4H), 2.39 (s, 3H), 3.05 (s, 3H), 3.68–3.83 (m, 4H), 7.51 (s, 1H), 7.62 (d, 2H), 7.80 (d, 2H).

EXAMPLE 115

Sodium hydride (60%, 0.043 g) was added to a stirred solution of (E)-4'-[4-(4-methoxytetrahydropyran-4-yl)thien-2-ylthio]acetophenone oxime (0.29 g) in THF (2 ml) and the mixture was stirred at ambient temperature for 30 minutes. Acetyl chloride (0.064 ml) was added and the mixture was stirred at ambient temperature for 16 hours. The mixture was partitioned between diethyl ether and water. The organic phase was washed with brine, dried (MgSO$_4$) and evaporated. The residue was purified by column chromatography using a 7:3 mixture of petroleum ether and ethyl acetate as eluent. There was thus obtained O-acetyl-(E)-4'-[4-(4-methoxytetrahydropyran-4-yl)thien-2-ylthio]acetophenone oxime (0.202 g, 62%), m.p. 77°–78° C.;

NMR Spectrum 1.93–2.04 (m 4H), 2.25 (s, 3H), 2.33 (s, 3H), 3.03 (s, 3H), 3.62–3.88 (m, 4H), 7.15 (d, 2H), 7.25 (m, 2H), 7.63 (d, 2H).

EXAMPLE 116

Using an analogous procedure to that described in Example 115, (E)-4'-[4-(4-methoxytetrahydropyran-4-yl)thien-2-ylthio]acetophenone oxime was reacted with pivaloyl chloride to give O-pivaloyl-(E)-4'-[4-(4-methoxytetrahydropyran-4-yl)thien-2-ylthio]acetophenone oxime in 70% yield, m.p. 109°–110° C.;

NMR Spectrum 1.34 (s, 9H), 1.94–2.05 (m, 4H), 2.34 (s, 3H), 3.05 (s, 3H), 3.71–3.89 (m, 4H), 7.16 (d, 2H), 7.26 (m, 2H), 7.66 (d, 2H).

EXAMPLE 117

Using an analogous procedure to that described in Example 31, (E)-4'-[4-(4-methoxytetrahydropyran-4-yl)thiazol-2-ylthio]acetophenone oxime was reacted with acetyl chloride to give O-acetyl-(E)-4'-[4-(4-methoxytetrahydropyran-4-yl)thiazol-2-ylthio]acetophenone oxime in 96% yield, m.p. 114°–116° C.;

NMR Spectrum 2.0–2.2 (m, 4H), 2.27 (s, 3H), 2.39 (s, 3H), 3.09 (s, 3H), 3.68–3.87 (m, 4H), 7.11 (s, 1H), 7.61 (d, 2H), 7.77 (d, 2H).

EXAMPLE 118

Using an analogous procedure to that described in Example 31, (E)-6-[4-(4-methoxytetrahydropyran-4-yl)thien-2-ylthio]pyrid-3-yl methyl ketone oxime was reacted with acetyl chloride to give O-acetyl-(E)-6-[4-(4-methoxytetrahydropyran-4-yl)thien-2-ylthio]pyrid-3-yl methyl ketone oxime in 62% yield, m.p. 115°–116° C.;

NMR Spectrum 1.96–2.04 (m, 4H), 2.26 (s, 3H), 2.37 (s, 3H), 3.05 (s, 3H), 3.74–3.88 (m, 4H), 6.90 (d, 1H), 7.37 (d, 2H), 7.95 (m, 1H), 8.70 (s, 1H).

EXAMPLE 119

Using an analogous procedure to that described in Example 115, (E)-6-[4-(4-methoxytetrahydropyran-4-yl)thien-2-ylthio]pyrid-3-ylmethyl ketone oxime was reacted with pivaloyl chloride to give O-pivaloyl-(E)-6-[4-(4-methoxytetrahydropyran-4-yl)thien-2-ylthio]pyrid-3-yl methyl ketone oxime in 52% yield, m.p. 113°–114° C.;

NMR Spectrum 1.33 (s, 9H), 1.96–2.04 (m, 4H), 2.36 (s, 3H), 3.05 (s, 3H), 3.72–2.89 (m, 4H), 6.90 (d, 1H), 7.35 (m, 2H), 7.98 (m, 1H), 8.71 (m, 1H).

EXAMPLE 120

Using an analogous procedure to that described in Example 31 except that 1,4-dioxan was used as a co-solvent, (E)-5-[5-fluoro-3-(4-methoxytetrahydropyran-4-yl)phenylthio]indan-1-one oxime was reacted with acetyl chloride to give O-acetyl-(E)-5-[5 -fluoro-3-(4-methoxytetrahydropyran-4-yl)phenylthio]indan-1-one oxime in 61% yield, m.p. 113°–114° C.;

NMR Spectrum 1.83–2.0 (m, 4H), 2.24 (s, 3H), 2.99 (s, 3H), 3.05 (m, 4H), 3.75–3.83 (m, 4H), 6.92–7.05 (m, 2H), 7.19–7.30 (m, 3H), 7.82 (m, 1H).

EXAMPLE 121

Using an analogous procedure to that described in Example 31 except that 1,4-dioxan was used as a co-solvent, (E)-5-[4-(4 -methoxytetrahydropyran-4-yl)thien-2-ylthio]indan-1-one oxime was reacted with pivaloyl chloride to give O-pivaloyl-(E)-5-[4-(4 -methoxytetrahydropyran-4-yl)thien-2-ylthio]indan-1-one oxime in 65% yield, m.p. 155°–156° C.;

NMR Spectrum 1.30 (s, 9H), 1.95–2.22 (m, 4H), 2.93–3.12 (m, 7H), 3.67–3.90 (m, 4H), 7.0–7.15 (m, 2H), 7.30 (m, 1H), 7.48 (m, 1H), 7.79 (m, 1H).

EXAMPLE 122

Using an analogous procedure to that described in Example 31, 7-[5-fluoro-3-(4-methoxytetrahydropyran-4-yl)phenylthio]chroman-4-one oxime was reacted with acetyl chloride to give O-acetyl-7-[5-fluoro-3-(4-methoxytetrahydropyran-4-yl)phenylthio]chroman-4-one oxime in 36% yield, m.p. 108°–109° C.;

NMR Spectrum 1.83–2.01 (m, 4H), 2.26 (s, 3H), 2.99 (s, 3H), 3.03 (t, 3H), 3.76–3.84 (m, 4H), 4.25 (t, 2H), 6.78 (s, 1H), 6.85 (m, 1H), 7.04 (m, 2H), 7.24 (m, 1H), 7.99 (d, 1H).

EXAMPLE 123

Using an analogous procedure to that described in Example 115, (E)-7-[4-(4-methoxytetrahydropyran-4-yl)thien-2-ylthio] chroman-4-one oxime was reacted with acetyl chloride to give O-acetyl-(E)-7-[4-(4-methoxytetrahydropyran-4-yl)thien-2-ylthio] chroman-4-one oxime in 75% yield, m.p. 150° C.;

NMR Spectrum 1.93–2.05 (m, 4H), 2.25 (s, 3H), 2.98 (t, 2H), 3.04 (s, 3H), 3.71–3.88 (m, 4H), 4.18 (t, 2H), 6.61 (s, 1H), 6.72 (m, 1H), 7.29 (m, 2H), 7.92 (d, 1H).

EXAMPLE 124

Using an analogous procedure to that described in Example 115, (E)-7-[4-(4-methoxytetrahydropyran-4-yl)thien-2-ylthio] -chroman-4-one oxime was reacted with pivaloyl chloride to give O-pivaloyl-(E)-7-[4-(4-methoxytetrahydropyran-4-yl)thien-2-ylthio]chroman-4-one oxime in 74% yield, m.p. 117°–118° C.;

NMR Spectrum 1.30 (s, 9H), 1.91–2.03 (m, 4H), 2.94 (t, 2H), 3.03 (s, 3H), 3.70–3.88 (m, 4H), 4.21 (t, 2H), 6.59 (s, 1H), 6.72 (m, 1H), 7.29 (m, 2H), 7.97 (d, 1H).

EXAMPLE 125

A mixture of (E)-4'-[3-(4-methoxytetrahydropyran-4-yl)phenylthio]acetophenone oxime (0.714 g), 3-chloroperoxybenzoic acid (50%, 2.07 g) and methylene chloride (10 ml) was stirred at ambient temperature for 6 hours. The mixture was partitioned between methylene chloride and rarer. The organic phase was washed with brine, dried (MgSO$_4$) and evaporated. The residue was purified by column chromatography using increasingly polar mixtures of petroleum ether and ethyl acetate as eluent. There was thus obtained (E)-4'-[3-(4-methoxytetrahydropyran-4-yl)phenylsulphonyl]acetophenone oxime (0.4 g, 52%), m.p. 139°–140° C.;

NMR Spectrum 1.88–2.04 (m, 4H), 2.27 (s, 3H), 2.94 (s, 3H), 3.77–3.88 (m, 4H), 7.51 (m, 1H), 7.61 (m, 1H), 7.72–7.96 (m, 6H).

EXAMPLE 126

A solution of potassium peroxymonosulphate (0.23 g) in water (2 ml) was added dropwise to a stirred solution of (E)-4'-[4-(4 -methoxytetrahydropyran-4-yl)thien-2-ylthio] acetophenone oxime (0.18 g) in methanol (2 ml) which had been cooled to 0° C. The acidity of the solution was adjusted to pH5 by the addition of a sodium acetate buffer. The mixture was allowed to warm to ambient temperature and was stirred for 4 hours. The mixture was evaporated and the residue was partitioned between ethyl acetate and water. The organic phase was washed with brine, dried (MgSO$_4$) and evaporated. The residue was purified by column chromatography using increasingly polar mixtures of petroleum ether and ethyl acetate as eluent. There was thus obtained (E)-4'-[4-(4-methoxytetrahydropyran-4-yl)thien-2-ylsulphinyl]acetophenone oxime (0.16 g, 81%), m.p. 120°–121° C.;

NMR Spectrum 1.88–2.0 (m, 4H), 2.28 (s, 3H), 2.99 (s, 3H), 3.70–3.88 (m, 4H), 7.38 (s, 1H), 7.59 (s, 1H), 7.70 (d, 2H), 7.78 (d, 2H), 8.0 (broad s, 1H).

EXAMPLE 127

Using an analogous procedure to that described in Example 125, (E)-4'-{5-fluoro-3-[(2S,4R)-4-methoxy-2-methyltetrahydropyran-4-yl]phenylthio}acetophenone oxime was oxidized to give (E)-4'-{5 -fluoro-3-[(2S,4R)-4-methoxy-2-methyltetrahydropyran-4-yl]phenylsulphonyl}acetophenone oxime in 75% yield, m.p. 149° C.;

NMR Spectrum 1.20 (d, 3H), 1.55 (m, 1H), 1.82–1.97 (m, 3H), 2.27 (s, 3H), 2.94 (s, 3H), 3.8–3.94 (m, 3H), 7.30 (m, 1H), 7.52 (m, 1H), 7.75–8.02 (m, 6H).

EXAMPLE 128

3-Chloroperoxybenzoic acid (0.5 g) was added portionwise to a stirred solution of (E)-5-[5-fluoro-3-(4-methoxytetrahydropyran-4-yl)phenylthio]indan-1-one oxime (0.3 g) in methylene chloride (10 ml) which had been cooled to 0° C. The mixture was stirred at 0° C. for 10 minutes. The mixture was partitioned between ethyl acetate and a saturated aqueous sodium bicarbonate solution. The organic phase was washed with water, dried (MgSO$_4$) and evaporated. The residue was purified by column chromatography using a 5:2 mixture of petroleum ether and ethyl acetate as eluent. There was thus obtained (E)-5-[5-fluoro-3-(4-methoxytetrahydropyran-4-yl)phenylsulphonyl]indan-1-one oxime (0.277 g, 86%), m.p. 171°–172° C. (recrystallized from isopropanol);

NMR Spectrum (CD$_3$SOCD$_3$) 1.82–2.01 (m, 4H), 2.85–2.96 (m, 5H), 3.15 (m, 2H), 3.34 (s, 3H), 3.59–3.78 (m, 4H), 5.12 (s, 2H), 7.60 (m, 1H), 7.81 (m, 3H), 7.98 (m, 1H), 8.14 (m, 1H).

EXAMPLE 129

Using an analogous procedure to that described in Example 128, (E)-5-[4-(4-methoxytetrahydropyran-4-yl)thien-2-ylthio]indan-1-one oxime was oxidized to give (E)-5-[4-(4-methoxytetrahydropyran-4-yl)thien-2-ylsulphonyl]indan-1-one oxime in 89% yield, m.p. 144°–145° C. (recrystallized from isopropanol);

NMR Spectrum (CD$_3$SOCD$_3$) 1.8–2.0 (m, 4H), 2.87 (s, 3H), 2.90 (m, 2H), 3.12 (m, 2H), 3.56–3.66 (m, 4H), 5.11 (s, 2H), 7.77–8.08 (m, 5H).

EXAMPLE 130

A solution of potassium peroxymonosulphate (0.407 g) in water (5 ml) was added portionwise to a stirred solution of (E)-4'-{5-fluoro-3-[(2RS,3SR)-3-methoxy-2-methyltetrahydrofuran-3-yl]phenylthio}acetophenone oxime (0.25 g) in methanol (5 ml) which had been cooled to 0° C. The mixture was allowed to warm to ambient temperature and was stirred for 16 hours. A further portion of potassium peroxymonosulphate (0.102 g) in water (2 ml) was added and the mixture was stirred at ambient temperature for 2 hours. The mixture was partitioned between methylene chloride and water. The organic phase was washed with water and with brine, dried (MgSO$_4$) and evaporated. The residue was purified by column chromatography using a 5:3 mixture of hexane and ethyl acetate as eluent. There was thus obtained (E)-4'-{5-fluoro-3-[(2RS,3SR)-3-methoxy-2-methyltetrahydrofuran-3-yl]phenylsulphonyl}acetophenone oxime (0.19 g, 70%), m.p. 172°–173° C.

EXAMPLE 131

Using an analogous procedure to that described in Example 130, (E)-4'-{5-fluoro-3-[(2RS,3SR)-3-methoxy-2-methyltetrahydrofuran-3-yl]phenylthio}acetophenone oxime O-methyl ether was oxidized to give 4'-{5-fluoro-3-[(2RS,3SR)-3-methoxy-2-methyltetrahydrofuran-3-yl]phenylsulphonyl}acetophenone oxime O-methyl ether in 46% yield, m.p. 141°–143° C.

EXAMPLE 132

Using an analogous procedure to that described in Example 125, (E)-5-{4-[(2RS,3SR)-3-methoxy-2-methyltetrahydrofuran-3-yl] thien-2-ylthio}indan-1-one oxime was oxidized to give (E)-5-{4-[(2RS,3SR)-3-methoxy-2-methyltetrahydrofuran-3-yl]thien-2-ylsulphonyl}indan-1-one oxime in 60% yield, m.p. 170°–172° C.

EXAMPLE 133

Using an analogous procedure to that described in Example 126, (E)-4'-[3-(2,2,4-trimethyl-1,3-dioxolan-4-yl)phenylthio]acetophenone oxime was oxidized to give (E)-4'-[3-(2,2,4-trimethyl-1,3-dioxolan-4-yl)phenylsulphonyl]acetophenone oxime in 50% yield as a gum.

NMR Spectrum 1.3 (s, 3H), 1.5 (s, 6H), 2.2 (s, 3H), 4.1 (m, 2H), 7.4–7.9 (m, 8H).

EXAMPLE 134

Using an analogous procedure to that described in Example 126, (E)-4'-[3-(2,2,4-trimethyl-1,3-dioxolan-4-yl)phenylthio]acetophenone oxime O-cyanomethyl ether was oxidized to give (E)-4'-[3-(2,2,4-trimethyl-1,3-dioxolan-4-yl)phenylsulphonyl]acetophenone oxime O-cyanomethyl ether in 46% yield as a gum.

NMR Spectrum 1.3 (s, 3H), 1.5 (s, 6H), 2.26 (s, 3H), 4.1 (m, 2H), 4.8 (s, 2H), 7.4–8.0 (m, 8H).

EXAMPLE 135

Using an analogous procedure to that described in Example 126, 4'-[3-(2,4-dimethyl-1,3-dioxolan-4-yl)phenylthio]acetophenone oxime was oxidized to give 4'-[3-(2,4-dimethyl-1,3-dioxolan-4-yl)phenylsulphonyl]acetophenone oxime in 61% yield as a gum.

NMR Spectrum 1.3 (s, 3H), 1.5 (s, 3H), 2.2 (s, 3H), 3.9 (m, 2H), 5.2 (m, 1H), 7.4–8.0 (m, 8H).

EXAMPLE 136

A mixture of (E)-4'-[5-fluoro-3-(4-methoxytetrahydropyran-4-yl)phenylthio]acetophenone oxime O-ethoxycarbonylmethyl ether (0.238 g), potassium carbonate (0.072 g), water (0.2 ml) and methanol (2 ml) was stirred and heated to 50° C. for 2 hours. The mixture was evaporated and the residue was partitioned between ethyl acetate and dilute aqueous hydrochloric acid. The organic phase was washed with brine, dried (MgSO$_4$) and evaporated. The residue was purified by column chromatography using a 30:1 mixture of methylene chloride and methanol as eluent. There was thus obtained (E)-4'-[5-fluoro-3-(4-methoxytetrahydropyran-4-yl)phenylthio]acetophenone oxime O-carboxymethyl ether (0.12 g, 54%) as a foam.

NMR Spectrum (CD$_3$SOCD$_3$) 1.78–1.95 (m, 4H), 2.24 (s, 3H), 2.89 (s, 3H), 3.55–3.73 (m, 4H), 4.68 (s, 2H), 7.02 (d, 1H), 7.13 (d, 1H), 7.17 (s, 1H), 7.41 (d, 2H), 7.69 (d, 2H).

EXAMPLE 137

N-Chlorosuccinimide (0.135 g) was added to a stirred mixture of 4-5-fluoro-3-(4-methoxytetrahydropyran-4-yl)phenylthio]benzaldehyde oxime (0.361 g), pyridine (0.02 ml) and chloroform (2 ml) and the mixture was heated to 45° C. for 45 minutes. The mixture was allowed to cool to ambient temperature. Triethylamine (0.146 ml) was added. Methanethiol gas was bubbled into the mixture for 2 minutes. The mixture was partitioned between methylene chloride and water. The organic phase was washed with brine, dried (MgSO$_4$) and evaporated. The residue was purified by column chromatography using increasingly polar mixtures of petroleum ether and diethyl ether as eluent. There was thus obtained S-methyl 4-[5-fluoro-3-(4-methoxytetrahydropyran-4-yl)phenylthio]benzthioate oxime (0.138 g, 34%), m.p. 111°–112° C.;

NMR Spectrum 1.82–2.0 (m, 4H), 2.14 (s, 3H), 2.99 (s, 3H), 3.73–3.86 (m, 4H), 6.88–7.02 (m, 2H), 7.19 (s, 1H), 7.32–7.45 (m, 4H), 8.10 (broad s, 1H).

EXAMPLE 138

Using an analogous procedure to that described in Example 2, (E)-4'-[5-fluoro-3-(4-methoxytetrahydropyran-4-yl)phenylthio]-α-hydroxyacetophenone oxime O-cyanomethyl ether was reacted with methyl iodide to give (E)-4'-[5-fluoro-3-(4-methoxytetrahydropyran-4-yl)phenylthio]-α-methoxyacetophenone oxime O-cyanomethyl ether in 42% yield as an oil.

NMR Spectrum 1.83–2.01 (m, 4H), 3.0 (s, 3H), 3.32 (s, 3H), 3.76–3.86 (m, 4H), 4.59 (s, 2H), 4.84 (s, 2H), 6.90–7.03 (m, 2H), 7.20 (s, 1H), 7.35 (d, 2H), 7.67 (d, 2H).

EXAMPLE 139

Using an analogous procedure to that described in Example 66, 4'-{2-[(2RS,3RS)-3-methoxy-2-methyltetrahydrofuran-3-yl]thiazol-5-ylthio}acetophenone was reacted with hydroxylamine hydrochloride to give (E)-4'-{2-[(2RS,3RS)-3-methoxy-2-methyltetrahydrofuran-3-yl] thiazol-5-ylthio}acetophenone oxime in 98% yield as a gum.

NMR Spectrum 1.3 (d, 3H), 2.3 (s, 3H), 2.6 (m, 1H), 2.9 (m, 1H), 3.4 (s, 3H), 3.9–4.2 (m, 3H), 7.2–7.8 (m, 5H), 8.2 (broad s, 1H).

The 4'-{2-[(2RS,3RS)-3-methoxy-2-methyltetrahydrofuran-3-yl]thiazol-5-ylthio}acetophenone used as a starting material was obtained as follows:

Using analogous procedures to those described in the portion of Example 15 which is concerned with the preparation of starting materials, 2-bromothiazole was reacted with 2-methyltetrahydrofuran-3-one to give in turn:
(2RS,3RS)-3-hydroxy-2-methyl-3-(2-thiazolyl)tetrahydrofuran in 84% yield, m.p. 89°–92° C.
(2RS,3RS)-3-methoxy-2-methyl-3-(2-thiazolyl)tetrahydrofuran in 84% yield, m.p. 33°–34° C.
4'-{2-[(2RS,3RS)-3-methoxy-2-methyltetrahydrofuran-3-yl]thiazol-5-ylthio}acetophenone ethylene acetal in 90% yield as a gum; and
4'-{2-[(2RS,3RS)-3-methoxy-2-methyltetrahydrofuran-3-yl]thiazol-5-ylthio} acetophenone in 96% as an oil, NMR Spectrum 1.3 (d, 3H), 2.6 (s, 3H), 2.9 (m, 2H), 3.4 (s, 3H), 3.9–4.2 (m, 3H), 7.2–7.9 (m, 5H).

EXAMPLE 140

Using an analogous procedure to that described in Example 125, (E)-4'-{2-[(2RS,3RS)-3-methoxy-2-methyltetrahydrofuran-3-yl] thiazol-5-ylthio}acetophenone oxime was oxidized to give (E)-4'-{2-[(2RS,3RS)-3-methoxy-2-methyltetrahydrofuran-3-yl]thiazol-5-ylsulphonyl}acetophenone oxime in 80% yield, m.p. 139°–141° C.

EXAMPLE 141

Using an analogous procedure to that described in Example 23 except that no sodium iodide was added, (E)-4'-{2-[(2RS,3RS)-3 -methoxy-2-methyltetrahydrofuran-3-yl]thiazol-5-ylthio}acetophenone oxime was reacted with bromoacetonitrile to give (E)-4'-{2-[(2RS,3RS)-3-methoxy-2-methyltetrahydrofuran-3-yl]-thiazol-5-ylthio}acetophenone oxime O-cyanomethyl ether in 75% yield as an oil.

NMR Spectrum 1.3 (d, 3H), 2.2 (s, 3H), 2.6 (m, 1H), 2.9 (m, 1H), 3.4 (s, 3H), 3.9 (q, 1H), 4.1 (m, 2H), 4.8 (s, 2H), 7.2–7.8 (m, 5H).

EXAMPLE 142

Using an analogous procedure to that described in Example 125, (E)-4'-{2-[(2RS,3RS)-3-methoxy-2-methyltetrahydrofuran-3-yl]thiazol-5-ylthio}acetophenone oxime O-cyanomethyl ether was oxidized to give (E)-4'-{2-[(2RS,3RS)-3-methoxy-2-methyltetrahydrofuran-3-yl] thiazol-5-ylsulphonyl}acetophenone oxime O-cyanomethyl ether in 56% yield, m.p. 94°–99° C.

EXAMPLE 143

A mixture of (E)-4'-{2-[(2RS,3RS)-3-methoxy-2-methyltetrahydrofuran-3-yl]thiazol-5 -ylthio}acetophenone oxime (0.2 g), acetic anhydride (0.112 g), pyridine (0.15 ml) and methylene chloride (10 ml) was stirred at ambient temperature for 16 hours. The mixture was partitioned between methylene chloride and water. The organic phase was washed with 2N aqueous hydrochloric acid and with water, dried (MgSO$_4$) and evaporated. The residue was purified by column chromatography using a 4:1 mixture of hexane and ethyl acetate as eluent. There was thus obtained O-acetyl-(E)-4'-{2-[(2RS,3RS)-3 -methoxy-2-methyltetrahydrofuran-3-yl]thiazol-5-ylthio}acetophenone oxime in 94% yield as a gum.

NMR Spectrum 1.2 (d, 3H), 2.2 (s, 3H), 2.3 (s, 3H), 2.6 (m, 1H), 2.9 (m, 1H), 3.4 (s, 3H), 3.9 (q, 1H), 4.1 (m, 2H), 7.2–7.8 (m, 5H).

EXAMPLE 144

Using an analogous procedure to that described in Example 143, (E)-4'-{2-[(2RS,3RS)-3-methoxy-2-methyltetrahydrofuran-3-yl] thiazol-5-ylthio}acetophenone oxime was reacted with pivaloyl chloride to give O-pivaloyl-(E)-4'-{2-[(2RS,3RS)-3-methoxy-2-methyltetrahydrofuran-3-yl]thiazol-5-ylthio}acetophenone oxime in 81% yield as a gum.

NMR Spectrum 1.25 (d, 3H), 1.35 (s, 9H), 2.3 (s, 3H), 2.6 (m, 1H), 2.9 (m, 1H), 3.4 (s, 3H), 3.9–4.2 (m, 3H), 7.2 (m, 2H), 7.7–7.9 (m, 3H).

EXAMPLE 145

Using an analogous procedure to that described in Example 125, O-pivaloyl-(E)-4'-{2-[(2RS,3RS)-3-methoxy-2-methyltetrahydrofuran-3-yl]thiazol-5-ylthio}acetophenone oxime was oxidized to give O-pivaloyl-(E)-4'-{2-[(2RS,3RS)-3-methoxy-2-methyltetrahydrofuran-3-yl]thiazol-5-ylsulphonyl}acetophenone oxime in 75% yield, m.p. 121°–123° C.

EXAMPLE 146

Using an analogous procedure to that described in Example 66, 4'-{4-[(2R,3S)-3-methoxy-2-methyltetrahydrofuran-3-yl]thien-2-ylthio}acetophenone was reacted with hydroxylamine hydrochloride to give (E)-4'-{4-[(2R,3S)-3-methoxy-2-methyltetrahydrofuran-3-yl] thien-2-ylthio}acetophenone oxime in 87% yield, m.p. 89°–90° C.

The 4'-{4-[(2R,3S)-3-methoxy-2-methyltetrahydrofuran-3-yl]thien-2-ylthio}acetophenone used as a starting material was obtained as follows:

Using analogous procedures to those described in the portion of Example 80 which is concerned with the preparation of starting materials, 4-bromo-2-methylthiothiophene was reacted with (2R)-(+)-2-methyltetrahydrofuran-3-one to give in turn:

(2R,3S)-3-hydroxy-2-methyl-3-(2-methylthiothien-4-yl)tetrahydrofuran in 74% yield as a liquid, [alpha]$^{20}$=+10.1° (conc.=1.15 g per 100 ml of chloroform);

(2R,3S)-3-methoxy-2-methyl-3-(2-methylthiothien-4-yl)tetrahydrofuran in 96% yield as an oil;

(2R,3S)-3-(2-mercaptothien-4-yl)-3-methoxy-2-methyltetrahydrofuran in 95% yield as an oil; and 4'-{4-[(2R,3S)-3-methoxy-2-methyltetrahydrofuran-3-yl]thien-2-ylthio}acetophenone in 83% yield, m.p. 96°–98° C., [alpha]$^{20}$=+17.6° (conc.=0.915 g per 100 ml of chloroform).

The (2R)-(+)-2-methyltetrahydrofuran-3-one used as a starting material was obtained as follows:

A solution of methyl (R)-(+)-lactate (30 g) in diethyl ether (60 ml) was added dropwise to a stirred mixture of sodium hydride (65%, 10.42 g) and diethyl ether (180 ml) which had been cooled to −35° C. The mixture was allowed to warm to 0° C. and stirred for 20 minutes. The mixture was evaporated. To the residue so obtained there was added a solution of methyl acrylate (29.2 ml) in DMSO (120 ml) which had been cooled to 10° C. The mixture was stirred in an ice-bath for 30 minutes and at ambient temperature for 2 hours. The mixture was poured into cold dilute (5%) aqueous sulphuric acid and extracted with diethyl ether. The organic phase was washed with a cold aqueous sodium bicarbonate solution and with brine, dried (MgSO$_4$) and evaporated. The residue was distilled to give (2R)-4-methoxycarbonyl-2-methyltetrahydrofuran-3-one (16.5 g, 37%), b.p. 66°–68° C. (0.5 mm Hg), [alpha]$^{20}$=+55.3° (conc.=1.16 g per 100 ml of chloroform).

A mixture of the material so obtained and dilute (10%) aqueous sulphuric acid (164 ml) was stirred and heated to 70° C. for 2 hours. The mixture was cooled to ambient temperature, salt was added and the mixture was extracted with diethyl ether. The organic phase was washed with a saturated aqueous sodium bicarbonate solution and with brine, dried (MgSO$_4$) and evaporated. The residue was distilled to give (2R)-(+)-2-methyltetrahydrofuran-3-one (6.2 g, 60%), b.p. 82° C. (140 mm Hg), [alpha]$^{20}$=+118° (conc.=1.03 g per 100 ml of chloroform).

EXAMPLE 147

A solution of (E)-4'-{4-[(2R,3S)-3-methoxy-2-methyltetrahydrofuran-3-yl]thien-2 -ylthio}acetophenone oxime (5 g) in DMF (48 ml) was added to sodium hydride (60%, 1.38 g) which had been washed with pentane to remove mineral oil.

The mixture was stirred at ambient temperature for 30 minutes. The mixture was cooled to 0° C. and bromoacetonitrile (3.36 g) was added. The mixture was stirred at ambient temperature for 4 hours. The mixture was partitioned between ethyl acetate and water. The organic phase was washed with water and with brine, dried (MgSO$_4$) and evaporated. The residue was purified by column chromatography using a 7:3 mixture of hexane and ethyl acetate as eluent. There was thus obtained (E)-4'-{4-[(2R,3S)-3-methoxy-2-methyltetrahydrofuran-3-yl]thien-2-ylthio}acetophenone oxime O-cyanomethyl ether (4.8 g, 86%), m.p. 83°–84° C. (recrystallized from diethyl ether), [alpha]$^{20}$=14.7° conc.=1.025 g per 100 ml chloroform).

EXAMPLE 148

Using an analogous procedure to that described in Example 125, (E)-4'-{4-[(2R,3S)-3-methoxy-2-methyltetrahydrofuran-3-yl] thien-2-ylthio}acetophenone oxime O-cyanomethyl ether was oxidized to give (E)-4'-{4-[(2R, 3S)-3-methoxy-2-methyltetrahydrofuran-3-yl}thien-2-ylsulphonyl}acetophenone oxime O-cyanomethyl ether in 68% yield, m.p. 147°–149° C. (recrystallized from diethyl ether).

EXAMPLE 149

Using an analogous procedure to that described in Example 66, 5-{4-[(2R,3S)-3-methoxy-2-methyltetrahydrofuran-3-yl]thien-2 -ylthio}indan-1-one was reacted with hydroxylamine hydrochloride to give (E)-5-{4-[(2R,3S)-3-methoxy-2-methyltetrahydrofuran-3-yl]thien-2-ylthio}indan-1-one oxime in·87% yield, m.p. 140°–142° C.

The 5-{4-[(2R,3S)-3-methoxy-2-methyltetrahydrofuran-3-yl]thien-2-ylthio]indan-1-one used as a starting material was obtained as follows:

Using an analogous procedure to that described in the last paragraph of the portion of Example 66 which is concerned with the preparation of starting materials 5-bromoindan-1-one was reacted with (2R,3S)-3-(2-mercaptothien-4-yl)-3-methoxy-2-methyltetrahydrofuran to give the required starting material in 64% yield as a gum.

NMR Spectrum 1.26 (d, 3H), 2.5 (m, 4H), 3.05 (t, 2H), 3.23 (s, 3H), 3.82 (m, 1H), 4.0 (m, 2H), 7.1 (m, 1H), 7.16 (d, 1H), 7.3 (d, 1H), 7.4 (d, 1H), 7.62 (d, 1H).

EXAMPLE 150

Using an analogous procedure to that described in Example 11 except that sodium iodide was not added, (E)-5-{4-[(2R,3S)-3-methoxy-2-methyltetrahydrofuran-3-yl]thien-2-ylthio}indan-1-one oxime was reacted with bromoacetonitrile to give (E)-5-{4-[(2R,3S)-3-methoxy-2 -methyltetrahydrofuran-3-yl]thien-2-ylthio}indan-1-one oxime O-cyanomethyl ether in 63% yield, m.p. 77°–79° C. (recrystallized from diethyl ether).

EXAMPLE 151

Using an analogous procedure to that described in Example 11 except that sodium iodide was not added, (E)-5-{4-[(2R,3S)-3-methoxy-2-methyltetrahydrofuran-3-yl]thien-2-ylthio}indan-1-one oxime was reacted with 3-chloromethylpyridine to give (E)-5-{4-(2R,3S)-3 -methoxy-2-methyltetrahydrofuran-3-yl]thien-2-ylthio}indan-1-one oxime O-(3-pyridyl)methyl ether in 57% yield as a gum.

NMR Spectrum 1.26 (d, 3H), 2.45 (m, 2H), 2.91 (m, 4H), 3.2 (s, 3H), 3.8 (q, 1H), 3.9–4.15 (m, 2H), 5.19 (s, 2H), 7.06 (m, 1H), 7.1 (s, 1H), 7.24–7.33 (m, 3H), 7.54 (d, 1H), 7.72 (m, 1H), 8.54 (m, 1H), 8.65 (d, 1H).

EXAMPLE 152

Acetic anhydride (0.2 ml) and 4-dimethylaminopyridine (0.13 g) were added in turn to a stirred solution of (E)-5-{4-[(2R,3S)-3 -methoxy-2-methyltetrahydrofuran-3-yl] thien-2-ylthio}indan-1-one oxime (0.2 g) in methylene chloride (9 ml). The mixture was stirred at ambient temperature for 16 hours. The mixture was partitioned between ethyl acetate and water. The organic phase was washed with water and with brine, dried (MgSO$_4$) and evaporated. The residue was purified by column chromatography using a 3:1 mixture of hexane and ethyl acetate as eluent. There was thus obtained O-acetyl-(E)-5-{4-[(2R,3S)-3 -methoxy-2-methyltetrahydrofuran-3-yl]thien-2-ylthio}indan-1-one oxime (0.16 g, 72%), m.p. 110°–111° C. (recrystallized from diethyl ether).

EXAMPLE 153

Using an analogous procedure to that described in Example 152, (E)-5-{4-[(2R,3S)-3-methoxy-2-methyltetrahydrofuran-3-yl] thien-2-ylthio}indan-1-one oxime was reacted with pivaloyl chloride to give O-pivaloyl-(E)-5-{4-[(2R,3S)-3-methoxy-2-methyltetrahydrofuran-3-yl]thien-2-ylthio}indan-1-one oxime in 97% yield, m.p. 125°–126° C.

EXAMPLE 154

Using an analogous procedure to that described in Example 15, 4'-{5-[(2S,4R)-4-methoxy-2-methyltetrahydropyran-4-yl]thiazol-2-ylthio}acetophenone was reacted with hydroxylamine hydrochloride to give (E)-4'-{5-[(2S, 4R)-4-methoxy-2-methyltetrahydropyran-4-yl]thiazol-2-ylthio}acetophenone oxime in 84% yield as a foam.

NMR Spectrum (CD$_3$SOCD$_3$) 1.06 (d, 3H), 1.47–1.53 (m, 1H), 1.75–2.04 (m, 3H), 2.16 (s, 3H), 2.97 (s, 3H), 3.50–3.72 (m, 3H), 7.62 (d, 2H), 7.63 (s, 1H), 7.74 (d, 2H), 11.43 (broad s, 1H).

The 4'-{5-[(2S,4R)-4-methoxy-2-methyltetrahydropyran-4-yl]thiazol-2-ylthio}acetophenone used as a starting material was obtained as follows:

Using analogous procedures to those described in the third, fourth and fifth paragraphs of the portion of Example 20 which is concerned with the preparation of starting materials except that in the first step the reaction mixture was not allowed to warm above −40° C., the 5-lithio derivative of 4'-(2-thiazolylthio)acetophenone ethylene acetal was reacted with (2S)-2-methyltetrahydropyran-4-one [European Patent Application No. 0385662 (Example 20 thereof)] to give in turn:

4'-{5-[(2S,4R)-4-hydroxy-2-methyltetrahydropyran-4-yl] thiazol-2-ylthio}acetophenone ethylene acetal in 15% yield as an oil;

4'-{5-(2S,4R)-4-methoxy-2-methyltetrahydropyran-4-yl] thiazol-2-ylthio}acetophenone ethylene acetal in 71% yield as an oil; and 4'-{5-[(2S,4R)-4-methoxy-2-methyltetrahydropyran-4-yl] thiazol-2-ylthio}acetophenone in 97% yield as an oil.

EXAMPLE 155

Using an analogous procedure to that described in Example 2, (E)-4'-{5-[(2S,4R)-4-methoxy-2-methyltetrahydropyran-4-yl]thiazol-2-ylthio}acetophenone oxime was reacted with bromoacetonitrile to give (E)-4'-{5-[(2S,4R)-4-methoxy-2-methyltetrahydropyran-4-yl]thiazol-2-ylthio}acetophenone oxime O-cyanomethyl ether in 68% yield as an oil.

NMR Spectrum 1.18 (d, 3H), 1.54–1.62 (m, 1H), 1.86–2.05 (m, 3H), 2.27 (s, 3H), 3.05 (s, 3H), 3.75–3.85 (m, 3H), 4.84 (s, 2H), 7.49 (s, 1H), 7.61 (d, 2H), 7.72 (d, 2H).

EXAMPLE 156

Using an analogous procedure to that described in Example 68, 2-chloro-4-[5-fluoro-3-(4-methoxytetrahydropyran-4-yl)phenylthio]benzaldehyde was reacted with hydroxylamine hydrochloride to give 2-chloro-4-[5-fluoro-3-(4-methoxytetrahydropyran-4-yl)phenylthio]benzaldehyde oxime in 83% yield as a gum.

NMR Spectrum 1.8–2.0 (m, 4H), 2.99 (s, 3H), 3.75–3.90 (m, 4H), 6.9–7.05 (m, 2H), 7.1–7.3 (m, 3H), 7.81 (d, 1H), 8.48 (s, 1H), 9.37 (s, 1H).

The 2-chloro-4-[5-fluoro-3-(4-methoxytetrahydropyran-4-yl)phenylthio]benzaldehyde used as a starting material was obtained as follows:

Using an analogous procedure to that described in the last paragraph of the portion of Example 66 which is concerned with the preparation of starting materials, 2-chloro-4-fluorobenzaldehyde was reacted with 4-(5-fluoro-3-mercaptophenyl)-4-methoxytetrahydropyran to give the required starting material in 96% yield as a gum.

NMR Spectrum 1.8–2.0 (m, 4H), 3.01 (s, 3H), 3.8–3.9 (m, 4H), 7.1–7.2 (m, 2H), 7.33 (m, 1H), 7.81 (d, 1H), 10.37 (s, 1H).

EXAMPLE 157

Using an analogous procedure to that described in Example 66, 4'-{5-[2RS,3RS)-3-methoxy-2-methyltetrahydrofuran-3-yl] thiazol-2-ylthio}acetophenone was reacted with hydroxylamine hydrochloride to give (E)-4'-{5-[(2RS, 3RS)-3-methoxy-2-methyltetrahydrofuran-3-yl] thiazol-2-ylthio}acetophenone oxime in 58% yield as a gum.

NMR Spectrum 1.26 (d, 3H), 2.29 (s, 3H), 2.33 (m, 1H), 2.56 (m, 1H), 2.7 (s, 3H), 3.19 (s, 3H), 3.80 (q, 1H), 3.95 (m, 1H), 4.06 (q, 1H), 7.55 (s, 1H), 7.62 (m, 2H), 7.69 (m, 2H), 8.86 (broad s, 1H).

The 4'-{5-[(2RS,3RS)-3-methoxy-2-methyltetrahydrofuran-3-yl]thiazol-2-ylthio}acetophenone used as a starting material was obtained as follows:

A mixture of 2-bromothiazole (32.8 g), potassium iodide (2 g), sodium methanethiolate (14.7 g) and methanol (200 ml) was stirred and heated to reflux for 8 hours. The bulk of the solvent was evaporated and the residue was partitioned between diethyl ether and water. The organic phase was washed with water and with brine, dried (MgSO$_4$) and evaporated. The residue was distilled to give 2-methylthiothiazole (18.2 g) as an oil (b.p. 58°–60° C. at 10 mm Hg).

n-Butyl-lithium (1.6M in hexane, 87 ml) was added to a stirred solution of 2-methylthiothiazole (13.1 g) in THF (80 ml) which had been cooled to 0° C. The mixture was stirred at 0° C. for 75 minutes. A solution of 2-methyltetrahydrofuran-3-one (11.95 g) in THF (30 ml) was added and the mixture was stirred at ambient temperature for 16 hours. The mixture was partitioned between diethyl ether and a saturated aqueous ammonium chloride solution. The organic phase was washed with brine, dried (MgSO$_4$) and evaporated. The residue was purified by column chromatography using a 2:1 mixture of hexane and ethyl acetate as eluent.

There was thus obtained (2RS,3RS)-3-hydroxy-2-methyl-3-(2-methylthiothiazole-5-yl)tetrahydrofuran (15.5 g, 67%), m.p. 79°–80° C.

Using an analogous procedure to that described in the second paragraph of the portion of Example 66 which is concerned with the preparation of starting materials, the product so obtained was reacted with methyl iodide to give (2RS,3RS)-3-methoxy-2-methyl-3-(2-methylthiothiazole-5-yl)tetrahydrofuran in 68% yield, m.p. 51°–52° C.

Using an analogous procedure to that described in the fourth paragraph of the portion of Example 80 which is concerned with the preparation of starting materials, the product so obtained was treated with sodium methanethiolate to give (2RS,3RS)-3-(2-mercaptothiazol-5-yl)-3-methoxy-2-methyltetrahydrofuran in 60% yield, m.p. 126°–127° C.

Using an analogous procedure to that described in the portion of Example 1 which is concerned with the preparation of starting materials, the product so obtained was reacted with 4'-iodoacetophenone to give 4'-{5-(2RS,3RS)-3-methoxy-2-methyltetrahydrofuran-3-yl]thiazol-2-ylthio}acetophenone in 64% yield as a gum.

NMR Spectrum 1.27 (d, 3H), 2.36 (m, 1H), 2.59 (m, 1H), 2.61 (s, 3H), 3.81 (m, 1H), 3.97 (m, 1H), 4.07 (q, 1H), 7.60 (m, 2H), 7.63 (s, 1H), 7.95 (m, 2H).

EXAMPLE 158

Using an analogous procedure to that described in Example 125, (E)-4'-[5-(4-methoxytetrahydropyran-4-yl)thiazol-2-ylthio]acetophenone oxime O-cyanomethyl ether was oxidized to give (E)-4'-[5-(4-methoxytetrahydropyran-4-yl)thiazol-2-ylsulphonyl]acetophenone oxime O-cyanomethyl ether in 57% yield, m.p. 115°–117° C.;

NMR Spectrum 2.0–2.06 (m, 4H), 2.29 (s, 3H), 3.09 (s, 3H), 3.75–3.82 (m, 4H), 4.86 (s, 2H), 7.74 (s, 1H), 7.87 (d, 2H), 8.13 (d, 2H).

EXAMPLE 159

3-Chloroperoxybenzoic acid (0.064 g) was added to a stirred solution of (E)-4'-[5-(4-methoxytetrahydropyran-4-yl)thiazol-2-ylthio]acetophenone oxime O-cyanomethyl ether (0.1 g) in methylene chloride (2.5 ml) which had been cooled to 0° C. The mixture was stirred for 1 hour and allowed to warm to ambient temperature. The mixture was basified by the addition of a saturated aqueous sodium bicarbonate solution and extracted with ethyl acetate. The organic phase was washed with brine, dried (MgSO$_4$) and evaporated. The residue was purified by column chromatography using a 2:1 mixture of ethyl acetate and petroleum ether as eluent. There was thus obtained (E)-4'-[5-(4-methoxytetrahydropyran-4-yl)thiazol-2-ylsulphinyl]acetophenone oxime O-cyanomethyl ether in 87% yield, m.p. 98°–100° C.;

NMR Spectrum 1.97–2.05 (m, 4H), 2.28 (s, 3H), 3.05 (s, 3H), 3.74–3.81 (m, 4H), 4.84 (s, 2H), 7.66 (s, 1H), 7.84 (s, 4H).

EXAMPLE 160

Using an analogous procedure to that described in Example 15, 4'-[5-(4-methoxytetrahydropyran-4-yl)thiazol-2-yloxymethyl]acetophenone was reacted with hydroxylamine hydrochloride to give (E)-4'-[5-(4-methoxytetrahydropyran-4-yl)thiazol-2-yloxymethyl]acetophenone oxime in 57% yield, m.p. 107°–109° C.;

NMR Spectrum 1.93–2.07 (m, 4H), 2.28 (s, 3H), 3.09 (s, 3H), 3.68–3.85 (m, 4H), 5.42 (s, 2H), 6.95 (s, 1H), 7.44 (d, 2H), 7.67 (d, 2H).

The 4'-[5-(4-methoxytetrahydropyran-4-yl)thiazol-2-yloxymethyl]acetophenone used as a staring material was obtained as follows:

Using an analogous procedure to that described in the first paragraph of the portion of Example 43 which is concerned with the preparation of starting materials, 4-(2-methyl-1,3-dioxolan-2-yl)benzyl alcohol was reacted with 2,5-dibromothiazole to give 4'-(5-bromothiazole-2-yloxymethyl)acetophenone ethylene acetal in 60% yield as an oil.

Using analogous procedures to those described in the second and third paragraphs of the portion of Example 21 which is concerned with the preparation of starting materials, the product so obtained was converted in turn into:

4'-[5-(4-hydroxytetrahydropyran-4-yl)thiazol-2-yloxymethyl]acetophenone ethylene acetal in 45% yield, m.p. 129°–131° C.; and 4'-[5-(4-methoxytetrahydropyran-4-yl)thiazol-2-yloxymethyl] acetophenone in 21% yield as an oil.

EXAMPLE 161

Using an analogous procedure to that described in Example 2, (E)-4'-[5-(4-methoxytetrahydropyran-4-yl)thiazol-2-yloxymethyl] acetophenone oxime was reacted with bromoacetonitrile to give (E)-4'-[5-(4-methoxytetrahydropyran-4-yl)thiazol-2-yloxymethyl]acetophenone oxime O-cyanomethyl ether in 88% yield, m.p. 99°–101° C.;

NMR Spectrum 1,94–2.08 (m, 4H), 2.27 (s, 3H), 3.09 (s, 3H), 3.71–3.84 (m, 4H), 4.83 (s, 2H), 5.44 (s, 2H), 6.94 (s, 1H), 7.47 (d, 2H), 7.69 (d, 2H).

EXAMPLE 162

Using an analogous procedure to that described in Example 50, 4'-[5-fluoro-3-(4-methoxytetrahydropyran-4-yl)phenylsulphonyl]acetophenone was reacted with hydroxylamine hydrochloride to give (E)-4'-[5-fluoro-3-(4-methoxytetrahydropyran-4-yl)phenylsulphonyl]acetophenone oxime in 83% yield, m.p. 180°–181° C.;

NMR Spectrum 1.83–2.03 (m, 4H), 2.27 (s, 3H), 2.97 (s, 3H), 3.77–3.88 (m, 4H), 7.31 (m, 1H), 7.52 (m, 1H), 7.7–8.0 (m, 5H).

The 4'-[5-fluoro-3-(4-methoxytetrahydropyran-4-yl)phenylsulphonyl]acetophenone used as a starting material was obtained by the oxidation of 4'-[5-fluoro-3-(4-methoxytetrahydropyran-4-yl)phenylthio]acetophenone using an analogous procedure to that described in Example 125. There was thus obtained the required starting material in 83% yield, m.p. 141° C.

EXAMPLE 163

Using an analogous procedure to that described in Example 2, (E)-4'-[5-fluoro-3-(4-methoxytetrahydropyran-4-yl)phenylsulphonyl]acetophenone oxime was reacted with bromoacetonitrile to give (E)-4'-[5-fluoro-3-(4-methoxytetrahydropyran-4-yl)phenylsulphonyl]acetophenone O-cyanomethyl ether in 76% yield, m.p. 178°–179° C.;

NMR Spectrum 1.83–2.02 (m, 4H), 2.28 (s, 3H), 2.97 (s, 3H), 3.78–3.88 (m, 4H), 4.85 (s, 2H), 7.32 (m, 1H), 7.55 (m, 1H), 7.76–8.01 (m, 5H).

EXAMPLE 164 using an analogous procedure to that described in Example 50, 4'-[5-fluoro-3-(4-methoxytetrahydropyran-4-yl)phenylthio]-α-methylthioacetophenone was reacted with hydroxylamine hydrochloride to give (E)-4'-[5-fluoro-3-(4-methoxytetrahydropyran-4-yl)phenylthio]-α-methylthioacetophenone oxime in 55% yield, m.p. 103°–104° C.;

NMR Spectrum 1.82–2.0 (m, 4H), 2.12 (s, 3H), 2.97 (s, 3H), 3.75–3.85 (m, 6H), 6.89 (m, 1H), 6.97 (m, 1H), 7.07 (s, 1H), 7.35 (d, 2H), 7.67 (d, 2H).

The 4'-[5-fluoro-3-(4-methoxytetrahydropyran-4-yl)phenylthio]-α-methylthioacetophenone used as a starting material was obtained as follows:

A solution of sodium methanethiolate (0.77 g) in water (0.5 ml) was added to a solution of α-bromo-4'-[5-fluoro-3-(4 -methoxytetrahydropyran-4-yl)phenylthio]acetophenone (0.439 g) in diethyl ether (5 ml). The mixture was stirred vigorously at ambient temperature for 16 hours. The mixture was partitioned between diethyl ether and water. The organic phase was washed with brine, dried ($MgSO_4$) and evaporated. The residue was purified by column chromatography using a 4:1 mixture of petroleum ether and ethyl acetate as eluent. There was thus obtained the required starting material (0.23 g, 57%) as an oil.

EXAMPLE 165

Using an analogous procedure to that described in Example 130, (E)-4'-[4-(4-methoxytetrahydropyran-4-yl)thien-2-ylthio]acetophenone oxime was oxidized to give (E)-4'-[4-(4-methoxytetrahydropyran-4-yl)thien-2-ylsulphonyl] acetophenone oxime in 59% yield, m.p. 141°–142° C.;

NMR Spectrum 1.84–1.98 (m, 4H), 2.25 (s, 3H), 2.97 (s, 3H), 3.69–3.83 (m, 4H), 7.42 (s, 1H), 7.67 (s, 1H), 7.78 (d, 2H), 7.98 (d, 2H).

EXAMPLE 166

Using an analogous procedure to that described in Example 2, (E)-4'-[4-(4-methoxytetrahydropyran-4-yl)thien-2-ylsulphonyl] acetophenone oxime was reacted with bromoacetonitrile to give (E)-4'-[4-(4-methoxytetrahydropyran-4-yl)thien-2-ylsulphonyl]acetophenone oxime O-cyanomethyl ether in 75% yield, m.p. 114°–116° C.;

NMR Spectrum 1.88–1.98 (m, 4H), 2.29 (s, 3H), 2.98 (s, 3H), 3.70–3.82 (m, 4H), 4.83 (s, 2H), 7.44 (s, 1H), 7.66 (s, 1H), 7.82 (d, 2H), 7.98 (d, 2H).

EXAMPLE 167

Using an analogous procedure to that described in Example 50, 6-[5-fluoro-3-(4-methoxytetrahydropyran-4-yl)phenylsulphonyl] pyrid-3-yl methyl ketone was reacted with hydroxylamine hydrochloride to give 6-[5-fluoro-3-(4-methoxytetrahydropyran-4-yl)phenylsulphonyl] pyrid-3-yl methyl ketone oxime in 96% yield.

NMR Spectrum 1.85–2.05 (m, 4H), 2.29 (s, 3H), 2.98 (s, 3H), 3.76–3.88 (m, 4H), 7.37 (m, 1H), 7.69 (m, 1H), 7.88 (m, 2H), 8.10–8.20 (m, 2H), 8.95 (s, 1H).

The starting material, m.p. 198° C., was obtained in 88% yield by the oxidation of 6-[5-fluoro-3-(4-methoxytetrahydropyran-4-yl)phenylthio]pyrid-3-yl methyl ketone using an analogous procedure to that described in Example 125.

EXAMPLE 168

Using an analogous procedure to that described in Example 2, 6-[5-fluoro-3-(4-methoxytetrahydropyran-4-yl)phenylsulphonyl]pyrid-3-yl methyl ketone oxime was reacted with bromoacetonitrile to give 6-[5-fluoro-3-(4-methoxytetrahydropyran-4-yl)phenylsulphonyl]pyrid-3-yl methyl ketone oxime O-cyanomethyl ether in 61% yield, m.p. 123°–124° C.;

NMR Spectrum 1.88–2.06 (m, 4H), 2.30 (s, 3H), 2.99 (s, 3H), 3.78–3.88 (m, 4H), 4.87 (s, 2H), 7.39 (m, 1H), 7.70 (m, 1H), 7.88 (s, 1H), 8.22 (s, 1H), 8.94 (s, 1H).

EXAMPLE 169

Using an analogous procedure to that described in Example 125, 7-[5-fluoro-3-(4-methoxytetrahydropyran-4-yl)phenylthio]chroman-4-one oxime was oxidized to give 7-[5-fluoro-3-(4-methoxytetrahydropyran-4-yl)phenylsulphonyl]chroman-4-one oxime in 54% yield, m.p. 209°–210° C.;

NMR Spectrum 1.86–2.02 (m, 4H), 2.9–3.02 (s & t, 5H), 3.79–3.88 (m, 4H), 4.28 (t, 2H), 7.32 (m, 1H), 7.42–7.67 (m, 3H), 7.76 (s, 1H), 8.0 (d, 1H).

EXAMPLE 170 n-Butyl-lithium (1.6M in hexane, 4.4 ml) was added dropwise to a stirred solution of di-isopropylamine (1 ml) in THF (11 ml) which had been cooled to −78° C. The mixture was stirred at −60° C. for 30 minutes. The mixture was recooled to −78° C. and a solution of (2S,4R)-4-methoxy-2-methyl-4-(3-thienyl)tetrahydropyran (1 g) in THF (2.5 ml) was added dropwise. The mixture was allowed to warm to −15° C. and was stirred for 3 hours. The mixture was recooled to −78° C. and a solution of di-[(E)-1-tert-butyldimethylsilyloxyiminoindan-5-yl]disulphide (2.61 g) in THF (18 ml) was added. The mixture was stirred at −78° C. for 30 minutes and then allowed to warm to ambient temperature. The mixture was poured into a cold aqueous ammonium chloride solution and extracted with diethyl ether. The organic phase was dried (MgSO$_4$) and evaporated. The residue was purified by column chromatography using a 9:1 mixture of petroleum ether and ethyl acetate as eluent. There was thus obtained (E)-5-{4-[(2S,4R)-4-methoxy-2-methyltetrahydropyran-4-yl]thien-2-ylthio}indan-1-one oxime O-tert-butyldimethylsilyl ether (1.65 g, 72%).

Tetrabutylammonium fluoride (1.1M in THF, 2.5 ml) was added dropwise to a stirred solution of a portion (0.36 g) of the material so obtained in THF (5 ml). The mixture was stirred at ambient temperature for 1 hour. The mixture was partitioned between ethyl acetate and water. The organic phase was washed with water, dried (MgSO$_4$) and evaporated. The residue was purified by column chromatography using a 7:3 mixture of petroleum ether and ethyl acetate as eluent. There was thus obtained (E)-5-{4-[(2S,4R)-4-methoxy-2-methyltetrahydropyran-4-yl]thien-2-ylthio}indan-1-one oxime (0.22 g, 80%), m.p. 98°–100° C.;

NMR Spectrum (CD$_3$SOCD$_3$) 1.05 (d, 3H), 1.43 (m, 1H), 1.77 (m, 1H), 1.92–2.08 (m, 2H), 2.73 (m, 2H), 2.83–2.97 (m, 5H), 3.62–3.76 (m, 3H), 7.02 (d, 1H), 7.10 (s, 1H), 7.29 (s, 1H), 7.41 (d, 1H), 7.50 (s, 1H).

The (2S,4R)-4-methoxy-2-methyl-4-(3-thienyl)tetrahydropyran used as a starting material was obtained as follows:

A solution of 1,2-dibromoethane (5 g) in diethyl ether (10 ml) was added to a stirred suspension of magnesium (3 g) in diethyl ether (10 ml) to initiate the formation of a Grignard reagent. A mixture of 1,2-dibromoethane (16.7 g) and 3-bromothiophene (4 g) in diethyl ether (30 ml) was added dropwise. The mixture was stirred and heated to reflux for 2 hours. A solution of (2S)-2-methyltetrahydropyran-4-one (2 g) in diethyl ether (5 ml) was added and the mixture was heated to reflux for 1 hour. The mixture was partitioned between ethyl acetate and water. The organic phase was dried (MgSO$_4$) and evaporated. The residue was purified by column chromatography using a 7:3 mixture of petroleum ether and ethyl acetate as eluent. There were thus obtained in turn (2S,4R)-4-hydroxy-2-methyl-4-(3-thienyl)tetrahydropyran (0.685 g, 18.5%) and the corresponding (2S,4S)-isomer (1 g, 32%).

Using an analogous procedure to that described in Example 2, the (2S,4R)-isomer was reacted with methyl iodide to give (2S,4R)-4-methoxy-2-methyl-4-(3-thienyl)tetrahydropyran in 61% yield as an oil.

EXAMPLE 171

Using an analogous procedure to that described in Example 2, (E)-5-{4-[(2S,4R)-4-methoxy-2-methyltetrahydropyran-4-yl]thien-2-ylthio}indan-1-one oxime was reacted with bromoacetonitrile to give (E)-5-{4-[(2S,4R)-4-methoxy-2-methyltetrahydropyran-4-yl]thien-2-ylthio}indan-1-one oxime O-cyanomethyl ether in 78% yield as an oil.

NMR Spectrum (CD$_3$SOCD$_3$) 1.11 (d, 3H), 1.50 (m, 1H), 1.84 (m, 1H), 2.02–2.17 (m, 2H), 2.87 (m, 2H), 2.95–3.05 (m, 5H), 3.68–3.80 (m, 3H), 4.93 (s, 2H), 7.10 (d, 1H), 7.18 (s, 1H), 7.38 (s, 1H), 7.55 (d, 1H), 7.60 (s, 1H).

EXAMPLE 172

Using analogous procedures to those described in Example 170, di-[(E)-4-(1-tert-butyldimethylsilyloxyiminoethyl)phenyl]disulphide was reacted with (2S,4R)-4-methoxy-2-methyl-4-(3-thienyl)tetrahydropyran to give (E)-4'-{4-[(2S,4R)-4-methoxy-2 -methyltetrahydropyran-4-yl]thien-2-ylthio}acetophenone oxime in 63% yield as an oil.

NMR Spectrum (CD$_3$SOCD$_3$) 1.12 (d, 3H), 1.50 (m, 1H), 1.78–2.17 (m, 3H), 2.19 (s, 3H), 3.02 (s, 3H), 3.70–3.82 (m, 3H), 7.17 (d, 2H), 7.36 (s, 1H), 7.57 (s, 1H), 7.61 (d, 2H).

The di-[(E)-4-(1-tert-butyldimethylsilyloxyiminoethyl)phenyl]disulphide used as a starting material was obtained in 72% yield from di-(4-acetylphenyl) disulphide using analogous procedures to those described in the second and third paragraphs of the portion of Example 95 which is concerned with the preparation of starting materials.

EXAMPLE 173

Using an analogous procedure to that described in Example 2, (E)-4'-{4-[(2S,4R)-4-methoxy-2-methyltetrahydropyran-4-yl]thien-2-ylthio}acetophenone oxime was reacted with bromoacetonitrile to give (E)-4'-{4-[(2S,4R)-4-methoxy-2-methyltetrahydropyran-4-yl]thien-2-ylthio}acetophenone oxime O-cyanomethyl ether in 82% yield as an oil.

NMR Spectrum (CD$_3$SOCD$_3$) 1.12 (d, 3H), 1.50 (m, 1H), 1.8–2.18 (m, 3H), 2.25 (s, 3H), 3.02 (s, 3H), 3.72–3.82 (m, 3H), 5.0 (s, 2H), 7.21 (d, 2H), 7.40 (s, 1H), 7.61 (s, 1H), 7.68 (d, 2H).

EXAMPLE 174

Using an analogous procedure to that described in Example 147, (E)-7-[4-(2,2,4-trimethyl-1,3-dioxolan-4-yl)thien-2-ylthio]-chroman-4-one oxime was reacted with bromoacetonitrile to give (E)-7-[4-(2,2,4-trimethyl-1,3-dioxolan-4-yl)thien-2-ylthio]chroman-4-one oxime O-cyanomethyl ether in 77% yield as a gum.

NMR Spectrum (CD$_3$SOCD$_3$) 1.32 (s, 3H), 1.4 (s, 3H), 1.55 (s, 3H), 2.9 (t, 2H), 4.0 (q, 2H), 4.2 (t, 2H), 5.05 (s, 2H), 6.55 (m, 1H), 6.8 (m, 1H), 7.4 (d, 1H), 7.7 (m, 2H).

EXAMPLE 175

Using an analogous procedure to that described in Example 31, (E)-4'-[4-(2,2,4-trimethyl-1,3-dioxolan-4-yl)thien-2-ylthio]acetophenone oxime was reacted with acetyl chloride to give O-acetyl-(E)-4'-[4-(2,2,4-trimethyl-1,3-dioxolan-4-yl)thien-2-ylthio]acetophenone oxime in 83% yield as a gum.

NMR Spectrum (CD$_3$SOCD$_3$) 1.35 (s, 3H), 1.40 (s, 3H), 1.55 (s, 3H), 2.2 (s, 3H), 2.3 (s, 3H), 3.95–4.08 (q, 2H), 7.25 (d, 2H), 7.45 (d, 1H), 7.7 (d, 1H), 7.75 (d, 2H).

EXAMPLE 176

Using an analogous procedure to that described in Example 68, 4'-{4-[(4S)-2,2,4-trimethyl-1,3-dioxolan-4-yl]thien-2-ylthio}acetophenone was reacted with hydroxylamine hydrochloride to give (E)-4'-{4-[(4S)-2,2,4-trimethyl-1,3-dioxolan-4-yl]thien-2-ylthio}acetophenone oxime in 95% yield as a gum.

NMR Spectrum (CD$_3$SOCD$_3$) 1.35 (s, 3H), 1.4 (s, 3H), 1.5 (s, 3H), 2.1 (s, 3H), 3.98–4.05 (q, 2H), 7.2 (d, 2H), 7.4 (d, 1H), 7.6 (m, 3H).

The 4'-{4-[(4S)-2,2,2-trimethyl-1,3-dioxolan-4-yl]thien-2-ylthio}acetophenone used as a starting material was obtained as follows:

n-Butyl-lithium (1.55M in hexane, 37 ml) was added to a stirred mixture of methyltriphenylphosphonitum bromide (21.4 g) and THF (100 ml) which had been cooled to 10° C. The mixture was stirred at ambient temperature for 90 minutes. The mixture was recooled in an ice-bath and a solution of 4-acetyl-2-bromothiophene (*Synth. Comm.*, 1981, 29–34; 11 g) in THF (60 ml) was added. The mixture was stirred at 0° C. for 1 hour and at ambient temperature for 2 hours. The mixture was partitioned between diethyl ether and a saturated aqueous ammonium chloride solution. The organic phase was washed with water and with brine, dried (MgSO$_4$) and evaporated. The residue was purified by column chromatography using hexane as eluent. There was thus obtained 2-bromo-4-isopropenylthiophene (9 g, 85%).

Using an analogous procedure to that described in the first paragraph of the portion of Example 80 which is concerned with the preparation of starting materials, the product so obtained was reacted with dimethyl disulphide to give 4-isopropenyl-2-methylthiothiophene in 87% yield as an oil, NMR Spectrum 2.08 (s, 3H), 2.5 (s, 3H), 5.0 (m, 1H), 5.3 (m, 1H), 7.13 (d, 1H), 7.25 (d, 1H).

The compound so obtained (3.1 g) was added to a vigorously stirred mixture of an osmium dihydroquinine complex known as AD-mix-α (25.2 g; *J. Org. Chem.*, 1992, 57, 2768–2771), tert-butanol (90 ml) and water (90 ml) which had been cooled to 0° C. The mixture was stirred at 0° C. for 6 hours and stored at −5° C. for 16 hours. Sodium sulphite (10 g) was added and the mixture was stirred and allowed to warm to ambient temperature. The mixture was partitioned between ethyl acetate and water. The organic phase was dried (MgSO$_4$) and evaporated. The residue was purified by column chromatography using a 5:3 mixture of hexane and ethyl acetate as eluent. There was thus obtained 4-[(2S)-1,2-dihydroxyprop-2-yl]-2-methylthiothiophene (3.41 g, 92%), m.p. 71°–73° C., [alpha]$^{25}$=+14.8° (conc.= 0.5 g per 100 ml of methylene chloride).

Using an analogous procedure to that described in Example 67, the product so obtained was reacted with acetone dimethyl acetal to give 2-methylthio-4-[(4S)-2,2,4-trimethyl-1,3-dioxolan-4-yl]thiophene in 87% yield as an oil, NMR Spectrum (CD$_3$SOCD$_3$) 1.3 (s, 3H), 1.4 (s, 3H), 1.5 (s, 3H), 2.5 (s, 3H), 3.9–4.0 (q, 2H), 7.1 (d, 1H), 7.3 (d, 1H).

Using an analogous procedure to that described in the fourth paragraph of the portion of Example 80 which is concerned with the preparation of starting materials, the product so obtained was reacted with sodium methanethiolate to give 2-mercapto-4-[(4S)-2,2,4-trimethyl-1,3-dioxolan-4-yl]thiophene.

Using an analogous procedure to that described in the last paragraph of the portion of Example 66 which is concerned with the preparation of starting materials, the crude product so obtained was reacted with 4'-fluoroacetophenone to give 4'-{4-[(4S)-2,2,4-trimethyl-1,3-dioxolan-4-yl]thien-2-ylthio}acetophenone in 71% yield as a gum, NMR Spectrum (CD$_3$SOCD$_3$) 1.35 (s, 3H), 1.4 (s, 3H), 1.55 (s, 3H), 2.5 (s, 3H), 3.95–4.1 (q, 2H), 7.2 (d, 2H), 7.45 (d, 1H), 7.7 (d, 1H), 7.9 (d, 2H).

EXAMPLE 177

Using an analogous procedure to that described in Example 147, (E)-4'-{4-[(4S)-2,2,4-trimethyl-1,3-dioxolan-4-yl]thien-2-ylthio}acetophenone oxime was reacted with bromoacetonitrile to give (E)-4'-{4-[(4S)-2,2,4-trimethyl-1,3-dioxolan-4-yl]thien-2-ylthio}acetophenone oxime O-cyanomethyl ether in 82% yield as an oil.

NMR Spectrum (CD$_3$SOCD$_3$) 1.45 (s, 3H), 1.5 (s, 3H), 1.65 (s, 3H), 2.3 (s, 3H), 4.05–4.2 (q, 2H), 5.2 (s, 2H), 7.35 (d, 2H), 7.5 (d, 1H), 7.7–7.8 (m, 3H).

EXAMPLE 178

Using an analogous procedure to that described in Example 126, (E)-4'-{4-[(4S)-2,2,4-trimethyl-1,3-dioxolan-4-yl]thien-2-ylthio}acetophenone oxime was oxidized to give (E)-4'-{4-[(4S)-2,2,4-trimethyl-1,3-dioxolan-4-yl]thien-2-ylsulphonyl}acetophenone oxime in 81% yield as a foam.

NMR Spectrum (CD$_3$SOCD$_3$) 1.3 (s, 3H), 1.4 (s, 3H), 1.5 (s, 3H), 2.18 (s, 3H), 3.92–4.04 (q, 2H), 7.8–8.0 (m, 6H), 11.6 (broad s, 1H).

EXAMPLE 179

Using an analogous procedure to that described in Example 68, 4'-{5-[(4R)-2,2,4-trimethyl-1,3-dioxolan-4-yl]thiazol-2-ylthio}acetophenone was reacted with hydroxylamine hydrochloride to give (E)-4'-{5-[(4R)-2,2,4-trimethyl-1,3-dioxolan-4-yl]thiazol-2-ylthio}acetophenone oxime in 82% yield as a gum.

NMR Spectrum (CD$_3$SOCD$_3$) 1.3 (s, 3H), 1.35 (s, 3H), 1.6 (s, 3H), 2.18 (s, 3H), 4.0 (q, 2H), 7.6 (d, 2H), 7.68 (s, 1H), 7.75 (d, 2H), 11.4 (broad s, 1H).

The 4'-{5-[(4R)-2,2,4-trimethyl-1,3-dioxolan-4-yl]thiazol-2-ylthio}acetophenone used as a starting material was obtained as follows:

n-Butyl-lithium (1.55M in hexane, 30 ml) was added to a stirred solution of 2-methylthiothiazole (5.4 g) in diethyl ether which had been cooled to −10° C. The mixture was stirred at −10° C. for 20 minutes. A solution of acetone (9.2 ml) in diethyl ether (10 ml) was added. The mixture was stirred at −5° C. for 4 hours. The mixture was partitioned between diethyl ether and a saturated aqueous ammonium chloride solution. The organic layer was washed with brine, dried (MgSO$_4$) and evaporated. The residue was purified by column chromatography using a 3:2 mixture of hexane and ethyl acetate as eluent. There was thus obtained 5-(2-hydroxyprop-2-yl)-2-methylthiothiazole (6.2 g, 80%) as an oil.

A mixture of the product so obtained, triethyl orthoformate (5.8 ml), 4-toluenesulphonic acid (0.065 g) and ethanol (40 ml) was stirred and heated to reflux for 1 hour. The bulk of the ethanol was evaporated and the residue was partitioned between diethyl ether and water. The organic phase was washed with brine, dried (MgSO$_4$) and evaporated. The residue was purified by column chromatography using a 10:1 mixture of toluene and ethyl acetate as eluent. There was thus obtained 5-(2-ethoxyprop-2-yl)-2-methylthiothiazole (5.2 g, 65%) as an oil.

A mixture of a portion (4.37 g) of the material so obtained, boron trifluoride ether complex (6 ml) and methylene chloride (10 ml) was stirred at ambient temperature for 3 hours. The mixture was evaporated and the residue was partitioned between diethyl ether and a saturated aqueous potassium carbonate solution. The organic phase was washed with brine, dried (MgSO$_4$) and evaporated. The residue was purified by column chromatography using a 50:3 mixture of hexane and ethyl acetate as eluent. There was thus obtained 5-isopropenyl-2-methylthiothiazole (2.55 g, 74%) as an oil.

NMR Spectrum 2.1 (s, 3H), 2.7 (s, 3H), 5.0–5.2 (m, 2H), 7.5 (s, 1H).

Using analogous procedures to those described in the third to sixth paragraphs of the portion of Example 176 which is concerned with the preparation of starting materials, the product so obtained was converted in turn into:
5-[(2R)-1,2-dihydroxyprop-2-yl]-2-methylthiothiazole in 83% yield, m.p. 107°–109° C.;
2-methylthio-5-[(4R)-2,2,4-trimethyl-1,3-dioxolan-4-yl]thiazole in 88% yield as an oil,
NMR Spectrum (CD$_3$SOCD$_3$) 1.3 (s, 3H), 1.4 (s, 3H), 1.6 (s, 3H), 2.65 (s, 3H), 4.0–4.1 (q, 2H), 7.55 (s, 1H);
2-mercapto-5-[(4R)-2,2,4-trimethyl-1,3-dioxolan-4-yl]thiazole in quantitative yield; and
4'-{5-[(4R)-2,2,4-trimethyl-1,3-dioxolan-4-yl]thiazol-2-ylthio}acetophenone in 63% yield as an oil,
NMR Spectrum (CD$_3$SOCD$_3$) 1.3 (s, 3H), 1.4 (s, 3H), 1.6 (s, 3H), 2.6 (s, 3H), 4.0 (q, 2H), 7.6–8.0 (m, 5H).

EXAMPLE 180

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
| --- | --- |
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
| --- | --- |
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
| --- | --- |
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d) Capsule | mg/capsule |
| --- | --- |
| Compound X | 10 |
| Lactose Ph. Eur | 488.5 |
| Magnesium stearate | 1.5 |

| (e) Injection I | (50 mg/ml) |
| --- | --- |
| Compound X | 5.0% w/v |
| 1M Sodium hydroxide solution | 15.0% v/v |
| 0.1M Hydrochloric acid (to adjust pH to 7.6) | 4.5% w/v |
| Polyethylene glycol 400 | |
| Water for injection to 100% | |

| (f) Injection II | (10 mg/ml) |
| --- | --- |
| Compound X | 1.0% w/v |
| Sodium phosphate BP | 3.6% w/v |
| 0.1M Sodium hydroxide solution | 15.0% v/v |
| Water for injection to 100% | |

| (g) Injection III | (1 mg/ml, buffered to pH6) |
| --- | --- |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol I | mg/ml |
| --- | --- |
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
| --- | --- |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
| --- | --- |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

5,482,966

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

We claim:

1. An oxime derivative of the formula I

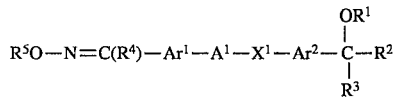

wherein $R^5$ is hydrogen, (1–4C)alkyl, (3–4C)alkenyl, (3–4C)alkynyl, (2–5C)alkanoyl, halogeno-(2–4C)alkyl, hydroxy-(2–4C)alkyl, (1–4C)alkoxy-(2–4C)alkyl, carbamoyl, N-(1–4C)alkylcarbamoyl, N,N-di-(1–4C)alkylcarbamoyl, amino-(2–4C)alkyl, (1–4C)alkylamino-(2–4C)alkyl, di-(1–4C)alkylamino-(2–4C)alkyl, (1–4C)alkylthio-(2–4C)alkyl, (1–4C)alkylsulphinyl-(2–4C)alkyl, (1–4C)alkylsulphonyl-(2–4C)alkyl, cyano-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-(1–4C)alkylcarbamoyl-(1–4C)alkyl, (2–5C)alkanoylamino-(2–4C)alkyl, (2–5C)alkanoyl-(1–4C)alkyl, phenyl-(1–4C)alkyl, heteroaryl-(1–4C)alkyl or heteroarylthio-(2–4C)alkyl and wherein each phenyl or heteroaryl group may optionally bear one or two substituents selected from halogeno, cyano, trifluoromethyl, carboxy, (1–4C)alkyl, (1–4C)alkoxy, (1–4C)alkoxycarbonyl, carboxy-(1–4C)alkyl and (1–4C)alkoxycarbonyl-(1–4C)alkyl;

and wherein said heteroaryl group in $R^5$ is a 5-membered or 6-membered heterocyclic moiety containing up to four nitrogen heteroatoms and said 6-membered heterocyclic moiety optionally containing a further heteroatom selected from oxygen and sulphur;

$Ar^1$ is phenylene or a 6-membered heteroaryl diradical containing one or two nitrogen heteroatoms which may optionally bear one or two substituents selected from halogeno, cyano, trifluoromethyl, hydroxy, amino, (1–4C)alkyl, (1–4C)alkoxy, phenyl-(1–4C)alkoxy, (1–4C)alkylamino and di-(1–4C)alkylamino;

$R^4$ is linked to $Ar^1$ ortho to the —N=C($R^4$)— group and defines an ethylene, propylene, 1-methylpropylene or vinylene group, a group of the formula

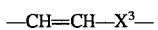

wherein $X^3$ is oxy or thio, or a group of the formula

—(CH$_2$)$_n$—X$^3$— wherein n is 1 or 2, $X^3$ is oxy, thio, sulphinyl, sulphonyl, imino or (1–4C)alkylimino, and one of the —CH$_2$— groups may optionally be replaced by a —CH(Me)— or —C(Me)$_2$— group;

$A^1$ is a direct link to $X^1$, or $A^1$ is (1–4C) alkylene;

$X^1$ is oxy, thio, sulphinyl or sulphonyl;

$Ar^2$ is phenylene, pyridinediyl, pyrimidinediyl, thiophenediyl, furandiyl, thiazolediyl, oxazolediyl, thiadiazolediyl, or oxadiazolediyl which may optionally bear one or two substituents selected from halogeno, cyano, trifluoromethyl, hydroxy, amino, (1–4C)alkyl, (1–4C)alkoxy, (1–4C)alkylamino and di-(1–4C)alkylamino;

$R^1$ is (1–4C)alkyl, (3–4C)alkenyl or (3–4C)alkynyl; and $R^2$ and $R^3$ together form a group of the formula —$A^2$—$X^2$—$A^3$— which together with the carbon atom to which $A^2$ and $A^3$ are attached define a ring having 5 or 6 ring atoms, wherein each of $A^2$ and $A^3$ is independently (1–3C)alkylene and $X^2$ is oxy, and which ring may optionally bear one or two substituents selected from hydroxy, (1–4C)alkyl and (1–4C)alkoxy;

or a pharmaceutically-acceptable salt thereof.

2. An oxime derivative of the formula I

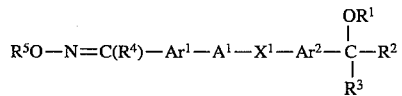

wherein $R^5$ is hydrogen, (1–4C)alkyl, (3–4C)alkenyl, (3–4C)alkynyl, (2–5C)alkanoyl, halogeno-(2–4C)alkyl, hydroxy-(2–4C)alkyl, (1–4C)alkoxy-(2–4C)alkyl, carbamoyl, N-(1–4C)alkylcarbamoyl, N,N-di-(1–4C)alkylcarbamoyl, amino-(2–4C)alkyl, (1–4C)alkylamino-(2–4C)alkyl, di-(1–4C)alkylamino-(2–4C)alkyl, (1–4C)alkylthio-(2–4C)alkyl, (1–4C)alkylsulphinyl-(2–4C)alkyl, (1–4C)alkylsulphonyl-(2–4C)alkyl, cyano-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-(1–4C)alkylcarbamoyl-(1–4C)alkyl, (2–5C)alkanoylamino-(2–4C)alkyl, (2–5C)alkanoyl-(1–4C)alkyl, phenyl-(1–4C)alkyl, heteroaryl-(1–4C)alkyl or heteroarylthio-(2–4C)alkyl and wherein each phenyl or heteroaryl group may optionally bear one or two substituents selected from halogeno, cyano, trifluoromethyl, carboxy, (1–4C)alkyl, (1–4C)alkoxy, (1–4C)alkoxycarbonyl, carboxy-(1–4C)alkyl and (1–4C)alkoxycarbonyl-(1–4C)alkyl;

and wherein said heteroaryl group in $R^5$ is a 5-membered or 6-membered heterocyclic moiety containing up to four nitrogen heteroatoms and said 6-membered heterocyclic moiety optionally containing a further heteroatom selected from oxygen and sulphur;

$Ar^1$ is phenylene or a 6-membered heteroaryl diradical containing one or two nitrogen heteroatoms which may optionally bear one or two substituents selected from halogeno, cyano, trifluoromethyl, hydroxy, amino, (1–4C)alkyl, (1–4C)alkoxy, phenyl-(1–4C)alkoxy, (1–4C)alkylamino and di-(1–4C)alkylamino;

$R^4$ is linked to $Ar^1$ ortho to the —N=C($R^4$)— group and defines an ethylene, propylene, 1-methylpropylene or vinylene group, a group of the formula

—CH=CH—$X^3$— wherein $X^3$ is oxy or thio, or a group of the formula

—(CH$_2$)$_n$—$X^3$— wherein n is 1 or 2, $X^3$ is oxy or thio, and one of the —CH$_2$— groups may optionally be replaced by a —CH(Me)— or —C(Me)$_2$— group;

$A^1$ is a direct link to $X^1$, or $A^1$ is (1–4C)alkylene;

$X^1$ is oxy, thio, sulphinyl or sulphonyl;

$Ar^2$ is phenylene, pyridinediyl, pyrimidinediyl, thiophenediyl, furandiyl, thiazolediyl, oxazolediyl, thiadiazolediyl, or oxadiazolediyl which may optionally bear one or two substituents selected from halogeno, cyano, trifluoromethyl, hydroxy, amino, (1–4C)alkyl, (1–4C)alkoxy, (1–4C)alkylamino and di-(1–4C)alkylamino;

$R^1$ is (1–4C)alkyl, (3–4C)alkenyl or (3–4C)alkynyl; and $R^2$ and $R^3$ together form a group of the formula —$A^2$—$X^2$—$A^3$— which together with the carbon atom to which $A^2$ and $A^3$ are attached define a ring having 5 or 6 ring atoms, wherein each of $A^2$ and $A^3$ is independently (1–3C)alkylene and $X^2$ is oxy, and which ring may optionally bear one or two substituents selected from hydroxy, (1–4C)alkyl and (1–4C)alkoxy;

or a pharmaceutically-acceptable salt thereof.

3. An oxime derivative of the formula I as claimed in claim 2 or claim 1 wherein;

$R^5$ is hydrogen, methyl, ethyl, propyl, isopropyl, allyl, prop-2-ynyl, acetyl, propionyl, butyryl, pivaloyl, 2-fluoroethyl, 2-hydroxyethyl, 2-methoxyethyl, 2-methylthioethyl, cyanomethyl, carboxymethyl, methoxycarbonylmethyl, ethoxycarbonylmethyl, benzyl, acetonyl or 2-, 3- or 4-pyridylmethyl;

$Ar^1$ is 1,4-phenylene and $R^4$ is linked to $Ar^1$ ortho to the —N=C($R^4$)— group and defines an ethylene or vinylene group, or a group of the formula

—CH$_2$CH$_2$O—;

$A^1$ is a direct link to $X^1$ and $X^1$ is thio or sulphonyl, or $A^1$ is methylene and $X^1$ is oxy;

$Ar^2$ is 1,3-phenylene which may optionally bear one or two fluoro substituents or $Ar^2$ is 3,5-pyridinediyl, 2-amino-4,6-pyrimidinediyl, 2,4- or 2,5-thiophenediyl or 2,4- or 2,5-thiazolediyl;

$R^1$ is methyl, ethyl or allyl;

and $R^2$ and $R^3$ together form a group of the formula —$A^2$—$X^2$—$A^3$— which together with the carbon atom to which $A^2$ and $A^3$ are attached define a ring having 5 or 6 ring atoms, wherein $A^2$ is methylene or ethylene, $A^3$ is ethylene and $X^2$ is oxy, and which ring may optionally bear one or two substituents selected from methyl and ethyl;

or a pharmaceutically-acceptable salt thereof.

4. An oxime derivative of the formula I as claimed in claim 2 wherein;

$R^5$ is hydrogen, methyl, ethyl, propyl, isopropyl, allyl, prop-2-ynyl, acetyl, propionyl, butyryl, pivaloyl, 2-fluoroethyl, 2-hydroxyethyl, 2-methoxyethyl, 2-methylthioethyl, cyanomethyl, carboxymethyl, methoxycarbonylmethyl, ethoxycarbonylmethyl or 2-, 3- or 4-pyridylmethyl;

$Ar^1$ is 1,4-phenylene and $R^4$ is linked to $Ar^1$ ortho to the —N=C($R^4$)— group and defines an ethylene or vinylene group, or a group of the formula

—CH$_2$CH$_2$O—;

$A^1$ is a direct link to $X^1$ and $X^1$ is thio or sulphonyl, or $A^1$ is methylene and $X^1$ is oxy;

$Ar^2$ is 1,3-phenylene which may optionally bear one or two fluoro substituents, or $Ar^2$ is 3,5-pyridinediyl, 2-amino-4,6-pyrimidinediyl, 2,4- or 2,5-thiophenediyl or 2,4- or 2,5-thiazolediyl;

$R^1$ is methyl, ethyl or allyl;

and $R^2$ and $R^3$ together form a group of the formula —$A^2$—$X^2$—$A^3$— which together with the carbon atom to which $A^2$ and $A^3$ are attached define a ring having 5 or 6 ring atoms, wherein $A^2$ is methylene or ethylene, $A^3$ is ethylene and $X^2$ is oxy, and which ring may optionally bear one or two substituents selected from methyl and ethyl;

or a pharmaceutically-acceptable salt thereof.

5. An oxime derivative of the formula I as claimed in claim 2 or claim 1 wherein $R^5$ is hydrogen, methyl, acetyl, pivaloyl, cyanomethyl, 3-pyridylmethyl or 4-pyridylmethyl;

$Ar^1$ is 1,4-phenylene and $R^4$ is linked to $Ar^1$ ortho to the —N=C($R^4$)— group and defines an ethylene group, or a group of the formula

—CH$_2$CH$_2$O—;

$A^1$ is a direct link to $X^1$ and $X^1$ is thio, or $A^1$ is methylene and $X^1$ is oxy;

$Ar^2$ is 1,3-phenylene, 5-fluoro-1,3-phenylene, 2-amino-4,6-pyrimidinediyl, 2,4-thiophenediyl (with the $X^1$ group in the 2-position) or 2,5-thiazolediyl (with the $X^1$ group in the 2-position);

$R^1$ is methyl; and $R^2$ and $R^3$ together form a group of the formula —$A^2$—$X^2$—$A^3$— which together with the carbon atom to which $A^2$ and $A^3$ are attached define a ring having 5 or 6 atoms, wherein $A^2$ is methylene or ethylene, $A^3$ is ethylene and $X^2$ is oxy, and which ring may optionally bear a methyl substituent alpha to $X^2$;

or a pharmaceutically-acceptable salt thereof.

6. An oxime derivative, or a pharmaceutically-acceptable salt thereof, selected from:
(E)-5-[5-fluoro-3-(4-methoxytetrahydropyran-4-yl)phenylthio]indan-1-one oxime O-cyanomethyl ether,
7-[5-fluoro-3-(4-methoxytetrahydropyran-4-yl)phenylthio]chroman-4-one oxime,
7-[5-fluoro-3-(4-methoxytetrahydropyran-4-yl)phenylthio]chroman-4-one oxime O-methyl ether, and
(E)-5-[5-fluoro-3-(4-methoxytetrahydropyran-4-yl)phenylthio]indan-1-one O-(4-pyridyl)methyl ether.

7. An oxime derivative, or a pharmaceutically-acceptable salt thereof, selected from:
(E)-5-{4-[(2S,4R)-4-methoxy-2-methyltetrahydropyran-4-yl]thien-2-ylthio}indan-1-one oxime,
(E)-5-{4-[(2S,4R)-4-methoxy-2-methyltetrahydropyran-4-yl]thien-2-ylthio}indan-1-one oxime O-cyanomethyl ether, and
(E)-7-[4-(4-methoxytetrahydropyran-4-yl)thien-2-ylthio]chroman-4-one oxime O-cyanomethyl ether.

8. A pharmaceutical composition which comprises an oxime derivative of the formula I, or a pharmaceutically-acceptable salt thereof, as claimed in any one of claims 1, 2, 4, 6 and 7 in association with a pharmaceutically-acceptable diluent or carrier.

9. A method of treating a disease or medical condition mediated alone or in part by one or more leukotrienes which comprises administering to a warm blooded animal requiring such treatment an effective amount of an oxime derivative of the formula I, or a pharmaceutically-acceptable salt thereof, as claimed in any one of claims 1, 2, 4, 6 and 7.

10. A pharmaceutical composition which comprises an oxime derivative of the formula I, or a pharmaceutically-acceptable salt thereof, as claimed in any one of claims 1, 2, 4, 6 and 7 in conjunction or admixture with a cyclooxygenase inhibitory non-steroidal anti-inflammatory agent, and a pharmaceutically-acceptable diluent or carrier.

11. A pharmaceutical composition which comprises an oxime derivative of the formula I, or a pharmaceutically-acceptable salt thereof, as claimed in claim 3 in association with a pharmaceutically-acceptable diluent or carrier.

12. A pharmaceutical composition which comprises an oxime derivative of the formula I, or a pharmaceutically-acceptable salt thereof, as claimed in claim 5 in association with a pharmaceutically-acceptable diluent or carrier.

13. A method of treating a disease or medical condition mediated alone or in part by one or more leukotrienes which comprises administering to a warm blooded animal requiring such treatment an effective amount of an oxime derivative of the formula I, or a pharmaceutically-acceptable salt thereof, as claimed in claim 3.

14. A method of treating a disease or medical condition mediated alone or in part by one or more leukotrienes which comprises administering to a warm blooded animal requiring such treatment an effective amount of an oxime derivative of the formula I, or a pharmaceutically-acceptable salt thereof, as claimed in claim 5.

15. A pharmaceutical composition which comprises an oxime derivative of the formula I, or a pharmaceutically-acceptable salt thereof, as claimed in claim 3 in conjunction or admixture with a cyclooxygenase inhibitory non-steroidal anti-inflammatory agent, and a pharmaceutically-acceptable diluent or carrier.

16. A pharmaceutical composition which comprises an oxime derivative of the formula I, or a pharmaceutically-acceptable salt thereof, as claimed in claim 5 in conjunction or admixture with a cyclooxygenase inhibitory non-steroidal anti-inflammatory agent, and a pharmaceutically-acceptable diluent or carrier.

* * * * *